United States Patent

Amishiro et al.

Patent Number: 5,670,492
Date of Patent: Sep. 23, 1997

[54] DC-89 DERIVATIVES

[75] Inventors: Nobuyoshi Amishiro, Shizuoka; Satoru Nagamura, Hofu; Hiromitsu Saito, Kawasaki; Eiji Kobayashi, Tokyo; Akihiko Okamoto, Numazu; Katsushige Gomi, Susono, all of Japan

[73] Assignee: Kyowa Hakko Kogyo Co., Ltd., Tokyo, Japan

[21] Appl. No.: 557,055

[22] PCT Filed: Mar. 31, 1995

[86] PCT No.: PCT/JP95/00626

§ 371 Date: Nov. 28, 1995

§ 102(e) Date: Nov. 28, 1995

[87] PCT Pub. No.: WO95/26964

PCT Pub. Date: Oct. 12, 1995

[30] Foreign Application Priority Data

Apr. 1, 1994 [JP] Japan .................. 6-065236

[51] Int. Cl.$^6$ .................. A61K 31/40; A61K 31/495; A61K 31/405; C07D 487/04
[52] U.S. Cl. .................. 514/63; 514/252; 514/253; 514/410; 514/322; 514/411; 544/315; 544/316; 544/360; 544/364; 544/238; 544/373; 546/14; 546/19; 548/406; 548/421; 548/433
[58] Field of Search .................. 544/373, 229, 544/315, 316, 360, 364, 238; 548/406, 421, 433, 425; 546/14, 199; 514/253, 252, 63, 322, 410, 411

[56] References Cited

U.S. PATENT DOCUMENTS

| 4,912,227 | 3/1990 | Kelly et al. | 548/421 |
| 5,070,092 | 12/1991 | Kanda et al. | 544/373 |
| 5,258,383 | 11/1993 | Nagamura et al. | 544/373 |
| 5,332,837 | 7/1994 | Kelly et al. | 548/433 |

FOREIGN PATENT DOCUMENTS

| 154445 | 2/1985 | European Pat. Off. |
| 0520435 | 12/1992 | European Pat. Off. |
| 502005 | 7/1990 | Japan |

*Primary Examiner*—Mukund J. Shah
*Assistant Examiner*—Sabiha Qazi
*Attorney, Agent, or Firm*—Fitzpatrick, Cella, Harper & Scinto

[57] ABSTRACT

Provided are DC-89 derivatives represented by the formula:

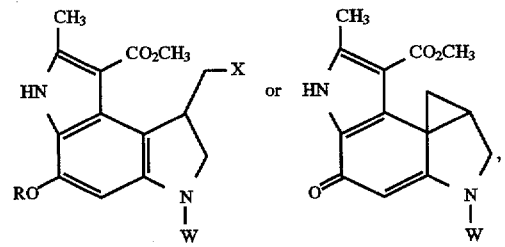

wherein X represents Cl or Br, R represents hydrogen or $COR^1$, and W represents

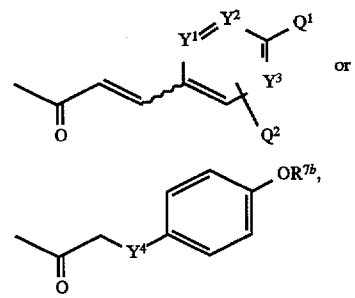

and pharmaceutically acceptable salts thereof.

The compounds of the present invention have excellent anti-tumor activity and are useful as anti-tumor agents.

3 Claims, No Drawings

DC-89 DERIVATIVES

This is a 371 of PCT/JP95/00626, filed Mar. 31, 1995.

TECHNICAL FIELD

The present invention relates to DC-89 derivatives. The compounds of the present invention exhibit excellent anti-tumor activity and are useful as anti-tumor agents.

BACKGROUND ART

As DC-89 derivatives, DC-89A1, DC-89A2, DC-89B1 and DC-89B2 represented by the following structural formula are known, and these compounds exhibit antibacterial activity against various bacteria and also antitumor activity against melanoma B-16, etc.

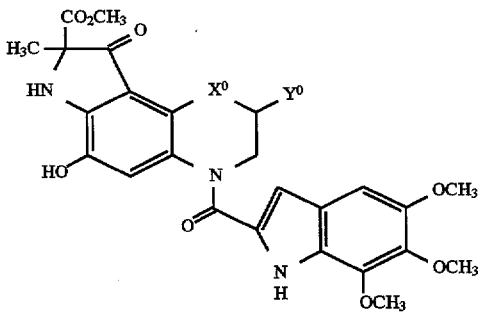

DC-89A1: $X^o$=—CH$_2$—, $Y^o$=Cl

DC-89A2: $X^o$=single bond, $Y^o$=CH$_2$Cl

DC-89B1: $X^o$=—CH$_2$—, $Y^o$=Br

DC-89B2: $X^o$=single bond, $Y^o$=CH$_2$Br

DC-89A1 is disclosed in WO87/06265, and DC-89A2, DC-89B1 and DC-89B2 are disclosed in JP,A,2-119787. SF2582A and SF2582B, which are the same compounds as DC-89A2 and DC-89A1, are disclosed in JP,A,1-139590. In relation to the compounds of the present invention, DC-88A and DC113 having the following structural formulae are disclosed in WO87/06265 and JP,A,2-177890, respectively. These compounds exhibit not only antibacterial activity against various bacteria but also anti-tumor activity against melanoma B-16, etc.

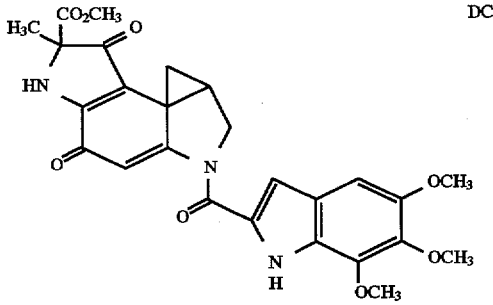

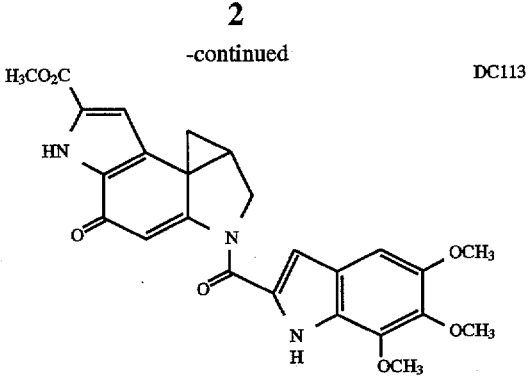

DC-88A derivatives and DC-89 derivatives are disclosed in JP,A,2-288879, JP,A,3-7287, JP,A,3-128379, JP,A,4-226988, JP,A,4-356485, JP,A,5-51384 and JP,A,5-178858.

Derivatives of SF2582C are disclosed in JP,A,1-278881. CC-1065 and derivatives thereof are disclosed in JP,A,54-64695, JP,A,60-193989, WO88/04659, EP-359454 and JP,A,3-14581. Related derivatives are disclosed in JP,A,6-116269.

JP,A,5-178858 discloses Compounds (A), (B) and (C) represented by the following formulae. However, Compounds (B) and (C) lack satisfactory water-solubility when these compounds are used as injections.

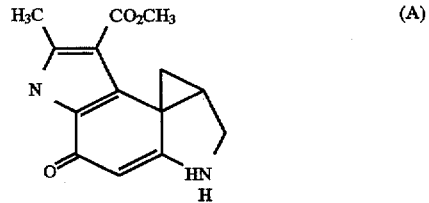

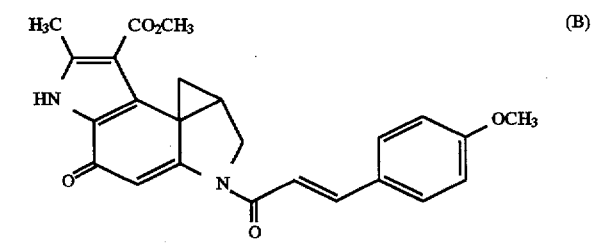

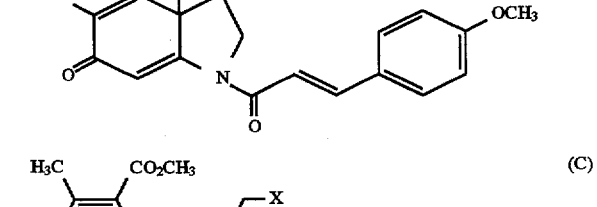

It is an object of this invention to provide DC-89 derivatives which have excellent anti-tumor activity and excellent water-solubility.

Disclosure of the Invention

The present invention provides DC-89 derivatives represented by formula (I):

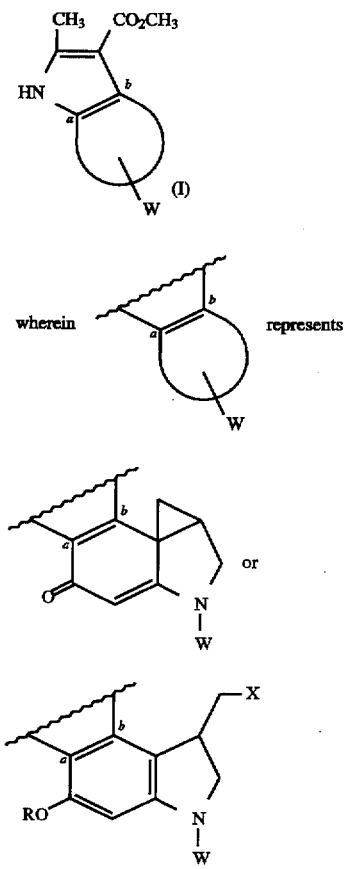

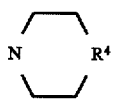

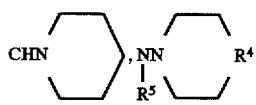

in which X represents Cl or Br, R represents hydrogen or COR¹ in which R¹ represents hydrogen, substituted or unsubstituted lower alkyl, substituted or unsubstituted aryl, substituted or unsubstituted heterocyclic group, NR²R³ (in which R² and R³ independently represent hydrogen or substituted or unsubstituted lower alkyl, amino, or mono- or di(lower alkyl)amino), in which R⁴ represents oxygen, N—R⁵ (in which R⁵ represents hydrogen or lower alkyl), CH₂ or (in which R⁴ and R⁵ are the same meanings as defined above), or OR⁶ (in which R⁶ represents substituted or unsubstituted lower alkyl, or substituted or unsubstituted aryl); and W represents

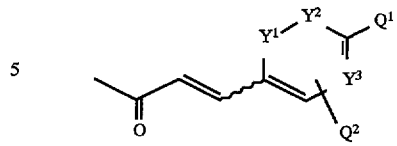

in which $Y^1$, $Y^2$ and $Y^3$ independently represent CH or N, $Q^1$ and $Q^2$ independently represent hydrogen, $OR^7$ (in which $R^7$ represents hydrogen or substituted or unsubstituted lower alkyl), $NR^{2a}R^{3a}$ (in which $R^{2a}$ and $R^{3a}$ are the same meanings as $R^2$ and $R^3$ defined above), $NHCO_2R^{6a}$ (in which $R^{6a}$ is the same meaning as $R^6$ defined above), or $O(CH_2)_nR^8$ in which n represents an integer of 1 to 4, and $R^8$ represents $CO_2R^{7a}$ (in which $R^{7a}$ is the same meaning as $R^7$ defined above), $N_3$, or $NR^{2b}R^{3b}$ (in which $R^{2b}$ and $R^{3b}$ are the same meanings as $R^2$ and $R^3$ defined above), provided that when $Q^1$ is $OCH_3$ and $Y^1$, $Y^2$ and $Y^3$ are CH, $Q^2$ is a group other than hydrogen, or

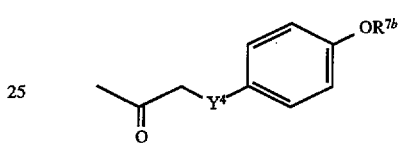

(in which $Y^4$ represents oxygen, sulfur or NH, and $R^{7b}$ is the same meaning as $R^7$ defined above), and pharmaceutically acceptable salts thereof.

The compounds represented by formula (I) are hereinafter referred to as Compounds (I). Similarly, the compounds represented by formula (I) to (IV) are referred to as Compounds (I) to (IV). Compounds (I)a, (I)b and the like are intended to be included in Compounds (I).

In the definition of the above-mentioned formula (I), lower alkyl and the alkyl moiety of mono- or di(lower alkyl)amino include linear or branched alkyl groups having 1 to 8 carbon atoms such as methyl, ethyl, propyl, isopropyl, butyl, isobutyl, sec-butyl, tert-butyl, pentyl, isopentyl, hexyl, isohexyl, heptyl, octyl and iso-octyl. Examples of aryl include phenyl and naphthyl. Examples of the heterocyclic group include pyridyl, pyrazinyl and pyrimidinyl. The substituted lower alkyl has 1 to 3 independently-selected substituents such as lower alkoxy, lower alkylthio optionally substituted by carboxy, carboxy, lower alkoxycarbonyl, amino, mono- or di(lower alkyl)amino, cyclic amino optionally substituted by lower alkyl or cyclic amino, halogen and phenyl. Examples of the cyclic amino include pyrrolidinyl, piperidino, piperazinyl and morpholino. Lower alkyl and the alkyl moiety of lower alkoxy, lower alkylthio, lower alkoxycarbonyl and mono- or di(lower alkyl)amino has the same definition as that of the above-mentioned lower alkyl. Examples of halogen include fluorine, chlorine, bromine and iodine atoms. The substituted aryl and the substituted heterocyclic group each has 1 to 3 independently selected substituents such as substituted or unsubstituted lower alkyl, lower alkoxy, lower alkoxycarbonyl, amino, mono- or di(lower alkyl)amino and halogen, in which lower alkyl and the alkyl moiety of lower alkoxy, lower alkoxycarbonyl and mono- or di(lower alkyl)amino has the same definition as that of the above-mentioned lower alkyl, and the substituents and halogen of substituted lower alkyl are the same meanings as defined above.

Examples of the pharmaceutically acceptable salts of Compounds (I) include inorganic acid-addition salts such as hydrochloride, hydrobromide, hydroiodide, sulfate, phosphate and nitrate, and organic acid-addition salts such as acetate, benzoate, maleate, fumarate, succinate, tartrate, citrate, oxalate, glyoxylate, aspartate and methanesulfonate.

The processes for preparing Compounds (I) are described below.

When the defined group changes under reaction conditions or are inappropriate for conducting the processes, the processes can be easily carried out by using protection/deprotection method for functional groups conventionally employed in the organic synthetic chemistry including oxidation, reduction and hydrolysis.

Process 1

Among Compounds (I), Compound (I)a wherein

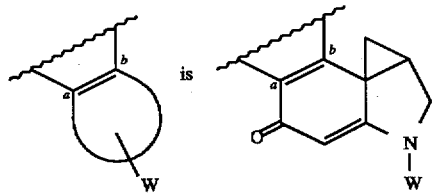

can be prepared by reacting Compound (A) disclosed in JP,A,5-178858 with a reactive derivative of the corresponding carboxylic acid in an inert solvent in the presence of a base.

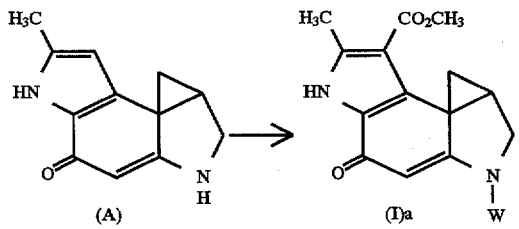

In the formulae, W is the same meanings as defined above.

Examples of the base include sodium hydride, lithium diisopropylamide, potassium tert-butoxide, triethylamine, 4-dimethylaminopyridine. The base is usually used in an amount of 1 to 3 equivalents based on Compound (A). As the inert solvent, dimethylformamide, tetrahydrofuran, toluene, dimethylsulfoxide, etc. may be used singly or in combination. Examples of the reactive derivative of the carboxylic acid include acid halides such as acid chlorides and acid bromides, and activated esters such as p-nitrophenyl esters, 2,4,5-trichlorophenyl esters, pentafluorophenyl esters and N-oxysuccinimide esters. The reactive derivative is usually used in an amount of 1 to 3 equivalents based on Compound (A). The reaction is conducted at −80° C. to 30° C. for 30 minutes to 1 day.

Process 2

Among Compounds (I), Compound (I)b wherein

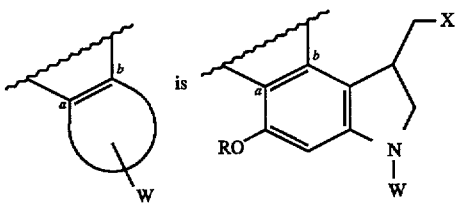

and R is hydrogen can be prepared by reacting Compound (I)a with hydrochloric acid or hydrobromic acid in an inert solvent.

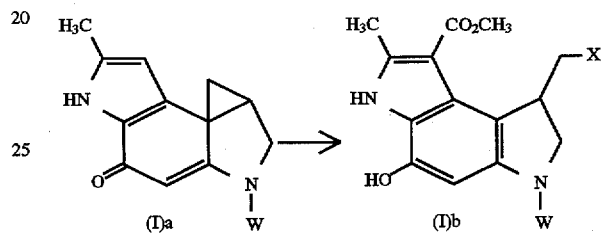

In the formulae, W and X are the same meanings as defined above.

Hydrochloric acid or hydrobromic acid is usually used in an amount of 1 to 20 equivalents based on Compound (I)a. As the inert solvent, water, dimethylformamide, tetrahydrofuran, toluene, dioxane, acetonitrile, etc. may be used singly or in combination. The reaction is usually conducted at −30° C. to 50° C. and for 10 minutes to 1 hour.

Process 3-1

Among Compounds (I), Compound (I)c wherein

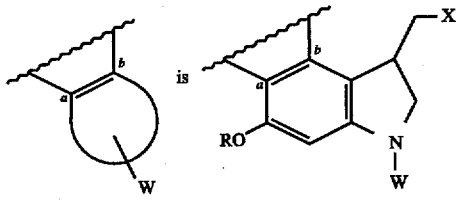

and R is $COR^1$ in which $R^1$ is hydrogen, substituted or unsubstituted lower alkyl, substituted or unsubstituted aryl or a substituted or unsubstituted heterocyclic group can be prepared by reacting Compound (I)b with a condensation agent such as dicyclohexylcarbodiimide (DCC) and N-ethyl-N'-(3-dimethylaminopropyl)carbodiimide, 4-dimethylaminopyridine and $R^{1a}CO_2^H$ (in which $R^{1a}$ represents hydrogen, substituted or unsubstituted alkyl, substituted or unsubstituted aryl or a substituted or unsubstituted heterocyclic ring in the definition of $R^1$) in an inert solvent.

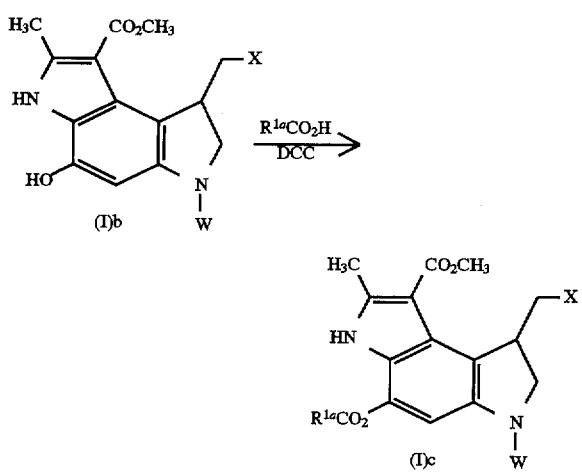

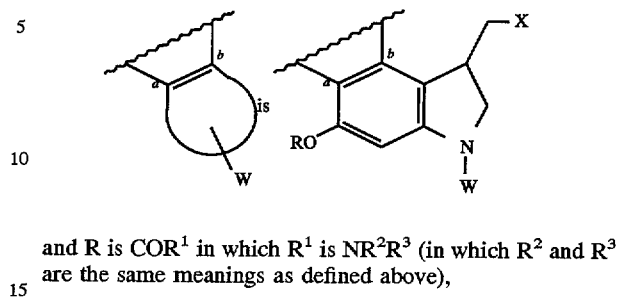

Process 4

Among Compounds (I), compound (I)d wherein

and R is COR$^1$ in which R$^1$ is NR$^2$R$^3$ (in which R$^2$ and R$^3$ are the same meanings as defined above),

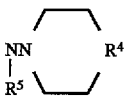

(in which R$^4$ is the same meaning as defined above), or (in which R$^4$ and R$^5$ are the same meanings as defined above) can be prepared according to the following steps.

In the formulae, R$^{1a}$, W and X are the same meanings as defined above.

R$^{1a}$CO$_2$H, DCC and 4-dimethylaminopyridine are usually used in amounts of 1 to 10 equivalents based on Compound (I)b. As the inert solvent, methylene chloride, chloroform, dimethylformamide, tetrahydrofuran, toluene, dioxane, acetonitrile, etc. may be used singly or in combination. The reaction is usually conducted at −50° C. to 50° C. for 10 minutes to 2 days.

Process 3-2

Compound (I)c can be prepared by reacting Compound (I)b with an acid anhydride such as (R$^{1a}$CO)$_2$O or an acid chloride such as R$^{1a}$COCl in an inert solvent in the presence of a base.

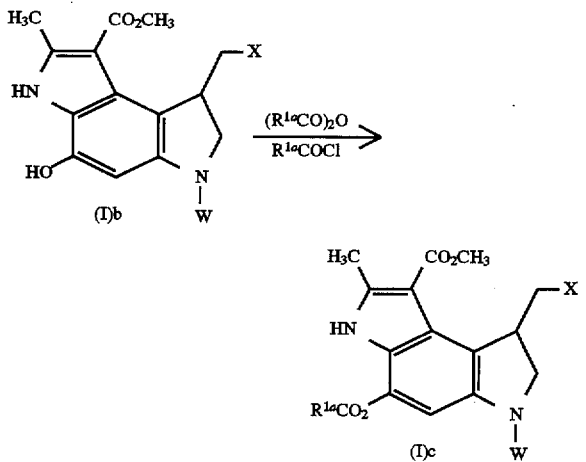

In the formulae, R$^{1a}$, W and X are the same meanings as defined above.

The acid anhydride or the acid chloride is usually used in an amount of 1 to 10 equivalents based on Compound (I)b. As the base, potassium tert-butoxide, triethylamine, pyridine, 4-dimethylaminopyridine, etc. may be usually used in an amount of 1 to 10 equivalents based on Compound (I)b. However, when this base serves also as a solvent, it is used in large excess. As the inert solvent, methylene chloride, chloroform, dimethylformamide tetrahydrofuran, toluene, dioxane, acetonitrile, etc. may be used singly or in combination. The reaction is usually conducted at −20° C. to 50° C. for 10 minutes to 10 hours.

(Step 1)

Compound (III) can be prepared by reacting Compound (I)b with p-nitrophenyl chloroformate in an inert solvent in the presence of a base.

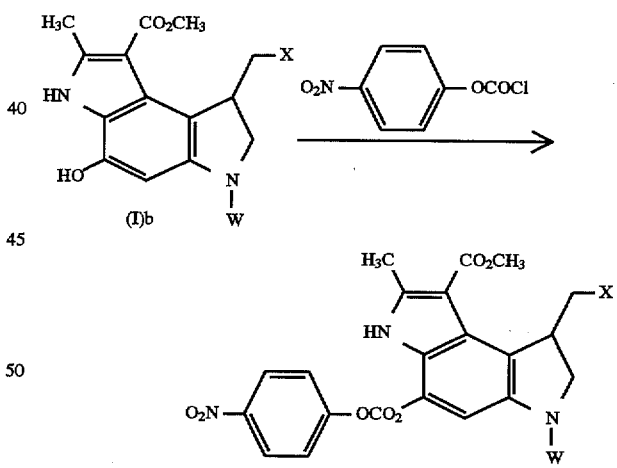

In the formulae, W and X are the same meanings as defined above.

p-Nitrophenyl chloroformate is usually used in an amount of 1 to 5 equivalents based on Compound (I)b. Examples of the base include potassium t-butoxide, triethylamine, pyridine and 4-dimethylaminopyridine. The base is usually used in an amount of 1 to 5 equivalents based on Compound (I)b. However, when the base serves also as a solvent, it is used in large excess. As the inert solvent, methylene chloride, chloroform, pyridine, dimethylformamide, tetrahydrofuran, toluene, dioxane, etc. may be used singly or in combination.

The reaction is usually conducted at −80° C. to 50° C. for 10 minutes to 20 hours.

(Step 2)

Compound (I)d can be prepared by reacting Compound (III) with Compound (IV) represented by the formula

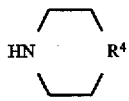   (IV)a wherein $R^2$ and $R^3$ are the same meanings as defined above,

   (IV)b wherein $R^4$ is the same meanings as defined above, or

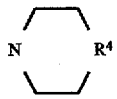   (IV)c wherein $R^4$ and $R^5$ are the same meanings as defined above, in an inert solvent and in the presence of a base.

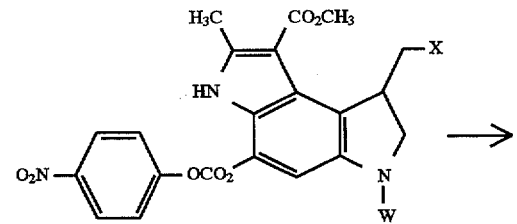

(III)

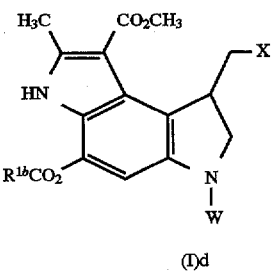

(I)d wherein $R^{1b}$ is $NR^2R^3$,

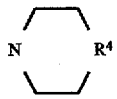

in which $R^4$ is the same meaning as defined above, or

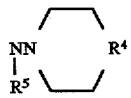

in which $R^4$ and $R^5$ are the same meanings as defined above, and W and X are the same meanings as defined above.

Examples of the base include triethylamine, pyridine and 4-dimethylaminopyridine. The base is usually used in an amount of 1 to 5 equivalents based on Compound (III). However, when the base serves also as a solvent, it is used in large excess. As the inert solvent, methylene chloride, chloroform, dimethylformamide, tetrahydrofuran, toluene, dioxane, etc. may be used singly or in combination. The reaction is usually conducted at −80° C. to 50° C. for 10 minutes to 1 day.

Process 5

Among Compounds (I), Compound (I)e wherein

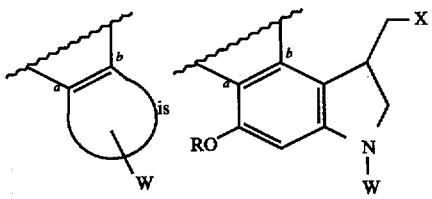

and R is $COR^1$ in which $R^1$ is $OR^6$ (in which $R^6$ is the same meaning as defined above) can be prepared by reacting Compound (I)b with $ClCO_2R^6$ (in which $R^6$ is the same meaning as defined above) in an inert solvent in the presence of a base.

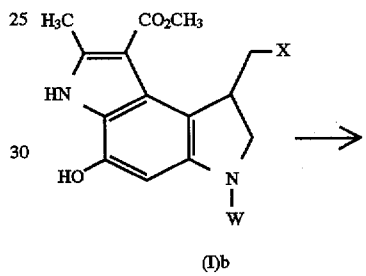

(I)b

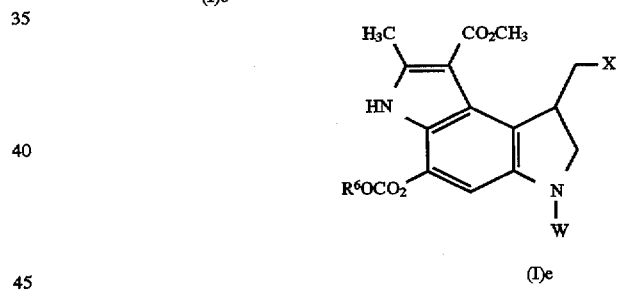

(I)e

In the formulae, $R^6$, W and X are the same meanings as defined above.

$ClCO_2R^6$ is usually used in an amount of 1 to 10 equivalents based on Compound (I)b. Examples of the base include potassium tert-butoxide, triethylamine, pyridine and 4-dimethylaminopyridine. The base is usually used in an amount of 1 to 5 equivalents based on Compound (I)b. However, when the base serves also as a solvent, it is used in large excess. As the inert solvent, methylene chloride, chloroform, dimethylformamide, tetrahydrofuran, toluene, dioxane, etc. may be used singly or in combination. The reaction is usually conducted at −40° C. to 50° C. for 10 minutes to 10 hours.

After the completion of the reaction of each step, water, acid, buffer, an aqueous solution of sodium hydrogen carbonate, etc. is added to the reaction mixture, if necessary, and the mixture is extracted with an organic solvent such as ethyl acetate, chloroform and ether. The extract is washed with water, an aqueous solution of sodium hydrogen carbonate, an aqueous solution of sodium chloride, etc., and is then dried over anhydrous sodium sulfate, etc. After the solvent is evaporated, the resulting residue is purified by silica-gel column chromatography, thin-layer chromatography, high-performance preparative liquid chromatography, recrystallization, etc.

In the case where a salt of Compound (I) is desired and it is obtained in the form of the desired salt, it can be subjected to purification as such. In the case where Compound (I) is obtained in the free state and its salt is desired, the desired salt can be obtained by dissolving or suspending Compound (I) in a suitable solvent and adding a suitable acid to the solution or suspension.

The reaction intermediates may be directly used in the subsequent step without isolation or purification. Compounds (I) and its pharmaceutically acceptable salts may be in the form of adducts with water or various solvents, which are also within the scope of the present invention. Further, all possible isomers of Compounds (I) including optical isomers and mixtures thereof also fall within the scope of the present invention.

The structures and the compound numbers of representative compounds which fall under Compounds (I) are shown in Table 1.

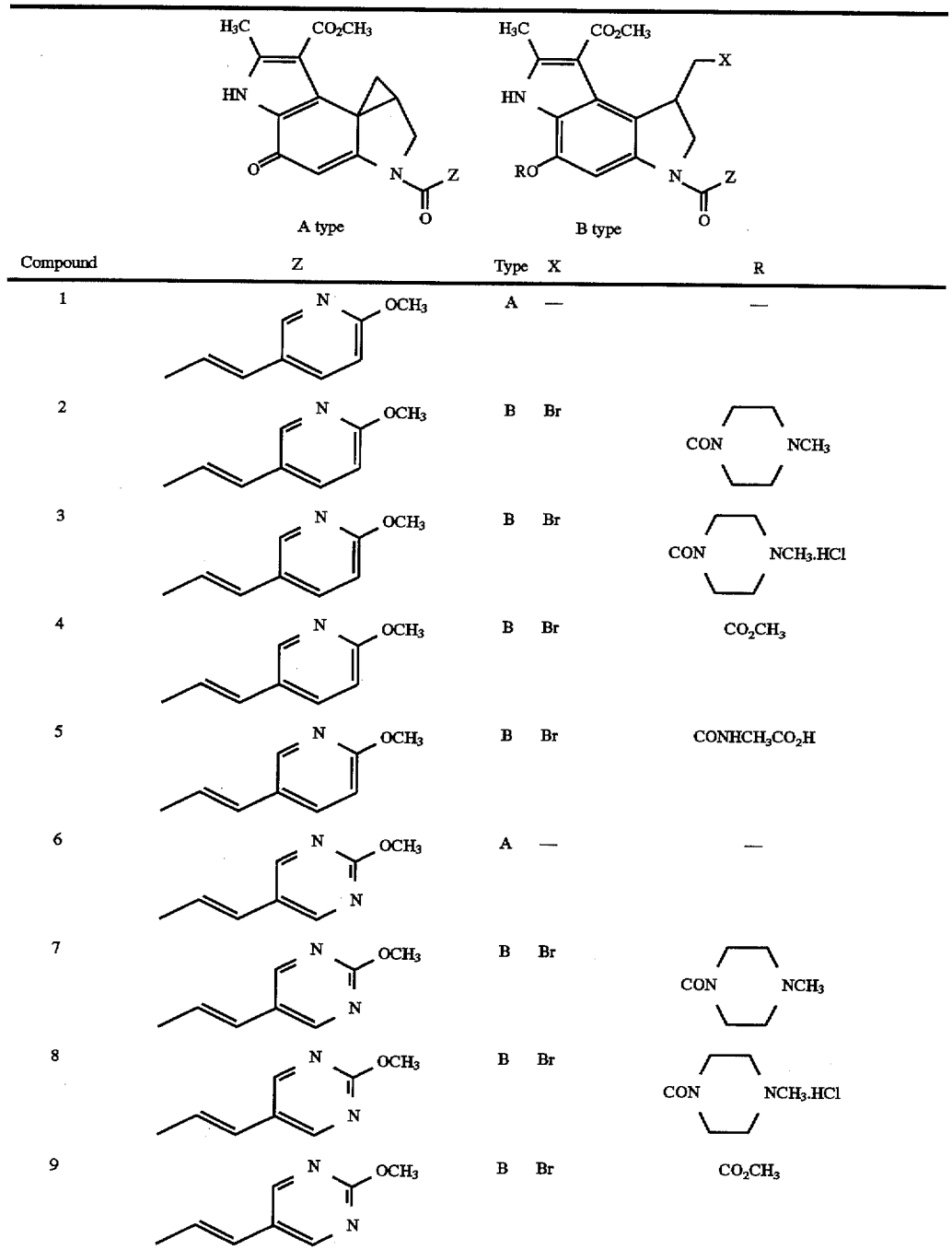

TABLE 1

TABLE 1-continued

A type / B type structures (as shown in header)

| Compound | Z | Type | X | R |
|---|---|---|---|---|
| 10 | methoxy-pyrimidine with propenyl substituent | B | Br | $CONHCH_2CO_2H$ |
| 11 | methoxy-pyrimidine with propenyl substituent | B | Br | $COCH_3$ |
| 12 | methoxy-pyridazine with propenyl substituent | A | — | — |
| 13 | methoxy-pyridazine with propenyl substituent | B | Br | $CON(CH_2CH_2)_2NCH_3$ (N-methylpiperazinyl carbonyl) |
| 14 | methoxy-pyridazine with propenyl substituent | B | Br | $CON(CH_2CH_2)_2NCH_3 \cdot HCl$ |
| 15 | methoxy-pyridine with propenyl substituent | A | — | — |
| 16 | methoxy-pyridine with propenyl substituent | B | Br | $CON(CH_2CH_2)_2NCH_3$ |
| 17 | methoxy-pyridine with propenyl substituent | B | Br | $CON(CH_2CH_2)_2NCH_3 \cdot HCl$ |
| 18 | methoxy-ethoxy-phenyl | A | — | — |
| 19 | methoxy-ethoxy-phenyl | B | Br | $CON(CH_2CH_2)_2NCH_3$ |
| 20 | methoxy-ethoxy-phenyl | B | Br | $CON(CH_2CH_2)_2NCH_3 \cdot HCl$ |

TABLE 1-continued

A type: [structure with spiro cyclopropane, carbonyl, HN, CO2CH3, H3C, and N-C(=O)-Z group]

B type: [structure with CH2X, HN, CO2CH3, H3C, RO, and N-C(=O)-Z group]

| Compound | Z | Type | X | R |
|---|---|---|---|---|
| 21 | 4-(OCH₂CH₂CH₃)-phenyl with ethoxy substituent | A | — | — |
| 22 | 4-(O(CH₂)₄CH₃)-phenyl with ethoxy substituent | A | — | — |
| 23 | 4-(OCF₃)-phenyl with ethoxy substituent | A | — | — |
| 24 | 4-(OCF₃)-phenyl with ethoxy substituent | B | Br | CON(piperazine)NCH₃ |
| 25 | 4-(OCF₃)-phenyl with ethoxy substituent | B | Br | CON(piperazine)NCH₃·HCl |
| 26 | 4-(NHCO₂C(CH₃)₃)-styryl | A | — | — |
| 27 | 4-(N(CH₃)₂)-styryl | A | — | — |
| 28 | 4-(NH₂)-styryl | A | — | — |
| 29 | 4-methoxy-3-(O(CH₂)₃N₃)-styryl | A | — | — |
| 30 | 4-methoxy-3-(O(CH₂)₃NH₂)-styryl | A | — | — |
| 31 | 4-methoxy-3-(O(CH₂)₃NH₂)-styryl | B | Br | CON(piperazine)NCH₃ |
| 32 | 4-methoxy-3-(O(CH₂)₃NH₂·HCl)-styryl | B | Br | CON(piperazine)NCH₃·HCl |

TABLE 1-continued

| Compound | Z | Type | X | R |
|---|---|---|---|---|
| 33 | 5-(1-propenyl)-2-methoxy-phenyl with O(CH$_2$)$_3$N(CH$_3$)$_2$ | A | — | — |
| 34 | 5-(1-propenyl)-2-methoxy-phenyl with OCH$_2$CO$_2$CH$_3$ | A | — | — |
| 35 | 5-(1-propenyl)-2-methoxy-phenyl with OCH$_2$CO$_2$C(CH$_3$)$_3$ | A | — | — |
| 36 | 5-(1-propenyl)-2-methoxy-phenyl with OCH$_2$CO$_2$H | B | Br | CON(CH$_3$)$_2$ |
| 37 | 5-(1-propenyl)-2-methoxy-phenyl with NH$_2$ | A | — | — |
| 38 | 5-(1-propenyl)-2-methoxy-phenyl with NH$_2$ | B | Br | CO$_2$CH$_3$ |
| 39 | 5-(1-propenyl)-2-methoxy-phenyl with NH$_2$ | B | Br | CON(piperazinyl)NCH$_3$ |
| 40 | 5-(1-propenyl)-2-methoxy-phenyl with NH$_2$·HCl | B | Br | CON(piperazinyl)NCH$_3$·HCl |
| 41 | 5-(1-propenyl)-2-methoxy-phenyl with N(CH$_3$)$_2$ | A | — | — |
| 42 | 5-(1-propenyl)-2-methoxy-phenyl with N(CH$_3$)$_2$ | B | Br | CON(piperazinyl)NCH$_3$ |
| 43 | 5-(1-propenyl)-2-methoxy-phenyl with N(CH$_3$)$_2$·HCl | B | Br | CON(piperazinyl)NCH$_3$·HCl |

TABLE 1-continued
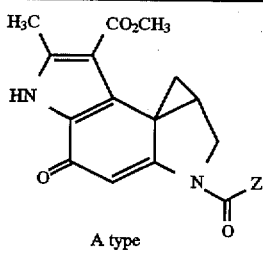
A type
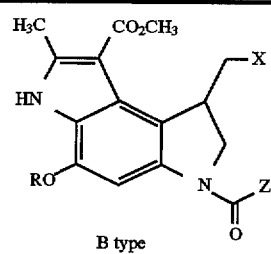
B type
| Compound | Z | Type | X | R |
|---|---|---|---|---|
| 44 | 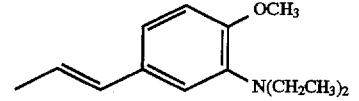 | B | Br | COCH₃ |
| 45 |  | B | Br | COCH₃ |
| 46 | 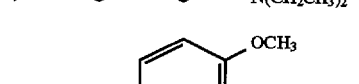 | A | — | — |
| 47 | 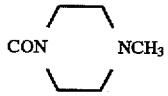 | B | Br | CO₂CH₃ |
| 48 | 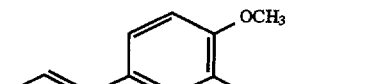 | B | Br | 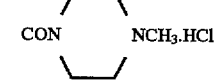 |
| 49 | 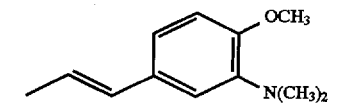 | B | Br | 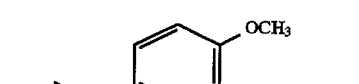 |
| 50 | 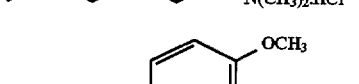 | B | Cl | COCH₃ |
| 51 | 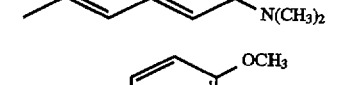 | B | Cl | COCH₃ |
| 52 | 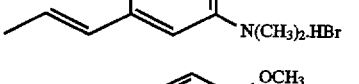 | B | Br | CON(CH₃)NH₂ |
| 53 | 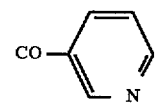 | B | Br | CON(CH₃)NH₂ |
| 54 | | B | Br | |

TABLE 1-continued
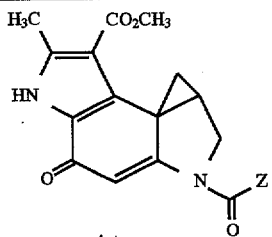
| Compound | Z | Type | X | R |
|---|---|---|---|---|
| 55 | 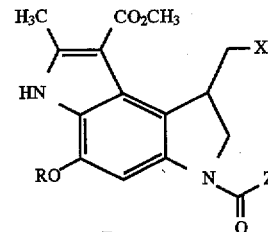 | B | Br | 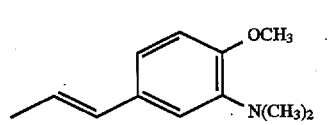 |
| 56 | 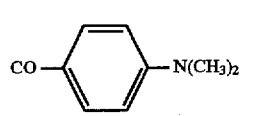 | B | Br | 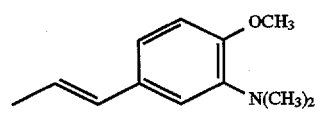 |
| 57 | 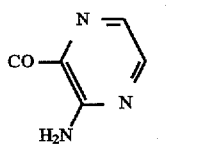 | B | Br | 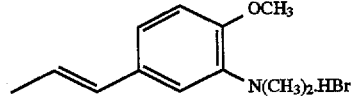 |
| 58 | 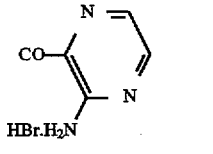 | B | Br | 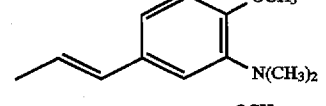 |
| 59 | 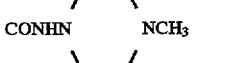 | B | Br | 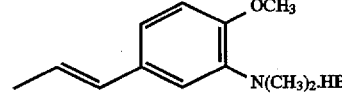 |
| 60 | 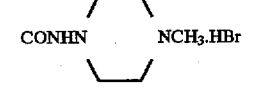 | B | Br | 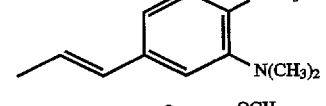 |
| 61 |  | B | Br | CONHN(CH$_3$)$_2$ |
| 62 | 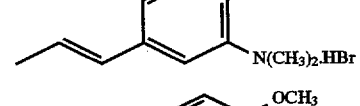 | B | Br | CONHN(CH$_3$)$_2$ |
| 63 |  | B | Br | CON(CH$_3$)NHCH$_3$ |
| 64 | 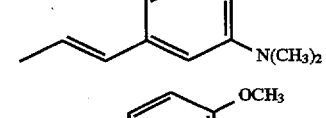 | B | Br | CON(CH$_3$)NHCH$_3$ |
| 65 |  | B | Br | 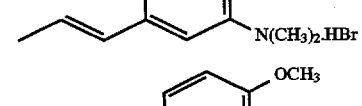 |

TABLE 1-continued

| | | | | |
|---|---|---|---|---|
| Compound | Z | Type | X | R |
| 66 | 5-(1-propenyl)-2-methoxy-N(CH₃)₂·HBr phenyl | B | Br | CO-C₆H₄-CH₂N(piperazine)NCH₃·HBr |
| 67 | 5-(1-propenyl)pyrimidin-2-yl OCH₃ | B | Br | CO-(3-pyridyl) |
| 68 | 5-(1-propenyl)pyrimidin-2-yl OCH₃ | B | Cl | CONHN(piperazine)NCH₃ |
| 69 | 5-(1-propenyl)pyrimidin-2-yl OCH₃ | B | Cl | CONHN(piperazine)NCH₃·HCl |
| 70 | 5-(1-propenyl)pyrimidin-2-yl OCH₃ | B | Br | CONHN(piperazine)NCH₃ |
| 71 | 5-(1-propenyl)pyrimidin-2-yl OCH₃ | B | Br | CONHN(piperazine)NCH₃·HCl |
| 72 | 5-(1-propenyl)pyrimidin-2-yl OCH₃ | B | Br | CONHN(piperazine)NCH₃·HBr |
| 73 | 5-(1-propenyl)pyrimidin-2-yl OCH₃ | B | Br | COCH₂SCH₂CO₂H |
| 74 | 5-(1-propenyl)pyrimidin-2-yl OCH₃ | B | Br | CON(CH₃)NH₂ |
| 75 | 5-(1-propenyl)pyrimidin-2-yl OCH₃ | B | Br | CO-C₆H₄-CH₂N(piperazine)NCH₃ |
| 76 | 5-(1-propenyl)pyrimidin-2-yl OCH₃ | B | Br | CO-C₆H₄-CH₂N(piperazine)NCH₃·HBr |

TABLE 1-continued

| Compound | Z | Type | X | R |
|---|---|---|---|---|
| 77 | (E)-CH=CH-C6H4-N(CH3)2 | B | Br | CO-(3-pyridyl) |
| 78 | (E)-CH=CH-C6H4-N(CH3)2 | B | Br | CO-N(piperazinyl)-NCH3 |
| 79 | (E)-CH=CH-C6H4-N(CH3)2·HBr | B | Br | CO-N(piperazinyl)-NCH3·HBr |
| 80 | (E)-CH=CH-C6H3(OCH3)(N(CH3)2·HCl) | B | Cl | H |
| 81 | (E)-CH=CH-C6H3(OCH3)(N(CH3)2·HBr) | B | Br | H |
| 82 | (E)-CH=CH-C6H3(OCH3)(N(CH3)2·HBr) | B | Br | COCH2-N(piperazinyl)-NCH3·2HBr |
| 83 | (E)-CH=CH-C6H3(OCH3)(N(CH3)2·HBr) | B | Br | COCH2-N(piperidinyl)-N-(piperidinyl)·2HBr |

The pharmacological activity and water-solubility of representative Compounds (I) are shown in Test Examples.

Test Example

1. Growth Inhibitory Effect Against HeLaS₃ cells

HeLaS₃ cells were suspended in MEM medium containing 10% calf serum and 2 mM glutamine to a concentration of $2.67 \times 10^4$ cells/ml. The cell suspension thus prepared was put into wells of a 24-well culture plate in an amount of 0.75 ml per well. After the cells were incubated in a $CO_2$ incubator overnight at 37° C., Compound (I) which had been appropriately diluted with a culture medium was added to each well in an amount of 0.25 ml.

The cells were further incubated in the $CO_2$ incubator for 72 hours, and the culture supernatant was removed. Then, the cells were dispersed in a solution of trypsin and EDTA and recovered. The number of cells was counted using a cell counter. The concentration ($IC_{50}$) of Compound (I) at which the growth of the cells is inhibited by 50% was calculated by comparing the number of untreated cells with the number of the cells treated with Compound (I) at known concentrations.

The result is shown in Table 2.

2. Therapeutic Effect Against Sarcoma 180 Tumor

Five male ddY-strain mice each weighing 18–20 g were used for each group as test animals, and $5 \times 10^5$ Sarcoma 180 tumor cells were implanted at the axilla subcutaneously. One day after the implantation, 0.2 ml of a physiological saline containing Compound (I) at the concentration shown in Table 2 was intravenously administered to each mouse. T/C [T: average tumor volume ($mm^3$) of the group treated with the test compound, C: average tumor volume ($mm^3$) of the control group (to which 6.2 ml of a physiological saline was intravenously administered)] was determined seven days after the implantation.

The result is shown in Table 2.

TABLE 2

| Compound | IC$_{50}$(nM) | Dose (mg/kg) | T/C |
|---|---|---|---|
| 1 | 0.42 | | |
| 3 | 110 | 1.0 | 0.36 |
| 4 | 0.70 | 0.50 | 0.35 |
| 6 | 0.90 | | |
| 8 | 170 | 2.0 | 0.26 |
| 11 | 0.92 | 1.0 | 0.17 |
| 12 | 0.28 | | |
| 14 | 90 | 1.0 | 0.31 |
| 18 | 0.19 | | |
| 20 | 94 | 0.50 | 0.20 |
| 23 | 1.6 | | |
| 25 | 1100 | 2.0 | 0.12 |
| 26 | 0.56 | | |
| 27 | 1.6 | | |
| 28 | 2.6 | | |
| 30 | 1.4 | | |
| 34 | 0.86 | | |
| 37 | 0.53 | | |
| 38 | 0.67 | | |
| 41 | 0.92 | | |
| 43 | 52 | 2.0 | 0.13 |
| 45 | 0.54 | 1.0 | 0.20 |
| 49 | 280 | 8.0 | 0.20 |
| 51 | 0.46 | 4.0 | 0.14 |
| 53 | 1.2 | 2.0 | 0.07 |
| 55 | 0.43 | 1.0 | 0.28 |
| 56 | 2.2 | 1.0 | 0.36 |
| 60 | 0.94 | 4.0 | 0.15 |
| 62 | 0.62 | 2.0 | 0.19 |
| 64 | 1.1 | 1.3 | 0.26 |
| 66 | 1.1 | 2.0 | 0.21 |
| 67 | 1.2 | 1.0 | 0.26 |
| 69 | 1.4 | 4.0 | 0.40 |
| 71 | 1.5 | 2.0 | 0.30 |
| 72 | 1.6 | 4.0 | 0.15 |
| 73 | 1.2 | 1.0 | 0.36 |
| 74 | 2.4 | 1.0 | 0.37 |
| 76 | 1.3 | 1.0 | 0.25 |
| 77 | 0.45 | 4.0 | 0.19 |
| 79 | 52 | 8.0 | 0.22 |
| 80 | 0.44 | | |
| 81 | 0.50 | | |
| 82 | 0.50 | | |
| 83 | 0.59 | | |

3. Acute Toxicity

Compound (I) was intravenously administered to ddY-strain male mice each weighing 20±1 g. MLD (minimum lethal dose) was determined by observing the mortality at 14 days after administration. The result is shown in Table 3.

TABLE 3

| Compound | MLD (mg/kg) |
|---|---|
| 3 | 1.0 |
| 4 | 0.50 |
| 8 | 4.0 |
| 11 | 1.0 |
| 14 | 0.50 |
| 20 | 0.50 |
| 25 | 4.0 |
| 43 | 4.0 |
| 45 | 1.0 |
| 49 | >8.0 |
| 51 | 4.0 |
| 53 | 2.0 |
| 55 | 1.0 |
| 56 | 1.0 |
| 60 | >8.0 |

TABLE 3-continued

| Compound | MLD (mg/kg) |
|---|---|
| 62 | 2.0 |
| 64 | 2.0 |
| 66 | 2.0 |
| 67 | 1.0 |
| 69 | 4.0 |
| 72 | 4.0 |
| 77 | 4.0 |
| 82 | 2.0 |

4. Test for Solubility in Water

A sample tube was charged with 0.7 mg of Compound (I), and 30 μl of water were added thereto at room temperature. The mixture was stirred, and the solubility in water was measured. When the compound was not dissolved, 30 μl of water was added thereto successively, and the mixture was stirred. The solubility in water was measured when the compound was dissolved. The result is shown in Table 4.

TABLE 4

| Compound | Solubility (mg/ml) |
|---|---|
| 3 | >20 |
| 8 | >20 |
| 14 | >20 |
| 17 | >20 |
| 25 | 0.2 |
| 32 | >20 |
| 40 | >20 |
| 43 | <0.5 |
| 45 | >20 |
| 49 | >20 |
| 51 | >10 |
| 55 | >18 |
| 58 | >20 |
| 60 | >20 |
| 62 | >20 |
| 64 | >15 |
| 66 | >20 |
| 69 | >10 |
| 71 | >10 |
| 72 | >10 |
| 73 | <0.1 |
| 76 | >10 |
| 79 | >20 |
| 80 | >15 |
| 81 | 2.5 |
| 82 | >10 |
| 83 | >20 |

Compounds (I) and pharmaceutically acceptable salts thereof can be used as anti-tumor compositions singly or in combination with at least one pharmaceutically acceptable auxiliary. For example, Compounds (I) or salts thereof are dissolved in a physiological saline or in an aqueous solution of glucose, lactose, mannitol, etc. to prepare a pharmaceutical composition suitable for injection. Alternatively, Compounds (I) or salts thereof are freeze-dried in a conventional manner and mixed with sodium chloride to prepare a powder injection. If necessary, the pharmaceutical composition of the present invention may contain additives which are known in the art of medical preparation, for example, pharmaceutically acceptable salts.

Although the dose of the composition of the present invention varies depending on the age, condition etc. of the patient, Compound (I) is administered to mammals including human beings at a dose of 0.01 to 60 mg/kg/day. Administration may be conducted, for example, once a day (single administration or consecutive administrations) or intermittently 1 to 3 times a week or once every 2 to 3 weeks, intravenously. If desired, intraarterial administration, intraperitoneal administration, intrathoracial administration, etc. are also possible at a similar dose and in a similar manner. Further, if desired, the composition may also be administered orally, at a similar dose and in a similar manner. Forms for oral administration include tablets, capsules, powders, granules and ampoules, which contain pharmaceutical auxiliaries well known in the art of medical preparation.

The present invention is illustrated by referring to the following Examples. The physicochemical properties of the compounds shown in the following Examples were determined with the following equipments.

| NMR | JEOL, Ltd. | FX-100 (100 MHz) |
| | | JNM-GX270 (270 MHz) |
| | | JNM-EX270 (270 MNz) |
| | Bluker | AM-400 (400 MHz) |
| MS | Hitachi Ltd. | M-80B |
| | JEOL, Ltd. | JMS-D300 |
| | | JMS-SX102 |
| IR | Japan Spectral Co., Ltd. | IR-810 |
| | HORIBA | FT200 |

In thin-layer chromatography, a silica-gel plate (Silica gel 60$F_{254}$, 0.5 mm 20×20 cm) manufactured by Merck Co. was used. As the silica gel for column chromatography, Wakogel C-200 manufactured by Wako Pure Chemical Industries, Ltd. was used.

Best Mode for Carrying Out the Invention

EXAMPLE 1

Synthesis of Compound 1

N,N-dimethylformamide (0.38 ml) was added to 4.7 mg (0.118 mmol) of 60% sodium hydride. An N,N-dimethylformamide solution (0.5 ml) containing Compound (A) prepared according to the method described in JP,A,5-178858 was added thereto, and the mixture was stirred at −20° C. for 2 hours and 20 minutes in an argon atmosphere. To the reaction mixture was added 0.5 ml of an N,N-dimethylformamide solution containing 32.1 mg (0.107 mmol) of p-nitrophenyl (E)-3-(6-methoxy-3-pyridinyl) acrylate [prepared according to the method described in J. Med. Chem., 32, 583–593 (1989)]. The mixture was stirred for 80 minutes. To the reaction mixture was added 0.01M phosphate buffer of pH 7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography [30 ml of silica gel, chloroform:methanol=100:1 to 70:1) to give 31.8 mg of Compound 1 (yield: 78%).

The physicochemical properties of Compound 1 are as follows.

$^1$H-NMR (270 MHz, CDCl$_3$)δ(ppm); 11.52( 1H, br), 8.32(1H, d,J=2.0 Hz), 7.81(1H,dd, J=2.3, 8.6 Hz), 7.77(1H, d,J=15.2 Hz), 6.77(1H, d,J=15.5 Hz), 6.77(1H,d,J=8.9 Hz), 6.74(1H,br), 4.24(1H,d,J=10.9 Hz), 4.16(1H, dd, J=10.9, 4.6 Hz), 3.98(3H, s), 3.81(3H,s), 3.55–3.61(1H,m), 2.62(3H,s), 2.40(1H, dd, J=7.4, 3.5 Hz), 1.31(1H, dd, J=4.6, 3.6 Hz)

FABMS (m/z); 420(M+H) $^+$

IR(KBr)ν(cm$^1$; 1701, 1668, 1614, 1601, 1495, 1462, 1389, 1292, 1244, 1219, 1111

EXAMPLE 2

Synthesis of Compound 2

To 21.2 mg (0.051 mmol) of Compound 1 obtained in Example 1 were added 1.27 ml of acetonitrile and 11.5 µl of 48% hydrobromic acid, and the mixture was stirred at room temperature for 30 minutes. The reaction mixture was concentrated under reduced pressure. The obtained crude product was dissolved in a mixed solvent of 1.07 ml of methylene chloride and 0.42 ml of toluene, and 29.6 mg (0.158 mmol) of p-nitrophenyl chloroformate and 21.1 µl (0.153 mmol) of triethylamine were then added thereto at −78° C. The mixture was stirred for 30 minutes. Subsequently, to the mixture was added 19.6 µl (0.179 mmol) of N-methylpiperazine, and the mixture was stirred at −78° C. to 0° C. for 20 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=9:1) to give 25 mg of Compound 2(yield: 78%).

The physicochemical properties of Compound 2 are as follows.

$^1$H-NMR (270 MHz, CDCl$_3$)δ(ppm); 9.20( 1H,brs), 8.34 (1H, d,J=2.3 Hz), 8.21(1H,brs), 7.89(1H,dd,J=8.6, 2.3 Hz), 7.79(1H, d,J=15.2 Hz), 6.82(1H, d,J=15.2 Hz), 6.81(1H, d,J=8.6 Hz), 4.49–4.60(1H,m), 4.45(1H, d,J=10.2 Hz), 4.30 (1H,dd, J=9.6, 8.9 Hz), 3.98(3H,s), 3.95(3H,s), 3.79(1H,dd, J=9.6, 9.6 Hz), 3.76(2H,br), 3.63(2H,br), 3.21(1H,dd, J=10.2, 9.9 Hz), 2.53(3H,s), 2.49(4H,br), 2.36(3H,s)

FABMS(m/z); 628, 626(M+H) $^+$

IR(KBr)ν(cm$^{-1}$); 1701, 1697, 1649, 1495, 1435, 1410, 1381, 1290, 1217, 1153, 1095

EXAMPLE 3

Synthesis of Compound 3

To 20.9 mg (0.0334 mmol) of Compound 2 obtained in Example 2 were added 0.91 ml of ethanol and 0.46 ml of methanol, and then 14.6 µl of 6.86N hydrogen chloride in ethanol was added thereto. The mixture was stirred at room temperature for 4 hours. The reaction mixture was concentrated under reduced pressure to give 22.1 mg of Compound 3.

The physicochemical properties of Compound 3 are as follows.

$^1$H-NMR(270 MHz, DMSO-d6)δ(ppm); 12.12(1H,s) , 10.70(1H,br), 8.50(1H,d,J=2.3 Hz), 7.35(1H,dd, J=8.6, 2.3 Hz), 8.10(1H,br), 7.61(1H,d,J=15.5 Hz), 7.19(1H,d,J=15.2 Hz), 6.92(1H,d,J=8.9 Hz), 4.36–4.51(4H,m), 4.12–4.18(2H, br), 3.91(3H, s), 3.85(3H, s), 3.79(1H,brd, J=8.3 Hz), 2.85 (3H, s), 2.68(3H, s)

IR(KBr)ν(cm$^{-1}$); 1714, 1695, 1657, 1651, 1435, 1414, 1219, 1173, 1095

EXAMPLE 4

Synthesis of Compound 4

To 18.3 mg (0.0436 mmol) of Compound 1 obtained in Example 1 were added 1.1 ml of acetonitrile and 9.85 µl of 48% hydrobromic acid. The mixture was stirred at room temperature for 35 minutes. The reaction mixture was concentrated under reduced pressure. The obtained crude product was dissolved in a mixed solvent of 0.92 ml of methylene chloride and 0.37 ml of toluene, and 10.4 µl (0.135 mmol) of methyl chloroformate and 18.2 µl (0.131 mmol) of triethylamine were added thereto at −78° C. The mixture was stirred at −78° C. to room temperature for 40 minutes. To the reaction mixture was added a saturated aqueous solution of sodium hydrogen carbonate, and the resulting mixture was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=9:1) to give 22 mg of Compound 4(yield: 90%).

The physicochemical properties of Compound 4 are as follows.

$^1$H-NMR(270 MHz, CDCl$_3$)δ(ppm); 8.79(1H,s), 8.40 (1H,brs), 8.34(1H,d,J=2.3 Hz), 7.88(1H,dd,J=8.6, 2.3 Hz), 7.79(1H,d,J=15.2 Hz), 6.82(1H,d,J=15.2 Hz), 6.80(1H,d,J= 8.6 Hz), 4.50–4.60(1H,m), 4.46(1H,d,J=9.9 Hz), 4.30(1H, dd,J=9.2, 9.2 Hz), 3.98(3H,s), 3.96(3H,s), 3.94(3H,s), 3.80 (1H,dd,J=9.6, 2.6 Hz), 3.22(1H,dd,J=10.2, 9.9 Hz), 2.68(3H, s)

FABMS(m/z);560, 558(M+H) $^+$

IR(KBr)ν(cm$^{-1}$); 1768, 1697, 1647, 1498, 1437, 1416, 1408, 1290, 1246, 1215, 1196

EXAMPLE 5

Synthesis of Compound 5

To 38.9 mg (0.0925 mmol) of Compound 1 obtained in Example 1 were added 2 ml of acetonitrile and 21 µl of 48% hydrobromic acid, and the mixture was stirred at room temperature for 30 minutes. The reaction mixture was concentrated under reduced pressure. The obtained crude product was dissolved in a mixed solvent of 1.95 ml of methylene chloride and 0.78 ml of toluene, and 57.8 mg (0.287 mmol) of p-nitrophenyl chloroformate and 52 µl (0.37 mmol) of triethylamine were added thereto at −78° C. The mixture was stirred for 20 minutes. Subsequently, 54.5 mg (0.324 mmol) of glycine tert-butyl ester hydrochloride and 45 µl (0.324 mmol) of triethylamine were added thereto. The mixture was stirred at −78° C. to room temperature for 16 hours. To the reaction mixture were further added 27.3 mg (0.162 mmol) of glycine tert-butyl ester hydrochloride and 22.5 µl (0.162 mmol) triethylamine, and the mixture was stirred for 3 hours. To the reaction mixture was added a 0.01M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=20:1) to give 62.3 mg of a tert-butyl ester of Compound 5.

To 46.8 mg of the tert-butyl ester of Compound 5 were added 5 ml of 1,2-dichloroethane and 0.22 ml of trifluoroacetic acid, and the mixture was stirred at 80° C. for 2 hours and 20 minutes. To the reaction mixture was added water, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by thin-layer chromatography (chloroform:methanol=2:1) to give 14.6 mg of Compound 5(yield: 34%).

The physicochemical properties of Compound 5 are as follows.

$^1$H-NMR (270 MHz, CD$_3$OD)δ(ppm); 8.31(1H, d,J=2.0 Hz), 8.10(1H, dd,J=8.9, 2.6 Hz), 8.09(1H,s), 7.63(1H,d,J= 15.5 Hz ), 7.03(1H,d,J=15.2 Hz), 6.85(1H,d,J=8.9 Hz), 4.42–4.70(2H,m), 4.28–4.40(1H,m), 3.95(3H,s), 3.91(3H,s), 3.81–3.87(1H,m), 3.79(2H,s), 3.55–3.63(1H,m), 2.67(3H,s)

FABMS(m/z); 603, 601(M+H) $^+$

IR(KBr)ν(cm$^{-1}$); 1701, 1697, 1686, 1601, 1497, 1439, 1419, 1211, 1190, 1138

EXAMPLE 6

Synthesis of Compound 6

To 970 mg (8.47 mmol) of 2-chloropyrimidine were added 7 ml of methanol and 3.4 g (16.94 mmol) of 28 wt % of sodium methylate in methanol, and the mixture was stirred at room temperature for 30 minutes.

Water was added to the reaction mixture, and the solution was extracted with chloroform. The chloroform layer was washed with a saturated aqueous solution of sodium chloride, dried over anhydrous sodium sulfate, and concentrated under reduced pressure. To 2-methoxypyrimidine obtained were added 14 ml of trifluoroacetic acid, 3 ml of trifluoroacetic anhydride and 3.96 g (16.94 mmol) of N-iodosuccinimide, and the mixture was stirred under reflux (bath temperature: 80° C.) for 11 hours. Water was added to the reaction mixture, and the solution was extracted with chloroform. The chloroform layer was washed with a saturated aqueous solution of sodium hydrogen carbonate, an aqueous solution of 5% sodium thiosulfate and a saturated aqueous solution of sodium chloride, dried over anhydrous sodium sulfate, and concentrated under reduced pressure. The obtained crude product was purified by silica-gel column chromatography (250 ml of silica gel, hexane:ethyl acetate=3:1) to give 523 mg (2.22 mmol) of 2-methoxy-5-iodopyrimidine (yield: 26%).

2-Methoxy-5-iodopyrimidine (1.736 g, 7.36 mmol) was dissolved in 36 ml of N,N-dimethylformamide, and 99 mg of palladium acetate, 2.54 g (18.4 mmol) of potassium carbonate, 2.05 g (7.36 mmol) of tetrabutylammonium chloride and 3.168 g (36.8 mmol) of methyl acrylate were added thereto. The mixture was stirred in an argon atmosphere at 80° C. for 1 hour. Water was added to the reaction mixture, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (250 ml of silica gel, hexane:ethyl acetate=2:1 to 1:1) to give 1.26 g (6.49 mmol) of methyl (E)-3-(2-methoxy-5-pyrimidinyl)acrylate (yield: 88%).

To 1.26 g of methyl (E)-3-(2-methoxy-5-pyrimidinyl) acrylate were added 40 ml of methanol and 3.25 ml of a 4N potassium hydroxide aqueous solution, and the mixture was stirred at 50° C. for 2 hours. To the reaction mixture was added 0.5N hydrochloric acid, and the solution was extracted with ethyl acetate. The ethyl acetate layer was washed with a saturated aqueous solution of sodium chloride, dried over anhydrous sodium sulfate, and then concentrated under reduced pressure to give 1.12 g (6.22 mmol) of (E)-3-(2-methoxy-5-pyrimidinyl)acrylic acid.

N,N-dimethylformamide (0.3 ml) was added to 3.7 mg (0.0936 mmol) of 60% sodium hydride, and 0.4 ml of an N,N-dimethylformamide solution containing 20 mg of Compound (A) were added thereto. The mixture was stirred in an argon atmosphere at −20° C. for 2.5 hours. To the reaction mixture was added 0.4 ml of an N,N-dimethylformamide solution containing 25.8 mg (0.86 mmol) of p-nitrophenyl (E)-3-(2-methoxy-5-pyrimidinyl)acrylate, and the resulting mixture was stirred for 110 minutes. To the reaction mixture was added a 0.01M phosphate buffer of pH7, and the resulting mixture was extracted with ethyl acetate and with chloroform. The ethyl acetate layer and the chloroform layer were separately washed with a saturated aqueous solution of sodium chloride, and dried over anhydrous sodium sulfate. The combined organic layer was concentrated under reduced pressure. The obtained crude product was purified by silica-gel column chromatography (30 ml of silica gel, chloroform:methanol=100:1 to 70:1) to give 24.1 mg of Compound 6(yield: 74%).

The physicochemical properties of Compound 6 are as follows.

$^1$H-NMR(270 MHz, DMSO-d$_6$)δ(ppm); 12.39(1H,brs), 9.04(2H,s), 7.65(1H,d,J=15.8 Hz), 7.21(1H,d,J=15.8 Hz), 6.91(1H,br), 4.38(1H,d,J=10.9 Hz), 4.21(1H,dd,J=10.9, 4.6 Hz), 3.97(3H,s), 3.74(3H,s), 3.46–3.52(1H,m), 2.47(3H,s), 2.11(1H,dd,J=7.6, 3.0 Hz), 1.32(1H,dd,J=4.0, 4.0 Hz)

FABMS (m/z); 423(M+3)$^+$,421(M+H)$^+$

IR(KBr)ν(cm$^{-1}$); 1701, 1676, 1624, 1618, 1595, 1477, 1400, 1340, 1250, 1111

EXAMPLE 7

Synthesis of Compound 7

To 20.9 mg (0.0497 mmol) of Compound 6 obtained in Example 6 were added 1.25 ml of acetonitrile and 17.7 μl of 48% hydrobromic acid, and the mixture was stirred at room temperature for 50 minutes. The reaction mixture was concentrated under reduced pressure. The obtained crude product was dissolved in a mixed solvent of 1.05 ml of methylene chloride and 0.41 ml of toluene, and 31 mg (0.154 mmol) of p-nitrophenyl chloroformate and 20.8 μl (0.149 mmol) of triethylamine were added thereto at 78° C. The mixture was stirred for 30 minutes, and 31 mg (0.154 mmol) of p-nitrophenyl chloroformate and 20.8 μ(0.149 mmol) of triethylamine were further added thereto at −20° C. The solution was stirred for 20 minutes. Subsequently, 38.6 μl (0.348 mmol) of N-methylpiperazine was added to the solution, and the mixture was stirred at −20° C. to 0° C. for 60 minutes. A saturated aqueous solution of sodium hydrogen carbonate was added to the reaction mixture, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=10:1) to give 20.4 mg of Compound 7(yield: 65%).

The physicochemical properties of Compound 7 are as follows.

$^1$H-NMR(270 MHz, CDCl$_3$)δ(ppm); 9.01(1H,s), 8.75 (2H,s), 8.21(1H,s), 7.71(1H,d,J=15.5 Hz), 6.93(1H,d,J=15.5 Hz), 4.53–4.63(1H,m), 4.45(1H,d,J=10.2 Hz), 4.31(1H,dd, J=9.6, 9.6 Hz), 4.07(3H,s), 3.95(3H,s), 3.80(1H,dd,J=7.3, 2.6 Hz), 3.74(2H,br), 3.64(2H,br), 3.23(1H,dd,J=10.2, 9.9 Hz), 2.61(3H,s), 2.50(4H,brs), 2.37(3H,s)

FABMS(m/z); 629, 627(M+H)$^+$

IR(KBr)ν(cm$^{-1}$); 1714, 1701, 1653, 1473, 1435, 1412, 1338, 1219, 1153, 1095

EXAMPLE 8

Synthesis of Compound 8

To 20.4 mg (0.0325 mmol) of Compound 7 obtained in Example 7 were added 1.33 ml of ethanol and 0.67 ml of methanol, and then 19 μl of 6.86N hydrogen chloride in ethanol was added thereto. The mixture was stirred at room temperature for 3.5 hours. The reaction mixture was concentrated under reduced pressure to give 20.2 mg of Compound 8.

The physicochemical properties of Compound 8 are as follows.

$^1$H-NMR (270 MHz, DMSO-d$_6$)δ(ppm); 12.06(1H,s), 10.44(1H,br), 9.08(2H,s), 8.11(1H,s), 7.59(1H,d,J=15.8 Hz), 7.36(1H,d,J=15.8 Hz), 4.40–4.49(3H,m), 4.10–4.24 (1H,br), 3.98(3H,s), 3.85(3H,s), 3.76–3.84(1H,m), 2.86(3H, s), 2.68(3H,s)

IR(KBr)ν(cm$^{-1}$); 1705, 1701, 1659, 1477, 1433, 1412, 1336, 1215, 1186, 1095

EXAMPLE 9

Synthesis of Compound 9

To 18.2 mg (0.0433 mmol) of Compound 6 obtained in Example 6 were added 1.1 ml of acetonitrile and 19.6 μl of 48% hydrobromic acid, and the mixture was stirred at room temperature for 2 hours. The reaction mixture was concentrated under reduced pressure. The obtained crude product was dissolved in a mixed solvent of 0.91 ml of methylene chloride and 0.36 ml of toluene. Then, 20.6 μl (0.267 mmol) of methyl chloroformate and 36.1 μl (0.259 mmol) of triethylamine were added thereto at −78° C. The mixture was stirred at −78° C. to room temperature for 2 hours and 40 minutes. To the reaction mixture was added a saturated aqueous solution of sodium hydrogen carbonate, and the resulting mixture was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=20:1) to give 15.3 mg of Compound 9(yield: 63%).

The physicochemical properties of Compound 9 are as follows.

$^1$H-NMR(270 MHz, CDCl$_3$)δ(ppm); 8.82(1H,s), 8.74 (2H,s), 8.39(1H,brs), 7.71(1H,d,J=15.5 Hz), 6.92(1H,d,J= 15.2 Hz), 4.51–4.65(1H,m), 4.46(1H, d,J=9.9 Hz), 4.32(1H, dd,J=9.9, 8.6 Hz), 4.08(3H,s), 3.96(3H,s), 3.94(3H,s), 3.80 (1H,dd, J=9.9, 2.3 Hz), 3.25(1H,dd,J=9.9, 9.6 Hz), 2.70(3H, s)

FABMS (m/z); 561, 559(M+H)$^+$

IR(KBr)ν(cm$^{-1}$); 1763, 1697, 1653, 1593, 1475, 1414, 1338, 1271, 1217, 1095

EXAMPLE 10

Synthesis of Compound 10

To 28.8 mg of Compound 6 obtained in Example 6 were added 1.5 ml of acetonitrile and 23.2 μl of 48% hydrobromic acid, and the mixture was stirred at room temperature for 30 minutes. The reaction mixture was concentrated under reduced pressure. The obtained crude product was dissolved in a mixed solvent of 1.44 ml of methylene chloride and 0.58 ml of toluene, and 42.8 mg (0.212 mmol) of p-nitrophenyl chloroformate and 47.7 μl (0.343 mmol) of triethylamine were added thereto at –78° C. The mixture was stirred for 40 minutes. Then, to the solution were added 40.4 mg (0.240 mmol) of glycine tert-butyl ester hydrochloride and 33.4 μl (0.240 mmol) of triethylamine, and the mixture was stirred at –78° C. to room temperature for 3 hours. To the reaction mixture was added a 0.01M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=9:1) to give 47.7 mg of a tert-butyl ester of Compound 6.

To 35.7 mg of the tert-butyl ester of Compound 6 were added 3.5 ml of 1,2-dichloroethane and 0.168 ml of trifluoroacetic acid, and the mixture was stirred at 80° C. for 2 hours and 10 minutes. Water was added to this reaction mixture, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by thin-layer chromatography (chloroform:methanol=3:1) to give 18 9 mg (0.0314 mmol) of Compound 10 (yield: 60%).

The physicochemical properties of Compound 10 are as follows.

$^1$H-NMR(270 MHz, acetone-$d_6$+trifluoroacetic acid-d) δ(ppm); 8.97(2H,s), 8.20(1H,brs), 7.65(1H,d,J=15.5 Hz), 7.37(1H,d,J=15.5 Hz), 4.51(1H,d,J=9.6 Hz), 4.48–4.60(1H, br), 4.34–4.45(1H,m), 4.00(3H,s), 3.99(2H,s), 3.84(3H,s), 3.74–3.80(1H,m), 3.35(1H,dd,J=9.9, 6.9 Hz), 2.61(3H,s)

FABMS(m/z); 604, 602(M+H) $^+$

IR(KBr)ν(cm$^{-1}$); 1684, 1655, 1595, 1479, 1435, 1414, 1275, 1211, 1138

EXAMPLE 11

Synthesis of Compound 11

To 14.3 mg (0.0340 mmol) of Compound 6 obtained in Example 6 were added 1.43 ml of acetonitrile and 11.5 μl of 48% hydrobromic acid, and the mixture was stirred at room temperature for 40 minutes. The reaction mixture was concentrated under reduced pressure. The obtained crude product was dissolved in a mixed solvent of 1.45 ml of methylene chloride and 0.57 ml of toluene, and 9.94 μl (0.105 mmol) of acetic anhydride and 13.3 mg (0.109 mmol) of 4-dimethylaminopyridine were added thereto. The mixture was stirred for 1.5 hours. To the reaction mixture was added a 0.01M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=9:1) to give 17 mg of Compound 11(yield: 91%).

The physicochemical properties of Compound 11 are as follows.

$^1$H-NMR (270 MHz, CDCl$_3$)δ(ppm); 8.74(2H,s), 8.66 (1H,brs), 8.27(1H,s), 7.70(1H,d,J=15.5 Hz), 6.92(1H,d,J= 15.5 Hz), 4.53–4.65(1H,m), 4.45(1H,d,J=9.6 Hz), 4.32(1H, dd,J=10.2, 8.9 Hz), 4.08(3H,s), 3.96(3H,s), 3.82(1H,brd,J= 9.2 Hz), 3.25(1H,dd,J=9.9, 9.9 Hz), 2.67(3H,s), 2.39(3H,s)

FABMS (m/z); 545, 543(M+H) $^+$

IR(KBr)ν(cm$^{-1}$); 1761, 1697, 1655, 1593, 1475, 1435, 1412, 1338, 1201, 1188, 1088

EXAMPLE 12

Synthesis of Compound 12

To 2 g of 3,6-dichloropyridazine were added 60 ml of acetone and 20.12 g (268.4 mmol) of sodium iodide, and the mixture was stirred under reflux (bath temperature: 70° C.) for 2 hours. Water was added to the reaction mixture, and the solution was extracted with ethyl acetate. The ethyl acetate layer was washed with a saturated aqueous solution of sodium thiosulfate and with a saturated aqueous solution of sodium chloride, dried over anhydrous sodium sulfate, and then concentrated under reduced pressure to give 2.73 g (8.23 mmol) of 3,6-diiodopyridazine (yield: 61%).

To 2.73 g (8.23 mmol) of 3,6-diiodopyridazine were added 80 ml of methanol and 3.17 g (16.46 mmol) of 28 wt % of sodium methylate in methanol, and the mixture was stirred at room temperature for 13 hours. Water was added to the reaction mixture, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (200 ml of silica gel, hexane:ethyl acetate=8:1) to give 1.661 g (7.04 mmol) of 3-methoxy-6-iodopyridazine (yield: 86%).

3-Methoxy-6-iodopyridazine (1.661 g, 7.04 mmol) was dissolved in 34 ml of N,N-dimethylformamide, and 99 mg of palladium acetate, 1.06 g (7.67 mmol) of potassium carbonate, 1.96 g (7.05 mmol) of tetrabutylammonium chloride and 12.12 g (141 mmol) of methyl acrylate were added thereto. The mixture was stirred in an argon atmosphere at 80° C. for 4.5 hours. Water was added to the reaction mixture, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (300 ml of silica gel, hexane:ethyl acetate= 3:1 to 2:1) to give 818 mg (4.21 mmol) of methyl (E)-3-(3-methoxy-6-pyridazinyl) acrylate (yield: 60%).

To 818 mg (4.21 mmol) of methyl (E)-3-(3-methoxy-6-pyridazinyl) acrylate were added 25 ml of methanol and 4.22 ml of 4N aqueous potassium hydroxide, and the mixture was stirred at room temperature for 8 hours. To the reaction mixture was added 0.5N hydrochloric acid, and the solution was extracted with ethyl acetate and with chloroform. The ethyl acetate layer and the chloroform layer were separately washed with a saturated aqueous solution of sodium chloride, dried together over anhydrous sodium chloride. The combined organic layer was concentrated under reduced pressure to give 668 mg (3.71 mmol) of (E)-3-(3-methoxy-6-pyridazinyl)acrylic acid (yield: 88%).

To 3.7 mg (0.0936 mmol) of 60% sodium hydride was added 0.4 ml of N,N-dimethylformamide, and then 0.4 ml of an N,N-dimethylformamide solution containing 20 mg of Compound (A) was added thereto. The mixture was stirred in an argon atmosphere at –20° C. for 2.5 hours. To the reaction mixture was added 0.41 ml of an N,N-dimethylformamide solution containing 25.8 mg (0.86 mmol) of p-nitrophenyl (E)-3-(3-methoxy-6-pyridazinyl) acrylate, and the mixture was stirred for 80 minutes. To the reaction mixture was added a 0.01M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol= 100:1 to 70:1) to give 24 ml of Compound 12(yield: 73%).

The physicochemical properties of Compound 12 are as follows.

$^1$H-NMR(270 MHz, CDCl$_3$)δ(ppm); 11.48(1H,brs), 7.84 (1H,d,J=15.2 Hz), 7.52(1H,d,J=9.2 Hz), 7.44(1H,d,J=15.2 Hz), 7.00(1H,d,J=9.2 Hz), 6.93(1H,br), 4.29(1H,d,J=10.9 Hz), 4.20(1H,dd,J=10.9, 4.6 Hz), 4.19(3H,s), 3.81(3H,s), 3.54–3.66(1H,m), 2.62(3H,s), 2.39(1H,dd,J=7.6, 3.6 Hz), 1.31(1H,dd,J=5.0, 3.6 Hz)

FABMS(m/z); 423(M+3) $^+$, 421(M+H) $^+$

IR(KBr)ν(cm$^{-1}$); 1701, 1610, 1466, 1411, 1396, 1294, 1248, 1217, 1109, 1072

Compound 13

Synthesis of Compound 13

To 20.3 mg (0.0482 mmol) of Compound 12 obtained in Example 12 were added 1.23 ml of acetonitrile and 17.2 μl of 48% hydrobromic acid, and the mixture was stirred at room temperature for 30 minutes. The reaction mixture was concentrated under reduced pressure. The obtained crude product was dissolved in a mixed solvent of 1.02 ml of methylene chloride and 0.40 ml of toluene, and 30.1 mg (0.149 mmol) of p-nitrophenyl chloroformate and 20.2 μl (0.145 mmol) of triethylamine were added thereto at −78° C. The mixture was stirred for 50 minutes. Then, 30.1 mg (0.149 mmol) of p-nitrophenyl chloroformate and 20.2 μl (0.145 mmol) of triethylamine were further added thereto at −20° C. The solution was stirred for 60 minutes. Subsequently, to the solution were added 37.4 μl (0.337 mmol) of N-methylpiperazine, and the mixture was stirred at −20° C. to 0° C. for 2 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with an aqueous solution of sodium chloride, dried over anhydrous sodium sulfate, and then concentrated under reduced pressure. The obtained crude product was purified by thin-layer chromatography (chloroform:methanol=10:1) to give 21.1 mg of Compound 13(yield: 70%).

The physicochemical properties of Compound 13 are as follows.

$^1$H-NMR(270 MHz, CDCl$_3$)δ(ppm); 9.15(1H,brs), 8.24 (1H,s), 7.84(1H,d,J=15.2 Hz), 7.57(1H,d,J=15.2 Hz), 7.54 (1H, d,J=8.9 Hz), 7.01(1H,d,J=8.9 Hz), 4.53–4.60(1H,m), 4.52(1H,d,J=9.9 Hz), 4.33(1H,dd,J=9.6, 9.6 Hz), 4.20(3H, s), 3.95(3H,s), 3.79(1H,dd,J=10.2, 2.6 Hz), 3.75(2H,br), 3.61 (2H,br), 3.21(1H,dd,J=10.2, 9.9 Hz), 2.57(3H,s), 2.49 (4H,br), 2.36(3H,s)

FABMS (m/z); 627, 629(M+H) $^+$

IR(KBr)ν(cm$^{-1}$); 1714, 1705, 1699, 1653, 1466, 1412, 1294, 1217, 1153, 1093, 1005

EXAMPLE 14

Synthesis of Compound 14

To 21.1 mg (0.0336 mmol) of Compound 13 obtained in Example 13 were added 1.38 ml of ethanol and 0.69 ml of methanol, and 19.6 μl of 6.86N hydrogen chloride in ethanol was added thereto. The mixture was stirred at room temperature for 3.5 hours. The reaction mixture was concentrated under reduced pressure to give 23.3 mg of Compound 14.

The physicochemical properties of Compound 14 are as follows.

$^1$H-NMR(270 MHz,DMSO-d$_6$)δ(ppm); 12.12(1H,s), 10.54(1H,br), 8.31(1H,d,J=8.9 Hz), 7.74(1H,d,J=15.2 Hz), 7.54(1H,d,J=15.2 Hz), 7.34(1H,d,J=8.6 Hz), 4.34–4.60(4H, m), 4.02–4.24(1H,br), 4.09(3H,s), 3.85(3H,s), 3.76–3.82 (1H,m), 2.85(3H,br), 2.69(3H,s)

IR(KBr)ν(cm$^{-1}$); 1716, 1705, 1699, 1417, 1435, 1414, 1252, 1219, 1093

EXAMPLE 15

Synthesis of Compound 15

To 3 g (31.5 mmol) of 3-hydroxypyridine were added 80 ml of methanol, 4.72 g (31.5 mmol) of sodium iodide and 1.26 g (31.5 mmol) of sodium hydroxide, and then 58.5 g of a 4% sodium hypochlorite aqueous solution was added thereto dropwise at 0° C. in a period of 100 minutes. The mixture was then stirred for 3 hours. To the reaction mixture were added 10 ml of a 5% sodium thiosulfate aqueous solution and 0.1N hydrochloric acid. The mixture was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (350 ml of silica gel, hexane:ethyl acetate=4:1 to 1:1) to give 2.38 g of 3-hydroxy-6-iodopyridine (yield: 34%).

To 647 mg (16.2 mmol) of 60% sodium hydride was added 20 ml of N,N-dimethylformamide, and then 20 ml of an N,N-dimethylformamide solution containing 2.38 g (10.8 mmol) of 3-hydroxy-6-iodopyridine was added thereto. The mixture was stirred in an argon atmosphere at room temperature for 2 hours. To the reaction mixture were added 2.14 g (15.12 mmol) of methyl iodide, and the mixture was stirred for 1 hour. To the reaction mixture was added a 0.01M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, hexane:ethyl acetate=5:1 to 4:1) to give 2.57 g of 3-methoxy-6-iodopyridine (yield: 100%).

3-Methoxy-6-iodopyridine (500 mg, 2.13 mmol) was dissolved in 6 ml of N,N-dimethylformamide, and 29 mg of palladium acetate, 736 mg (5.33 mmol) of potassium carbonate, 592 mg (2.13 mmol) of tetra-n-butylammonium chloride and 917 mg (10.65 mmol) of methyl acrylate were added thereto. The mixture was stirred at 120° C. for 12 hours in a sealed tube. To the reaction mixture was added a 0.01M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (200 ml of silica gel, hexane:ethyl acetate=4:1 to 3:1) to give 168 mg (0.87 mmol) of methyl (E)-3-(3-methoxy-6-pyridyl) acrylate (yield: 41%).

To 429 mg (2.22 mmol) of methyl (E)-3-(3-methoxy-6-pyridyl)acrylate were added 12 ml of methanol and 1.11 ml of a 4N potassium hydroxide aqueous solution, and the mixture was stirred at room temperature for 20 hours. To the reaction mixture was added 1N hydrochloric acid, and the solution was extracted with ethyl acetate and with chloroform. The ethyl acetate layer and the chloroform layer were separately washed with a saturated aqueous solution of sodium chloride. The combined organic layer was dried over anhydrous sodium sulfate, and concentrated under reduced pressure to give 277 mg (1.55 mmol) of (E)-3-(3-methoxy-6-pyridyl)acrylic acid (yield: 70%).

To 3.7.mg (0.0936 mmol) of 60% sodium hydride was added 0.3 ml of N,N-dimethylformamide, and then 0.4 ml of an N,N-dimethylformamide solution containing 20 mg of Compound (A) was added thereto. The mixture was stirred in an argon atmosphere at −20° C. for 2 hours and 20 minutes. To the reaction mixture was added 0.4 ml of an N,N-dimethylformamide solution containing 25.8 mg (0.86 mmol) of p-nitrophenyl (E)-3-(3-methoxy-6-pyridyl) acrylate, and the mixture was stirred for 1.5 hours. To the reaction mixture was added a 0.01M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol= 100:1 to 50:1) to give 27.1 mg of Compound 15(yield: 83%).

The physicochemical properties of Compound 15 are as follows.

$^1$H-NMR (270 MHz, CDCl$_3$)δ(ppm); 11.80(1H,br), 8.23 (1H,d,J=15.2 Hz), 8.22(1H,dd, J=4.1, 1.5 Hz), 7.46(1H,d, J=15.2 Hz), 7.21–7.30(2H,m), 6.92(1H,br), 4.31(1H,d,J= 10.9 Hz), 4.20(1H,dd, J=10.6, 4.6 Hz), 3.90(3H,s), 3.81(3H, s), 3.55–3.62(1H,m), 2.62(3H,s), 2.36(1H,dd, J=7.6, 3.3 Hz), 1.29(1H,dd,J=4.6, 3.6 Hz)

FABMS (m/z); 422(M+3)$^+$, 420(M+H) $^+$

IR(KBr)ν(cm$^{-1}$); 1701, 1672, 1618, 1578, 1450, 1390, 1296, 1252, 1217, 1113

EXAMPLE 16

Synthesis of Compound 16

To 17.7 mg (0.0422 mmol) of Compound 15 obtained in Example 15 were added 1.06 ml of acetonitrile and 9.6 µl of 48% hydrobromic acid, and the mixture was stirred at room temperature for 30 minutes. The reaction mixture was concentrated under reduced pressure. The obtained crude product was dissolved in a mixed solvent of 0.89 ml of methylene chloride and 0.35 ml of toluene, and 24.7 mg (0.131 mmol) of p-nitrophenyl chloroformate and 17.6 µl (0.127 mmol) of triethylamine were added thereto at −78° C. The mixture was stirred for 50 minutes. Subsequently, to the solution was added 16.4 µl (0.148 mmol) of N-methylpiperazine, and the mixture was stirred at −78° C. to 0° C. for 30 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=9:1) to give 15.2 mg of Compound 16(yield: 58%).

The physicochemical properties of Compound 16 are as follows.

$^1$H-NMR(270 MHz, CDCl$_3$)δ(ppm); 9.47(1H,brs), 8.28 (1H,d,J=15.2 Hz), 8.27(1H,dd,J=4.0, 1.3 Hz), 7.55(1H,d,J= 14.9 Hz), 7.21–7.30(2H,m), 4.54(1H,br), 4.52(1H, d,J=9.6 Hz), 4.33(1H,dd, J=9.9, 9.2 Hz), 3.93(3H,s), 3.89(3H,s), 3.76(1H,dd,J=9.9, 2.6 Hz), 3.74(2H,br), 3.60(2H,br), 3.21 (1H,dd,J=9.9, 9.9 Hz), 2.51(3H,s), 2.46(4H,br), 2.34(3H,s)

FABMS(m/z); 628, 626(M+H) $^+$

IR(KBr)ν(cm$^{-1}$); 1722, 1701, 1697, 1433, 1408, 1292, 1259, 1217, 1153, 1093

EXAMPLE 17

Synthesis of Compound 17

To 14.4 mg (0.0230 mmol) of Compound 16 obtained in Example 16 were added 0.55 ml of ethanol and 0.28 ml of methanol, and then 10.1 µl of 6.86N hydrogen chloride in ethanol was added thereto. The mixture was stirred at room temperature for 3 hours. The reaction mixture was concentrated under reduced pressure to give 16 mg of Compound 17.

The physicochemical properties of Compound 17 are as follows.

$^1$H-NMR (270 MHz, DMSO-d$_6$)δ(ppm); 12.15( 1H,s), 10.75(1H,br), 8.28(1H,d,J=3.6 Hz), 8.11(1H,s), 7.96(1H,d, J=15.2 Hz), 7.62(1H,d,J=8.6 Hz), 7.54(1H,d,J=15.5 Hz), 7.45–7.50(1H,m), 4.30–4.58(4H,m), 4.08–4.24(1H,br), 3.94 (3H,s), 3.85(3H,s), 3.81(1H,br), 2.85(3H,br), 2.69(3H,s)

IR(KBr)ν(cm$^{-1}$); 1722, 1699, 1655, 1614, 1437, 1416, 1255, 1219

EXAMPLE 18

Synthesis of Compound 18

To 9.3 mg (0.23 mmol) of 60% sodium hydride was added 0.3 ml of N,N-dimethylformamide, and then 1 ml of an N,N-dimethylformamide solution containing 50 mg (0.194 mmol) of compound (A) was added thereto. The mixture was stirred in an argon atmosphere at −20° C. for 3 hours. To the reaction mixture was added 1 ml of an N,N-dimethylformamide solution containing 70 mg (0.23 mol) of p-nitrophenyl 4-methoxyphenoxyacetate, and the mixture was stirred at from −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=100:1) to give 71 mg of Compound 18(yield: 73%).

The physicochemical properties of Compound 18 are as follows.

$^1$H-NMR(400 MHz, CDCl$_3$)δ(ppm); 10.65(1H,br), 7.25 (1H,br), 6.89(2H,d,J=9.2 Hz), 6.83(2H,d,J=9.2 Hz), 4.73 (2H,s), 4.20( 1H,br d,J=10.6 Hz ), 4.11( 1H,m), 3.81(3H,s), 3.76(3H,s), 3.56(1H,m), 2.60(3H,s), 2.31(1H,dd,J=7.5, 3.4 Hz), 1.17(1H,m)

IR(KBr)ν(cm$^{-1}$); 1701, 1606, 1507, 1409, 1217, 1109, 1027

SIMS (m/z); 423(M+H) $^+$

EXAMPLE 19

Synthesis of Compound 19

Compound 18(20 mg, 0.047 mmol) obtained in Example 18 was dissolved in a mixed solvent of 1 ml of N,N-dimethylformamide and 1 ml of acetonitrile, and 1 ml of 48% hydrobromic acid was added thereto. The mixture was stirred at room temperature for 1 hour. To the reaction mixture was added 1N hydrobromic acid, and the solution was extracted with chloroform. The chloroform layer was dried over anhydrous sodium sulfate, and concentrated under reduced pressure. The resulting crude product was dissolved in 1 ml of methylene chloride, and 29 mg (0.144 mmol) of p-nitrophenyl chloroformate and then 0.020 ml (0.144 mmol) of triethylamine were added thereto at −78° C. The mixture was stirred for 1 hour. To the reaction mixture was added 0.019 ml (0.17 mmol) of N-methylpiperazine, and the mixture was stirred at −78° C. to 0° C. for 2 hours. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol= 30:1) to give 12 mg of Compound 19(yield: 41%).

The physicochemical properties of Compound 19 are as follows.

$^1$H-NMR(400 MHz, CDCl$_3$)δ(ppm); 8.75(1H,br), 8.10 (1H,br), 6.97(2H,d,J=9.1 Hz), 6.84(2H,d,J=9.1 Hz), 4.78 (2H,s), 4.54(1H,m), 4.41(1H,d,J=11.0 Hz), 4.19(1H,dd,J= 10.2, 8.5 Hz), 3.94(3H,s), 3.77(1H,br), 3.76(2H,br), 3.76 (3H,s), 3.62(2H,br), 3.20(1H,dd,J=10.0, 10.0 Hz), 2.68(3H, s), 2.50(4H,br), 2.37(3H,s)

IR(KBr)ν(cm$^{-1}$); 1688, 1589, 1506, 1412, 1292, 1216, 1149, 1096, 1004

SIMS(m/z); 631, 629(M+H) $^+$

EXAMPLE 20

Synthesis of Compound 20

To 11 mg (0.017 mmol) of Compound 19 obtained in Example 19 were added 0.5 ml of methanol and 0.5 ml of ethanol, and then 0.005 ml of 5.3N hydrogen chloride in ethanol was added thereto. The mixture was stirred at 0° C. for 2 hours. The reaction mixture was concentrated under reduced pressure to give 13 mg of Compound 20.

The physicochemical properties of Compound 20 are as follows.

$^1$H-NMR (400 MHz, DMSO-d$_6$)δ(ppm); 12.08(1H,br), 10.56(1H,br), 7.92(1H,s), 6.93(2H,d,J=9.1 Hz), 6.84(2H,d, J=9.2 Hz), 4.92(1H,d,J=15.2 Hz), 4.83(1H,d,J=15.2 Hz), 4.49(1H,br), 4.35(2H,br), 4.30(1H,dd,J=10.5, 10.5 Hz), 4.19 (1H,br d,J=11.2 Hz), 3.85(3H,s), 3.79(1H,dd,J=9.0, 2.4 Hz), 3.69(3H,s), 3.41(7H,br), 2.83(3H,s), 2.67(3H,s)

IR(KBr)ν(cm$^-$); 1649, 1559, 1507, 1437, 1219, 1091

EXAMPLE 21

Synthesis of Compound 21

To 3.7 mg (0.092 mmol) of 60% sodium hydride was added 0.1 ml of N,N-dimethylformamide, and then 0.4 ml of an N,N-dimethylformamide solution containing 20 mg (0.078 mmol) of Compound (A) was added thereto. The mixture was stirred in an argon atmosphere at −20° C. for 3 hours. To the reaction mixture was added 0.5 ml of an N,N-dimethylformamide solution containing 31 mg (0.094 mmol) of p-nitrophenyl 4-n-propyloxyphenoxyacetate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol= 100:1) to give 18 mg of Compound 21(yield: 50%).

The physicochemical properties of Compound 21 are as follows.

$^1$H-NMR(400 MHz, CDCl$_3$)δ(ppm); 10.30(1H,br), 7.25 (1H,br), 6.87(2H,d,J=9.2 Hz), 6.83(2H,d,J=9.3 Hz), 4.73 (2H,s), 4.21(1H,br d,J=10.8 Hz), 4.11(1H,m), 3.86(2H,t,J= 6.6 Hz), 3.81(3H,s), 3.56(1H,m), 2.60(3H,s), 2.30(1H,dd,J= 7.5, 3.4 Hz), 1.77(2H, m), 1.17(1H,m), 1.02(3H,t, J=7.4 Hz)

IR(KBr)ν(cm$^{-1}$); 1701, 1606, 1506, 1457, 1293, 1213

SIMS (m/z); 451(M+H) $^+$

EXAMPLE 22

Synthesis of Compound 22

To 3.7 mg (0.092 mmol) of 60% sodium hydride was added 0.1 ml of N,N-dimethylformamide, and 0.4 ml of an N,N-dimethylformamide solution containing 20 mg (0.078 mmol) of Compound (A) was added thereto. The mixture was stirred in an argon atmosphere at −20° C. for 3 hours. To the reaction mixture was added 0.5 ml of an N,N-dimethylformamide solution containing 34 mg (0.095 mmol) of p-nitrophenyl 4-n-pentyloxyphenoxyacetate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol= 100:1) to give 18 mg of Compound 22(yield: 48%).

The physicochemical properties of Compound 22 are as follows.

$^1$H-NMR(400 MHz, CDCl$_3$)δ(ppm); 10.28(1H,br), 7.25 (1H,br), 6.87(2H,d,J=9.2 Hz), 6.82(2H,d,J=9.3 Hz), 4.72 (2H,s), 4.21(1H,br d,J=10.7 Hz), 4.10(1H,m), 3.90(2H, t,J= 6.6 Hz), 3.81(3H,s), 3.56(1H,m), 2.60(3H,s), 2.30(1H,dd,J= 7.6, 3.6 Hz), 1.77(2H,m), 1.43(4H,m), 1.17(1H,m), 0.92(3H, t,J=7.2 Hz)

IR(KBr)ν(cm$^{-1}$); 1703, 1604, 1507, 1400, 1293, 1261, 1215

SIMS (m/z); 479(M+H) $^+$

EXAMPLE 23

Synthesis of Compound 23

To 6.3 mg (0.0158 mmol) of 60% sodium hydride was added 0.3 ml of N,N-dimethylformamide, and 0.5 ml of an N,N-dimethylformamide solution containing 30 mg of Compound (A) was added thereto. The mixture was stirred in an argon atmosphere at from −20° C. for 2.5 hours. To the reaction mixture was added 0.5 ml of an N,N-dimethylformamide solution containing 49.7 mg (0.139 mmol) of p-nitrophenyl 4-n-(trifluoromethoxy) phenoxyacetate, and the mixture was stirred for 1.25 hours. To the reaction mixture was added a 0.01M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol= 100:1) to give 39.6 mg of Compound 23(yield: 72%).

The physicochemical properties of Compound 23 are as follows.

$^1$H-NMR (270 MHz, CDCl$_3$)δ(ppm); 11.90(1H,brs), 7.15 (2H,d,J=8.6 Hz), 7.00(1H,br), 6.93(2H,d,J=8.9 Hz), 4.77 (2H,s), 4.15(2H,brs), 3.80(3H,s), 3.63(1H,brs), 2.60(3H,s), 2.33(1H,dd,J=7.3, 3.0 Hz), 1.18(1H,brs)

FABMS(m/z); 479(M+3) $^+$, 477(M+H) $^+$

IR(KBr)ν(cm$^{-1}$); 1730, 1697, 1647, 1601, 1512, 1410, 1252, 1217, 1174, 1138, 1096

EXAMPLE 24

Synthesis of Compound 24

To 19.9 mg (0.0418 mmol) of Compound 23 obtained in Example 23 were added 1.06 ml of acetonitrile and 14.19 μl of 48% hydrobromic acid. After the solution was stirred at room temperature for 60 minutes, the reaction mixture was concentrated under reduced pressure. The obtained crude product was dissolved in 1.06 ml of methylene chloride, and 25.3 mg (0.125 mmol) of p-nitrophenyl chloroformate and 17.5 μl (0.125 mmol) of triethylamine were added thereto at −78° C. The mixture was stirred for 35 minutes. Then, to this solution was added 24.3 μl (0.219 mmol) of N-methylpiperazine, and the mixture was stirred at −78° C. to 0° C. for 2 hours. To the reaction mixture was added a saturated aqueous solution of sodium hydrogen carbonate, and the solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=10:1) to give 25.7 mg of Compound 24 (yield: 90%).

The physicochemical properties of Compound 24 are as follows.

$^1$H-NMR(270 MHz, CDCl$_3$)δ(ppm); 9.18(1H,brs), 8.04 (1H,s), 7.16(2H,d,J=8.9 Hz), 7.01(2H,d,J=9.2 Hz), 4.86(1H, d,J=14.9 Hz), 4.80(1H,d,J=14.9 Hz), 4.51(1H,brt,J=7.6 Hz), 4.35(1H,d,J=10.6 Hz), 4.17(1H,dd,J=10.6, 8.6 Hz), 3.92 (3H,s), 3.76(1H,brd,J=10.2 Hz), 3.63–3.72(4H,m), 3.19(1H, dd,J=9.9, 9.9 Hz), 2.47(7H,brs), 2.35(3H,s)

FABMS(m/z); 685, 683(M+H) $^+$

IR(KBr)ν(cm$^{-1}$); 1701, 1670, 1506, 1439, 1417, 1261, 1238, 1220, 1196, 1159, 1005

EXAMPLE 25

Synthesis of Compound 25

To 19.5 mg (0.0285 mmol) of Compound 24 obtained in Example 24 were added 0.92 ml of ethanol and 0.46 ml of methanol, and 8.3 μl of 6.86N hydrogen chloride in ethanol was added thereto. The mixture was stirred at room temperature for 3.5 hours. The reaction mixture was concentrated under reduced pressure to give 20.4 mg of Compound 25.

The physicochemical properties of Compound 25 are as follows.

$^1$H-NMR (270 MHz, DMSO-d$_6$)δ(ppm); 12.13(1H,s), 10.62(1H,br), 7.91(1H,s), 7.29(2H,d,J=8.6 Hz), 7.09(2H,d, J=9.2 Hz), 5.10(1H,d,J=15.8 Hz), 4.97(1H,d,J=15.5 Hz), 4.50–4.52 (1H,m), 4.32(1H,dd,J=10.2, 8.9 Hz), 4.17(1H, d, J=10.6 Hz), 3.85(3H,s), 3.79(1H,dd,J=9.6, 2.0 Hz), 2.82(3H, s), 2.67(3H,s)

FABMS (m/z); (M+H) $^+$

IR(KBr)ν(cm$^{-1}$); 1716, 1695, 1506, 1439, 1417, 1248, 1232, 1194, 1171, 1097

EXAMPLE 26

Synthesis of Compound 26

To 1.9 mg (0.048 mmol) of 60% sodium hydride was added 0.1 ml of N,N-dimethylformamide, and 0.2 ml of an N,N-dimethylformamide solution containing 10 mg (0.04 mmol) of Compound (A) was added thereto. The mixture was stirred in an argon atmosphere at −20° C. for 1 hours. To the reaction mixture was added 0.2 ml of an N,N-dimethylformamide solution containing 19 mg (0.149 mmol) of p-nitrophenyl 4-tert-butoxycarbonylaminocinnamate, and the mixture was stirred at −20° C. to 0° C. for 3 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol=80:1) to give 13 mg of Compound 26(yield: 65%).

The physicochemical properties of Compound 26 are as follows.

$^1$H-NMR (270 MHz, CDCl$_3$)δ(ppm); 11.32(1H,br), 7.76 (1H,d,J=15.5 Hz), 7.51(2H,d,J=8.8 Hz), 7.41(2H,d,J=8.9 Hz), 6.80(1H,d,J=15.5 Hz), 6.62(1H,br), 4.23(1H,d,J=11.2 Hz), 4.12(1H,dd,J=11.2, 7.3 Hz), 3.82(3H,s), 3.59(1H, m), 2.62(3H,s), 2.40(1H,dd,J=7.6, 3.3 Hz), 2.05(1H,s), 1.54(9H, s), 1.30(1H,dd,J=4.3, 4.0 Hz)

IR(KBr)ν(cm$^{-1}$); 1707, 1620, 1587, 1525, 1520, 1394, 1294, 1240, 1159

SIMS (m/z); 504(M+H) $^+$

EXAMPLE 27

Synthesis of Compound 27

To 1.9 mg (0.048 mmol) of 60% sodium hydride was added 0.1 ml of N,N-dimethylformamide, and 0.2 ml of an N,N-dimethylformamide solution containing 10 mg (0.04 mmol) of Compound (A) was added thereto. The mixture was stirred in an argon atmosphere at −20° C. for 2 hours. To the reaction mixture was added 0.2 ml of an N,N-dimethylformamide solution containing 10 mg (0.052 mmol) of p-nitrophenyl 4-dimethylaminocinnamate, and the mixture was stirred at −20° C. to 0° C. for 1 hour. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol=50:1) to give 11 mg of Compound 27 (yield: 64%).

The physicochemical properties of Compound 27 are as follows.

$^1$H-NMR (270 MHz, CDCl$_3$)δ(ppm); 10.73(1H,br), 7.77 (1H,d,J=15.2 Hz), 7.46(2H,d,J=8.9 Hz), 6.59(2H,d,J=8.9 Hz), 6.64(1H,d,J=15.5 Hz), 6.63(1H,br), 4.21(1H, d, J=10.9 Hz), 4.14(1H,dd,J=10.9, 4.6 Hz), 3.82(3H,s), 3.53(1H,m), 3.04(6H,s), 2.61(3H,s), 2.36(1H,dd,J=7.3, 3.6 Hz), 1.30(1H, dd,J=4.9, 3.3 Hz)

IR(KBr)ν(cm$^{-1}$); 1701, 1593, 1525, 1389, 1360, 1242, 1217, 1169

SIMS (m/z); 432(M+H)$^+$

EXAMPLE 28

Synthesis of Compound 28

Compound 26.(8 mg, 0.016 mmol) obtained in Example 26 was dissolved in 1 ml of acetonitrile, and then 0.5 ml of 1N hydrobromic acid and 0.2 ml of trifluoroacetic acid were added thereto. After the solution was stirred at room temperature for 4 hours, the reaction mixture was concentrated under reduced pressure. To the obtained crude product were added 1 ml of acetonitrile, 0.2 ml of water and 0.2 ml of triethylamine, and the mixture was stirred for 24 hours. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by thin-layer silica-gel chromatography (developing solvent, chloroform:methanol=10:1) to give 3 mg of Compound 28 (yield: 47%).

The physicochemical properties of Compound 28 are as follows.

$^1$H-NMR(270 MHz, CDCl$_3$)δ(ppm); 10.28(1H,br), 7.74 (1H,d,J=15.5 Hz), 7.39(2H,d,J=8.6 Hz), 6.68(1H,d,J=15.5 Hz), 6.65(2H,d,J=8.5 Hz), 6.62(1H,br), 4.21(1H,d,J=11.2 Hz), 4.11(1H,dd,J=11.2, 6.3 Hz), 3.82(3H,s), 3.56(1H,m), 2.60(3H,s), 2.36(1H,dd,J=7.6, 3.3 Hz), 1.32(1H,dd,J=4.5, 3.4 Hz)

IR(KBr)ν(cm$^{-1}$); 1697, 1595, 1518, 1443, 1392, 1242, 1219, 1174

SIMS(m/z); 404(M+H)$^+$

EXAMPLE 29

Synthesis of Compound 29

To 12 mg (0.3 mmol) of 60% sodium hydride was added 0.6 ml of N,N-dimethylformamide, and 1.5 ml of an N,N-dimethylformamide solution containing 60 mg (0.23 mmol) of Compound (A) was added thereto. The reaction mixture was cooled to −20° C., and 1.5 ml of an N,N-dimethylformamide solution containing 124 mg (0.31 mmol) of p-nitrophenyl 3-(3-azidopropyloxy)-4-methoxycinnamate was added thereto. The mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=50:1) to give 77 mg of Compound 29 (yield: 65%).

The physicochemical properties of Compound 29 are as follows.

$^1$H-NMR (270 MHz, CDCl$_3$)δ(ppm); 9.81(1H,br), 7.68 (1H,d,J=15.5 Hz), 7.11(1H,dd,J=8.3, 2.0 Hz), 7.01(1H,d,J= 2.0 Hz), 6.81(1H,d,J=8.2 Hz), 6.66(1H,d,J=15.5 Hz), 6.56 (1H,br), 4.15(1H,d,J=11.2 Hz), 4.07(2H, t,J=5.9 Hz),4.06 (1H,m), 3.84(3H,s), 3.76(3H,s), 3.50(2H,t,J=6.6 Hz), 3.46 (1H,m), 2.52(3H,s), 2.31(1H,dd,J=7.6, 3.3 Hz), 2.05(2H,m), 1.25(1H,dd,J=5.3, 3.4 Hz)

IR(KBr)ν(cm$^{-1}$); 2098, 1697, 1622, 1608, 1516, 1392, 1263, 1217

SIMS (m/z); 518(M+H)$^+$

EXAMPLE 30

Synthesis of Compound 30

Compound 29(15 mg, 0.029 mmol) obtained in Example 29 was dissolved in 1.5 ml of tetrahydrofuran, and then 23 mg (0.088 mmol) of triphenylphosphine was added thereto. The mixture was stirred at room temperature for 30 minutes. To the reaction mixture was added 1.5 ml of water, and the mixture was stirred at room temperature for 24 hours. To the reaction mixture was added an aqueous solution of sodium hydrogen carbonate, and the resulting mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, chloroform:methanol:triethylamine at=200:10:1) to give 4 mg of Compound 30(yield: 28%).

The physicochemical properties of Compound 30 are as follows.

$^1$H-NMR (270 MHz, DMSO-d$_6$)δ(ppm); 7.75(1H,d,J= 15.2 Hz), 7.54(1H,br s) , 7.49(1H,br d,J=8.6 Hz), 7.18(1H, d,J=8.6 Hz), 7.09(1H,d,J=15.2 Hz), 7.03(1H,br), 4.15(1H,br d,J=11.2 Hz), 4.39(1H,m), 4.27(2H, t,J=6.3 Hz),3.96(3H,s), 3.87(3H,s), 3.61(1H,m), 3.12(2H,t,J=7.2 Hz), 2.61(3H,s), 2.23(1H,m), 2.16(2H,m), 1.46(1H,m)

IR(KBr)ν(cm$^{-1}$); 1647, 1610, 1512, 1458, 1394, 1385, 1294, 1219

SIMS(m/z); 492(M+H)$^+$

EXAMPLE 31

Synthesis of Compound 31

Compound 29(50 mg, 0.096 mmol) obtained in Example 29 was dissolved in 5 ml of acetonitrile, and 1 ml of 48% hydrobromic acid was added thereto. The mixture was stirred at room temperature for 1 hour. To the reaction mixture was added 1N hydrobromic acid, and the solution was extracted with chloroform. The chloroform layer was dried over anhydrous sodium sulfate, and then concentrated under reduced pressure. The obtained crude product was dissolved in 5 ml of methylene chloride. Then, 58 mg (0.29 mmol) of p-nitrophenyl chloroformate and succesively 0.04 ml (0.29 mmol) of triethylamine were added thereto at −78° C. The mixture was stirred for 30 minutes. To the reaction mixture was added 0.038 ml (0.34 mmol) of N-methylpiperazine, and the mixture was stirred at from −78° C. to 0° C. for 2 hours. To this reaction mixture was added a 0.2M phosphate buffer of pH7, and the solution was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, chloroform:methanol=20:1) to give 51 mg of an azido compound (yield: 73%). To 35 mg (0.049 mmol) of the azido compound were added 5 ml of methanol, 1 ml of acetone and 22 mg of a mixture of 10% lead/barium sulfate. The resulting mixture was stirred in a hydrogen atmosphere at room temperature for 4 hours. The reaction mixture was filtered, and then concentrated under reduced pressure. The obtained crude product was purified by silica-gel column chromatography (30 ml of silica gel, chloroform:methanol:ammonia=10:1:1) to give 12 mg of Compound 31(yield: 35%).

The physicochemical properties of Compound 31 are as follows.

$^1$H-NMR(270 MHz, DMSO-d$_6$)δ(ppm); 8.09(1H,br s), 7.96(1H,s), 7.90(2H,br), 7.58(1H,d,J=15.2 Hz), 7.44(1H,s), 7.35(1H,br d,J=8.2 Hz), 7.07(1H,d,J=15.5 Hz), 7.05(1H,d, J=8.6 Hz), 4.53(1H,m), 4.42(2H,m), 4.18(2H,t,J=5.9 Hz), 3.85(3H, s), 3.84(3H, s), 3.79(1H,m), 3.45(1H,m), 3.00(2H, br), 2.75(2H,br), 2.74(3H,s), 2.69(3H,s), 2.06(2H,m)

IR(KBr)ν(cm$^{-1}$); 3547, 1718, 1697, 1637, 1511, 1436, 1409, 1263, 1219

FABMS(m/z); 698, 700(M+H) $^+$

EXAMPLE 32

Synthesis of Compound 32

To 16 mg (0.023 mmol) of Compound 31 obtained in Example 31 was added 2 ml of methanol, and then 0.0084 ml of 6.86N hydrogen chloride in ethanol was added thereto. The mixture was stirred at 0° C. for 1 hour. The reaction mixture was concentrated under reduced pressure to give 16.4 mg of Compound 32.

The physicochemical properties of Compound 32 are as follows.

$^1$H-NMR (270 MHz, DMSO-d$_6$)δ(ppm); 12.18(1H,br), 10.93(1H,br), 8.09(1H,br s), 7.89(2H,br), 7.56(1H,d,J=15.2 Hz), 7.43(1H,br s), 7.33(1H,d,J=8.2 Hz), 7.06(1H,d,J=15.3 Hz), 7.03(1H,d,J=8.3 Hz), 4.50(1H,m), 4.40(2H,m), 4.15 (2H,t,J=5.6 Hz), 3.85(3H,s), 3.83(3H,s), 3.46(6H,br), 3.26 (4H,br), 2.99(2H,m), 2.84(3H,s), 2.68(3H,s), 2.05(2H,m)

IR(KBr)ν(cm$^{-1}$); 1716, 1647, 1509, 1437, 1408, 1263, 1140

FABMS (m/z); 700, 698(M+H) $^+$

EXAMPLE 33

Synthesis of Compound 33

To 3.7 mg (0.093 mmol) of 60% sodium hydride was added 0.2 ml of N,N-dimethylformamide, and then 0.5 ml of an N,N-dimethylformamide solution containing 20 mg (0.078 mmol) of Compound (A) was added thereto. The mixture was stirred in an argon atmosphere at −20° C. for 2 hours. To the reaction mixture was added 0.5 ml of an N,N-dimethylformamide solution containing 41 mg (0.10 mmol) of p-nitrophenyl 3-(3-dimethylaminopropyloxy)-4-methoxycinnamate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol=5:1) to give 21 mg of Compound 33 (yield: 52%).

The physicochemical properties of Compound 33 are as follows.

$^1$H-NMR(270 MHz,DMSO-d$_6$)δ(ppm); 12.38(1H,br), 7.59(1H,d,J=15.5 Hz), 7.39(1H,br s), 7.28(1H,br d,J=8.5 Hz), 7.00(1H,d,J=8.6 Hz), 6.94(1H,d,J=15.6 Hz), 6.90(1H, br s), 4.34(1H,br d,J=10.8 Hz), 4.27(1H,m), 4.06(1H,t,J=6.2 Hz), 3.81(3H,s), 3.76(1H,m), 3.73(3H,s), 3.12(2H,m), 2.59 (3H,s), 2.23(1H,m), 2.16(2H,m), 1.46(1H,m)

IR(KBr)ν(cm$^1$); 1684, 1601, 1443, 1437, 1385, 1263

FABMS (m/z); 520(M+H) $^+$

EXAMPLE 34

Synthesis of Compound 34

Compound 35(5 mg, 0.009 mmol) obtained in Example 35 was dissolved in 0.5 ml of ethylene dichloride, and 0.2 ml of 48% hydrobromic acid was added thereto. The mixture was stirred at 50° C. for 2 hours. To the reaction mixture was added methanol, and the solution was concentrated under reduced pressure. Acetonitrile (1 ml) and 4 ml of a 0.2M phosphate buffer of pH7 were added thereto, and the mixture was stirred at room temperature for 2 hours. To the reaction mixture was added an acetate buffer of pH4, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol=10:1) to give 4 mg of Compound 34(yield: 88%).

The physicochemical properties of Compound 34 are as follows.

$^1$H-NMR (270 MHz, CDCl$_3$)δ(ppm); 10.69(1H,br), 7.65 (1H,d,J=15.5 Hz), 7.15(1H,dd,J=8.2, 1.7 Hz), 6.96(1H,d,J= 2.0 Hz), 6.83(1H,d,J=8.6 Hz), 6.63(1H,d,J=15.5 Hz), 6.60 (1H,br), 4.66(2H,s), 4.14(1H,dd,J=10.9, 10.9 Hz),4.07(1H, m), 3.86(3H,s), 3.76(3H,s), 3.74(3H,s), 3.48(1H, m), 2.52 (3H,s), 2.31(1H,dd, J=7.6, 3.3 Hz), 1.25(1H,dd, J=5.0, 3.4 Hz)

IR(KBr)ν(cm$^{-1}$); 1699, 1653, 1616, 1516, 1458, 1396, 1219

SIMS(m/z); 507(M+H) $^+$

EXAMPLE 35

Synthesis of Compound 35

To 4.0 mg (0.1 mmol) of 60% sodium hydride was added 0.2 ml of N,N-dimethylformamide, and then 0.5 ml of an N,N-dimethylformamide solution containing 20 mg (0.078 mmol) of Compound (A) was added thereto. The mixture was stirred in an argon atmosphere at −20° C. for 2 hours. To the reaction mixture was added 0.5 ml of an N,N-dimethylformamide solution containing 41 mg (0.096 mmol) of p-nitrophenyl 3-tert-butoxycarbonylmethoxy-4-methoxycinnamate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol=50:1) to give 35 mg of Compound 35(yield: 82%).

The physicochemical properties of Compound 35 are as follows.

$^1$H-NMR (270 MHz, CDCl$_3$)δ(ppm); 10.61(1H,br), 7.65 (1H,d,J=15.2 Hz), 7.15(1H,dd,J=8.2, 1.6 Hz), 6.92(1H,d,J= 2.0 Hz), 6.83(1H,d,J=8.5 Hz), 6.60(1H,d,J=15.5 Hz), 6.58 (1H,br), 4.52(2H,s), 4.14(1H,d,J=10.9 Hz), 4.09(1H, m), 3.86(3H,s), 3.75(3H,s), 3.49(1H,m), 2.54(3H,s), 2.31(1H, dd,J=7.6, 3.3 Hz), 1.55(9H,s), 1.25(1H,dd,J=4.6, 3.4 Hz)

IR(KBr)ν(cm$^{-1}$); 1751, 1701, 1616, 1512, 1458, 1392, 1294, 1142

FABMS(m/z); 549(M+H) $^+$

EXAMPLE 36

Synthesis of Compound 36

To 99 mg (0.18 mmol) of Compound 35 obtained in Example 35 were added 5 ml of acetonitrile and 0.155 ml of 48% hydrobromic acid. The mixture was stirred at room temperature for 1 hour. To the reaction mixture was added 1N hydrobromic acid, and the solution was extracted with chloroform. The chloroform layer was dried over anhydrous sodium sulfate, and then concentrated under reduced pressure. The obtained crude product was dissolved in 5 ml of methylene chloride. Then, 109 mg (0.54 mmol) of p-nitrophenyl chloroformate and 0.076 ml (0.54 mmol) of triethylamine were added thereto at −78° C. The mixture was stirred for 1 hour. To the reaction mixture was added 0.162 ml (1.8 mmol) of a 50% dimethylamine aqueous solution, and the mixture was stirred at −78° C. to 0° C. for 2 hours. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=20:1) to give 44 mg of an ester of Compound 36(yield: 35%). To 30 mg (0.043 mmol) of the ester were added 1 ml of ethylene dichloride and 0.051 ml of trifluoroacetic acid, and the mixture was stirred at 80° C. for 24 hours. To the reaction mixture was added 1N hydrobromic acid, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol:acetic acid=100:10:1) to give 23 mg of Compound 36(yield: 83%).

The physicochemical properties of Compound 36 are as follows.

$^1$H-NMR (270 MHz, DMSO-d$_6$)δ(ppm); 12.01(1H,br), 8.02(1H,br), 7.51(1H,d,J=15.1 Hz), 7.26(1H,br d,J=8.5 Hz), 7.17(1H,br s), 6.97(1H,d,J=15.1 Hz), 6.96(1H,d,J=8.5 Hz), 4.50(1H,m), 4.38(2H,m), 4.30(2H,s), 3.84(3H,s), 3.81(3H,s), 3.78(2H,br), 3.15(3H,s), 2.96(3H,s), 2.65(3H,s)

IR(KBr)ν(cm$^{-1}$); 1701, 1585, 1437, 1416, 1317, 1267, 1169

FABMS(m/z); 645, 643(M+H) $^+$

EXAMPLE 37

Synthesis of Compound 37

To 10 mg (0.25 mmol) of 60% sodium hydride was added 0.5 ml of N,N-dimethylformamide, and 1.5 ml of an N,N-dimethylformamide solution containing 50 mg (0.19 mmol) of Compound (A) was added thereto. The mixture was stirred in an argon atmosphere at −20° C. for 2 hours. To the reaction mixture was added 2.0 ml of an N,N-dimethylformamide solution containing 103 mg (0.25 mmol) of p-nitrophenyl 3-tert-butoxycarbonylamino-4-methoxycinnamate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=80:1) to give 98 mg of tert-butoxycarbonyl (Boc) compound of Compound 37(yield: 97%).

The physicochemical properties of Boc compound of Compound 37 are as follows.

$^1$H-NMR (270 MHz, CDCl$_3$)δ(ppm); 10.76(1H,br), 8.37 (1H,br), 7.78(1H,d,J=15.5 Hz), 7.17(1H,dd,J=8.6, 2.3 Hz), 7.11(1H,br s), 6.84(1H,d,J=8.6 Hz), 6.79(1H,br), 6.74(1H, d,J=15.5 Hz), 4.24(1H,d,J=10.5 Hz), 4.16(1H,dd,J=10.4, 3.9 Hz), 3.92(3H,s), 3.82(3H,s), 3.54(1H,m), 2.60(3H,s), 2.36 (1H,dd, J=7.5, 3.3 Hz), 1.54(9H,s), 1.32(1H,dd,J=4.0, 3.3 Hz)

IR(KBr)ν(cm$^-$); 1705, 1614, 1531, 1390, 1261, 1219, 1157

FABMS (m/z); 534(M+H) $^+$

Boc compound of Compound 37(30 mg, 0.056 mmol) was dissolved in 3 ml of ethylene dichloride, and 0.1 ml of 48% hydrobromic acid was added thereto. The mixture was stirred at 50° C. for 2 hours. To the reaction mixture was added a saturated aqueous solution of sodium hydrogen carbonate, and the resulting solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=40:1) to give 12 mg of Compound 37(yield: 49%).

The physicochemical properties of Compound 37 are as follows.

$^1$H-NMR(270 MHz, DMSO-d$_6$)δ(ppm); 12.40(1H,br), 7.53(1H,d,J=15.5 Hz), 7.03(1H,d,J=1.7 Hz), 6.96(1H,dd,J= 8.3, 1.8 Hz), 6.88(1H,d,J=8.3 Hz), 6.83(1H,br), 6.76(1H,d, J=15.5 Hz), 4.88(2H,s), 4.30(1H,d,J=10.5 Hz), 4.22(1H,dd, J=10.4, 4.9 Hz), 3.85(3H,s), 3.76(3H,s), 3.48(1H,m), 2.50 (3H,s), 2.11(1H,dd,J=7.3, 4.0 Hz), 1.35(1H,dd,J=4.6, 3.3 Hz)

IR(KBr)ν(cm$^{-1}$); 1703, 1612, 1514, 1446, 1390, 1271, 1217, 1111

FABMS (m/z); 434(M+H) $^+$

EXAMPLE 38

Synthesis of Compound 38

Boc compound of Compound 37(30 mg, 0.056 mmol) obtained in Example 37 was dissolved in 3 ml of acetonitrile, and then 0.015 ml of 48% hydrobromic acid was added thereto. The mixture was stirred at 0° C. for 1 hour. To the reaction mixture was added an acetate buffer of pH4, and the resulting solution was extracted with chloroform. The chloroform layer was dried over anhydrous sodium sulfate, and then concentrated under reduced pressure. The obtained crude product was dissolved in 3 ml of methylene chloride. Then, 0.013 mg (0.17 mmol) of methyl chloroformate and 0.024 ml (0.17 mmol) of triethylamine were added thereto at −78° C. The mixture was stirred for 1 hour. To this reaction mixture was added an acetate buffer of pH4, and the resulting solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=80:1) to give 32 mg of Boc compound of Compound 38(yield: 85%). To 25 mg (0.037 mmol) of this Boc compound were added 2 ml of ethylene dichloride and 0.065 ml of 48% hydrobromic acid, and the mixture was stirred at 80° C. for 1 hour. To the mixture was added a phosphate buffer of pH7, and the resulting solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=10:1) to give 13 mg of Compound 38(yield: 61%).

The physicochemical properties of Compound 38 are as follows.

$^1$H-NMR(270 MHz, CDCl$_3$)δ(ppm); 8.58(1H,br), 8.42 (1H,br), 7.73(1H,d,J=15.2 Hz), 7.71(1H,t,J=4.5 Hz), 7.01 (2H,br), 6.98(1H,dd,J=8.4, 2.0 Hz), 6.80(1H,d,J=8.3 Hz), 6.75(1H, d,J=15.2 Hz), 4.56(1H,m), 4.47(1H,br d,J=10.6 Hz), 4.30(1H,dd,J=8.6, 8.6 Hz), 3.97(3H,s), 3.95(3H,s), 3.90(3H,s), 3.80(1H, dd,J=9.5, 2.3 Hz), 3.23(1H,dd,J=9.6, 9.6 Hz), 2.71(3H,s)

IR(KBr)ν(cm$^-$); 1767, 1647, 1514, 1439, 1282, 1221, 1115

FABMS (m/z); 574, 572(M+H) $^+$

EXAMPLE 39

Synthesis of Compound 39

To 29 mg (0.054 mmol) of Boc compound of Compound 37 obtained in Example 37 were added 3 ml of acetonitrile and 0.02 ml of 48% hydrobromic acid, and the mixture was stirred at room temperature for 1 hour. To the reaction mixture was added 1N hydrobromic acid, and the solution was extracted with chloroform. The chloroform layer was dried over anhydrous sodium sulfate, and then concentrated under reduced pressure. The obtained crude product was dissolved in 3 ml of methylene chloride. Then, 33 mg (0.16 mmol) of p-nitrophenyl chloroformate and 0.023 ml (0.16 mmol) of triethylamine were added thereto at −78° C. The mixture was stirred for 1 hour. To the reaction mixture was added 0.021 ml (0.19 mmol) of N-methylpiperazine, and the mixture was stirred at −78° C. to 0° C. for 2 hours. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=20:1) to give 20 mg of Boc compound of Compound 39(yield: 50%). To 20 mg (0.027 mmol) of the Boc compound were added 2 ml of ethylene dichloride and 0.025 ml of 48% hydrobromic acid, and the mixture was stirred at 50° C. for 2 hours. To the reaction mixture was added a saturated aqueous solution of sodium hydrogen carbonate, and the mixture was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=20:1) to give 15 mg of Compound 39 (yield: 87%).

The physicochemical properties of Compound 39 are as follows.

$^1$H-NMR(270 MHz, CDCl$_3$)δ(ppm); 8.80(1H, s), 8.25 (1H, br), 7.73(1H, d,J=15.2 Hz), 7.02(1H,br s), 6.80(1H,d, J=8.3 Hz), 6.75(1H, d, J=15.8 Hz), 4.57(1H, m), 4.47(1H, br d, J=10.2 Hz), 4.30(1H, m), 3.96(3H, s), 3.90(3H, s), 3.81 (1H, dd,J=9.6, 2.3 Hz), 3.76(2H, br), 3.63(2H, br), 2.68(3H, s), 2.50(4H,br), 2.37(3H,s)

IR(KBr)ν(cm$^{-1}$); 1699, 1646, 1589, 1514, 1437, 1408, 1284, 1257, 1219, 1151, 1095

FABMS(m/z); 642, 640(M+H) $^+$

EXAMPLE 40

Synthesis of Compound 40

Methanol (1 ml) was added to 15 mg (0.023 mmol) of Compound 39 obtained in Example 39, and 0.005 ml of 6.86N hydrogen chloride in ethanol was added thereto. The solution was stirred at 0° C. for 2 hours. The reaction mixture was concentrated under reduced pressure to give 16 mg of Compound 40.

The physicochemical properties of Compound 40 are as follows.

$^1$H-NMR(270 MHz, DMSO-d$_6$)δ(ppm); 12.09(1H,br), 10.64(1H,br), 8.10(1H,br), 7.49(1H,d,J=15.2 Hz), 7.22(1H, br s), 7.16(1H,d,J=8.6 Hz), 6.95(1H,d,J=2.9 Hz), 6.90(1H, d,J=15.1 Hz), 4.42(2H,m), 4.19(1H,m), 3.86(3H,s), 3.85 (3H,s), 3.79(1H,br), 3.49(9H,br), 2.89(3H,s), 2.68(3H,s)

IR(KBr)ν(cm$^{-1}$); 1699, 1645, 1514, 1439, 1412, 1281, 1219

FABMS(m/z); 642, 640(M+H) $^+$

EXAMPLE 41

Synthesis of Compound 41

To 7.5 mg (0.19 mmol) of 60% sodium hydride was added 0.2 ml of N,N-dimethylformamide, and 1.0 ml of an N,N-dimethylformamide solution containing 40 mg (0.155 mmol) of Compound (A) was added thereto. The mixture was stirred in an argon atmosphere at −20° C. for 2 hours. To the reaction mixture was added 1.0 ml of an N,N-dimethylformamide solution containing 64 mg (0.19 mmol) of p-nitrophenyl 3-dimethylamino-4-methoxycinnamate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol= 50:1) to give 46 mg of Compound 41(yield: 64%).

The physicochemical properties of Compound 41 are as follows.

$^1$H-NMR (270 MHz, CDCl$_3$)δ(ppm); 10.73(1H,br), 7.77 (1H, d, J=15.5 Hz), 7.22(1H,dd,J=8.6, 2.0 Hz), 7.11(1H,d, J=2.1 Hz), 6.87(1H,d,J=8.5 Hz), 6.73(1H,d,J=15.5 Hz), 4.23 (1H,d,J=10.9 Hz), 4.15(1H,dd,J=11.0, 4.6 Hz), 3.94(3H,s), 3.82(3H,s), 3.55(1H,m), 2.82(6H,s), 2.61(3H,s), 2.11(1H, d.d,J=7.6, 3.2 Hz), 1.32(1H,dd,J=4.9, 3.3 Hz)

IR(KBr)ν(cm$^{-1}$); 1705, 1614, 1576, 1387, 1240, 1219, 1109

FABMS (m/z); 462(M+H) $^+$

EXAMPLE 42

Synthesis of Compound 42

To 24 mg (0.052 mmol) of Compound 41 obtained in Example 41 were added 1 ml of acetonitrile and 0.018 ml of 48% hydrobromic acid, and the mixture was stirred at room temperature for 1 hour. The reaction mixture was concentrated under reduced pressure, and the resulting crude product was dissolved in a mixed solvent of 1 ml of methylene chloride and 0.5 ml of toluene. Then, 32 mg (0.16 mmol) of p-nitrophenyl chloroformate and 0.029 ml (0.21 mmol) of triethylamine were added thereto at −78° C. The mixture was stirred for 1 hour. To the reaction mixture was added 0.021 ml (0.19 mmol) of N-methylpiperazine, and the mixture was stirred at −78° C. to 0° C. for 2 hours. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=10:1) to give 22 mg of Compound 42(yield: 63%).

The physicochemical properties of Compound 42 are as follows.

$^1$H-NMR(270 MHz, CDCl$_3$)δ(ppm); 8.80(1H, s), 8.25 (1H, br s), 7.79(1H, d, J=15.2 Hz), 7.26(1H, m), 7.17(1H, d, J=2.0 Hz), 6.88(1H, d, J=8.3 Hz), 6.77(1H, d, J=15.5 Hz), 4.45–4.57(2H, m), 4.32(1H, m), 3.96(3H, s), 3.94(3H, s), 3.80(1H, m), 3.79(2H,br), 3.63(2H, br), 3.23(1H,dd, J=10.2, 9.9 Hz), 2.85(6H, s), 2.68(3H, s), 2.50(4H, br), 2.37(3H,s)

FABMS(m/z); 670, 668(M+H)$^+$

IR(KBr)ν(cm$^{-1}$); 1726, 1697, 1646, 1408, 1240, 1215, 1149, 1093

EXAMPLE 43

Synthesis of Compound 43

To 22 mg (0.033 mmol) of Compound 42 obtained in Example 42 was added 1 ml of methanol, and 0.006 ml of 6.86N hydrogen chloride in ethanol was added thereto. The mixture was stirred at 0° C. for 2 hours. The reaction mixture was concentrated under reduced pressure to give 21 mg of Compound 43.

The physicochemical properties of Compound 43 are as follows.

$^1$H-NMR (270 MHz, DMSO-d$_6$)δ(ppm); 12.09(1H,br), 10.55(1H,br), 8.10(1H,br s), 7.58(1H,d,J=15.2 Hz), 7.46 (2H,br), 7.04(1H,d,J=15.2 Hz), 7.03(1H,br), 4.49(4H,m), 4.18(1H,m), 3.86(3H,s), 3.85(3H,s), 3.79(1H,br d,J=9.9 Hz), 3.48(3H,br), 2.85(10H,s), 2.68(3H,s), 2.50(3H,s)

IR(KBr)ν(cm$^{-1}$); 1716, 1697, 1647, 1510, 1434, 1414, 1246, 1217, 1095

EXAMPLE 44

Synthesis of Compound 44

To 20.4 mg (0.0442 mmol) of Compound 41 obtained in Example 41 were added 1.86 ml of acetonitrile and 15 μl of 48% hydrobromic acid. The mixture was stirred at room temperature for 60 minutes, and the reaction mixture was then concentrated under reduced pressure. The resulting crude product was dissolved in 1.86 ml of methylene chloride. Then, 12.9 μl (0.137 mmol) of acetic anhydride and 17.3 mg (0.141 mmol) of 4-dimethylaminopyridine were added thereto at 0° C. The mixture was stirred for 1 hour. To this reaction mixture was added a 0.01M phosphate buffer of pH7, and the mixture was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=15:1) to give 23.8 mg of Compound 44(yield: 92%).

The physicochemical properties of Compound 44 are as follows.

$^1$H-NMR(270 MHz, CDCl$_3$)δ(ppm); 9.33(1H,brs), 8.29 (1H,brs), 7.80(1H,d,J=15.2 Hz), 7.24(1H,d,J=9.2 Hz), 7.16 (1H,s), 6.87(1H,d,J=8.6 Hz), 6.78(1H,d,J=15.5 Hz), 4.54 (1H,br), 4.48(1H,d,J=11.2 Hz), 4.33(1H,brt,J=8.9 Hz), 3.95 (3H,s), 3.93(3H,s), 3.80(1H,brd, J=7.6 Hz), 3.23(1H,dd,J= 10.2, 9.9 Hz), 2.84(6H,s), 2.56(3H,s), 2.34(3H,s)

FABMS (m/z); 586, 584(M+H)$^+$

IR(KBr)ν(cm$^-$); 1767, 1697, 1645, 1508, 1435, 1414, 1321, 1246, 1190, 1088, 1028

EXAMPLE 45

Synthesis of Compound 45

To 20.4 mg (0.0349 mmol) of Compound 44 obtained in Example 44 was added 1.7 ml of anhydrous ethyl acetate, and 10.17 μl of 6.86N hydrogen chloride in ethanol was added thereto. The mixture was stirred at room temperature for 3 hours. The reaction mixture was concentrated under reduced pressure to obtain 24.6 mg of Compound 45.

The physicochemical properties of Compound 45 are as follows.

$^1$H-NMR(270 MHz, DMSO-d$_6$)δ(ppm); 12.07(1H,s), 8.06(1H,brs), 7.95(1H,br), 7.80–7.83(1H,br), 7.63(1H,d,J= 15.5 Hz), 7.27(1H,d,J=8.6 Hz), 7.15(1H,d,J=15.2 Hz), 4.43–4.53(3H,br), 3.98(3H,s), 3.85(3H,s), 3.79(1H,br), 3.09 (6H,s), 2.66(3H,s), 2.39(3H,s)

IR(KBr)ν(cm$^{-1}$); 1759, 1693, 1651, 1514, 1437, 1414, 1277, 1203, 1090, 1014

EXAMPLE 46

Synthesis of Compound 46

To 6.4 mg (0.16 mmol) of 60% sodium hydride was added 0.3 ml of N,N-dimethylformamide, and 0.9 ml of an N,N-dimethylformamide solution containing 34 mg (0.13 mmol) of Compound (A) was added thereto. The mixture was stirred in an argon atmosphere at −20° C. for 2 hours. To the reaction mixture was added 0.5 ml of an N,N-dimethylformamide solution containing 58 mg (0.16 mmol) of p-nitrophenyl 3-dimethylamino-4-methoxycinnamate, and the mixture was stirred at −20° C. to 0° C. for 2 hours. To the reaction mixture was added a 0.2M phosphate buffer of pH7, and the solution was extracted with ethyl acetate. The ethyl acetate layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol= 50:1) to give 55 mg of Compound 46(yield: 87%).

The physicochemical properties of Compound 46 are as follows.

$^1$H-NMR(270 MHz, CDCl$_3$)δ(ppm); 10.39(1H,br), 7.76 (1H,d,J=15.5 Hz), 7.25(1H,dd, J=8.6, 1.9 Hz), 7.11(1H,d,J= 2.0 Hz), 6.86(1H,d,J=8.6 Hz), 6.70(1H,d,J=15.5 Hz), 6.67 (1H,br s), 4.22(1H,d,J=10.9 Hz), 4.15(1H,dd,J=10.9, 4.6 Hz), 3.90(3H,s), 3.82(3H,s), 3.54(1H,m), 3.19(4H,q,J=7.3 Hz), 2.60(3H,s), 2.36(1H,dd, J=7.6, 3.6 Hz), 1.32(1H,dd,J= 5.3, 3.5 Hz), 1.05(6H, t,J=7.0 Hz)

IR(KBr)ν(cm$^-$); 1701, 1616, 1508, 1389, 1255, 1109

FABMS (m/z); 490(M+H)$^+$

EXAMPLE 47

Synthesis of Compound 47

To 16 mg (0.033 mmol) of Compound 46 obtained in Example 46 were added 1.5 ml of acetonitrile and 0.06 ml of 48% hydrobromic acid. The mixture was stirred at room temperature for 1 hour. To the reaction mixture was added 1N hydrobromic acid, and the solution was extracted with chloroform. The chloroform layer was dried over anhydrous sodium sulfate, and then concentrated under reduced pressure. The resulting crude product was dissolved in 1.5 ml of methylene chloride. Then, 0.008 ml (0.10 mmol) of methyl chloroformate and 0.014 ml (0.10 mmol) of triethylamine were added thereto at −78° C. The mixture was stirred for 1 hour. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (20 ml of silica gel, chloroform:methanol=80:1) to give 17 mg of Compound 47 (yield: 82%).

The physicochemical properties of Compound 47 are as follows.

$^1$H-NMR(270 MHz, CDCl$_3$)δ(ppm); 8.63(1H,br), 8.43 (1H,br), 7.78(1H,d,J=15.6 Hz), 7.29(1H,dd,J=8.9, 2.0 Hz), 7.17(1H,d,J=2.0 Hz), 6.88(1H,d,J=8.6 Hz), 6.75(1H,d,J= 15.5 Hz), 6.74(1H,br s), 4.56(1H,m), 4.50(1H,dd,J=10.5, 1.7 Hz), 4.34(1H,dd,J=10.4, 10.4 Hz), 3.97(3H,s), 3.95(3H,s), 3.91(3H,s), 3.81(1H,dd,J=6.7, 2.3 Hz), 3.25(1H,dd,J=6.7, 6.7 Hz), 3.21(4H,q,J=6.9 Hz), 2.71(3H,s), 1.06(6H,t,J=7.0 Hz)

IR(KBr)ν(cm$^{-1}$); 1699, 1653, 1645, 1591, 1506, 1412, 1257

FABMS(m/z); 629, 627(M) $^+$

EXAMPLE 48

Synthesis of Compound 48

To 20 mg (0.041 mmol) of Compound 46 obtained in Example 46 were added 2 ml of acetonitrile and 0.1 ml of 48% hydrobromic acid. The mixture was stirred at room temperature for 1 hour. To the reaction mixture was added 1N hydrobromic acid, and the solution was extracted with chloroform. The chloroform layer was dried over anhydrous sodium sulfate, and then concentrated under reduced pressure. The resulting crude product was dissolved in 2 ml of methylene chloride. Then, 38 mg (0.125 mmol) of bis(p-nitrophenyl) carbonate and 0.018 ml (0.13 mmol) of triethylamine were added thereto at 0° C. The mixture was stirred for 2 hours. To the reaction mixture was added 0.023 ml (0.17 mmol) of N-methylpiperazine, and the mixture was stirred at 0° C. for 2 hours. To the reaction mixture was added a 0.2M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by silica-gel column chromatography (30 ml of silica gel, chloroform:methanol=20:1) to give 14 mg of Compound 48 (yield: 50%).

The physicochemical properties of Compound 48 are as follows.

$^1$H-NMR(270 MHz, CDCl$_3$)δ(ppm); 8.78(1H,s), 8.25 (1H,br s), 7.79(1H,d,J=15.2 Hz), 7.28(1H, m), 7.17(1H, d, J=2.0 Hz), 6.89(1H, d, J=8.6 Hz), 6.76(1H, d, J=15.5 Hz), 4.58(1H, m), 4.47(1H, br d, J=10.6 Hz),4.31(1H, m), 3.96 (3H, s), 3.91(3H, s), 3.82(1H, m), 3.79(2H, br),3.63(2H,br), 3.21(4H, q, J=6.9 Hz), 2.69(3H, s), 2.51(4H, br), 2.37(3H, s), 1.07(6H, t, J=6.9 Hz)

IR(KBr)ν(cm$^{-1}$); 1697, 1652, 1591, 1506, 1408, 1292, 1259, 1217, 1093

EXAMPLE 49

Synthesis of Compound 49

To 11 mg (0.016 mmol) of Compound 48 obtained in Example 48 was added 1 ml of ethanol, and 0.004 ml of 6.86N hydrogen chloride in ethanol was added thereto. The mixture was stirred at 0° C. for 1 hour. The reaction mixture was concentrated under reduced pressure to give 13 mg of Compound 49.

The physicochemical properties of Compound 49 are as follows.

$^1$H-NMR (270 MHz, DMSO-d$_6$)δ(ppm); 12.19(1H,br), 10.88(1H,br), 8.10(2H,br), 7.60(1H,br d,J=8.6 Hz), 7.40 (1H,br s), 7.24(1H,br s), 7.00(1H,br), 4.58(3H,m), 3.85(6H, s), 3.81–3.26(6H,m), 3.21(4H,q,J=7.2 Hz), 2.88(4H,br), 2.69(3H,s), 2.51(4H,br), 2.37(3H,s), 1.07(6H,t,J=7.0 Hz)

IR(KBr)ν(cm$^{-1}$); 1714, 1645, 1435, 1417, 1410, 1255, 1219

FABMS(m/z); 698, 696(M+H) $^+$

EXAMPLE 50

Synthesis of Compound 50

To 32.2 mg (0.0689 mmol) of Compound 41 obtained in Example 41 were added 2.94 ml of acetonitrile and 18.2 μl of 35% hydrochloric acid. The mixture was stirred at room temperature for 60 minutes, and concentrated under reduced pressure. The resulting crude product was dissolved in 2.94 ml of methylene chloride. Then, 20.4 μl (0.216 mmol) of acetic anhydride and 27.2 mg (0.223 mmol) of 4-dimethylaminopyridine were added thereto. The mixture was stirred for 2 hours. To the reaction mixture was added a 0.01M phosphate buffer of pH7, and the solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol=15:1) to give 26.3 mg of Compound 50(yield: 70%).

The physicochemical properties of Compound 50 are as follows.

$^1$H-NMR(270 MHz, CDCl$_3$)δ(ppm); 9.62(1H,brs), 8.29 (1H,brs), 7.79(1H,d,J=15.5 Hz), 7.23(1H,d,J=9.6 Hz), 7.15 (1H,s), 6.86(1H,d,J=8.6 Hz), 6.78(1H,d,J=15.2 Hz), 4.41–4.54(1H,br), 4.50(1H,d,J=9.9 Hz), 4.32(1H,dd,J=9.2, 8.2 Hz), 3.92(6H,s), 3.85–3.90(1H,m), 3.35(1H,dd,J=10.2, 10.2 Hz), 2.83(6H,s), 2.53(3H,s), 2.32(3H,s)

FABMS(m/z); 542, 540(M+H) $^+$

IR(KBr)ν(cm$^{-1}$); 1697, 1643, 1591, 1510, 1437, 1414, 1242, 1190, 1115, 1090

EXAMPLE 51

Synthesis of Compound 51

To 18.3 mg (0.0339 mmol) of Compound 50 obtained in Example 50 was added 1.52 ml of anhydrous ethyl acetate, and then 9.9 μl of 6.86N hydrogen chloride in ethanol was added thereto. The mixture was stirred at room temperature for 2 hours and 50 minutes. The reaction mixture was concentrated under reduced pressure to give 20.0 mg of Compound 51.

The physicochemical properties of Compound 51 are as follows.

$^1$H-NMR(270 MHz, DMSO-$d_6$)δ(ppm); 12.09(1H,brs), 8.07(1H,brs), 8.03(1H,brs), 7.85(1H,d,J=7.9 Hz), 7.63(1H, d,J=15.5 Hz), 7.30(1H,d,J=8.6 Hz), 7.17(1H,d,J=15.5 Hz), 4.38–4.52(3H,m), 3.99(3H,s), 3.91(1H,brd, J=9.2 Hz), 3.84 (3H,s), 3.56(1H,dd,J=9.9, 9.3 Hz), 3.12(6H,s), 2.66(3H,s), 2.39(3H,s)

IR(KBr)ν(cm$^{-1}$); 1693, 1651, 1516, 1470, 1435, 1414, 1277, 1203, 1190, 1090

EXAMPLE 52

Synthesis of Compound 52

To 28.5 mg (0.0618 mmol) of Compound 41 was added 1.5 ml of acetonitrile, and 300 mg of 5% hydrobromic acid in methanol was added thereto. The mixture was stirred at room temperature for 50 minutes. The reaction mixture was concentrated under reduced pressure. The resulting crude product was dissolved in 1.48 ml of methylene chloride. Then, 37.4 mg (0.185 mmol) of p-nitrophenyl chloroformate and 25.8 μl (0.185 mmol) of triethylamine were added thereto at −78° C. The mixture was stirred for 40 minutes. To the reaction mixture was then added 16.4 μl (0.309 mmol) of 1-methylhydrazine, and the mixture was stirred at −78° C. to 0° C. for 1.5 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=15:1) to give 28.0 mg of Compound 52(yield: 74%).

The physicochemical properties of Compound 52 are as follows.

$^1$H-NMR (270 MHz, CDCl$_3$)δ(ppm); 9.92–10.16 (1H,br), 8.24(1H,brs), 7.80(1H,d,J=15.2 Hz), 7.24(1H,d,J=8.3 Hz), 7.16(1H,s), 6.87(1H,d,J=8.6 Hz), 6.79(1H,d,J=15.2 Hz), 4.45–4.54(1H,br), 4.47(1H,d,J=9.6 Hz), 4.40(1H,dd,J=10.2, 9.2 Hz), 3.94(3H,s), 3.93(3H,s), 3.77(1H,dd,J=9.5, 1.9 Hz), 3.28(3H,br), 3.20(1H,dd,J=9.9, 9.9 Hz), 2.84(6H,s), 2.30 (3H,s)

FABMS(m/z); 616, 614(M+H) $^+$

IR(KBr)ν(cm$^{-1}$); 1697, 1686, 1647, 1508, 1437, 1414, 1246, 1219, 1188, 1159, 1111

EXAMPLE 53

Synthesis of Compound 53

To 18.0 mg (0.0293 mmol) of Compound 52 obtained in Example 52 was added 2.0 ml of ahnydrous ethyl acetate, and 142 mg of 5% hydrobromic acid in methanol was added thereto. The mixture was stirred at −20° C. for 1 hour. The reaction mixture was concentrated under reduced pressure to give 20.7 mg of Compound 53.

The physicochemical properties of Compound 53 are as follows.

$^1$H-NMR (270 MHz, DMSO-$d_6$)δ(ppm); 12.02(1H,brs), 8.12(1H,brs), 7.97(1H,brs), 7.83(1H,d,J=8.2 Hz), 7.63(1H, d,J=14.8 Hz), 7.29(1H,d,J=8.6 Hz), 7.17(1H,d,J=15.2 Hz), 4.40–4.58(3H,br), 3.99(3H,s), 3.85(3H,s), 3.81(1H,brd,J= 10.0 Hz), 3.11(6H,s), 2.67(3H,s)

IR(KBr)ν(cm$^{-1}$); 1650, 1645, 1516, 1464, 1435, 1416, 1279, 1219, 1190, 1159, 1107, 1092

EXAMPLE 54

Synthesis of Compound 54

To 40.0 mg (0.0867 mmol) of Compound 41 were added 2.10 ml of acetonitrile and 421 mg of 5% hydrobromic acid in methanol, and the mixture was stirred at room temperature for 40 minutes. The reaction mixture was concentrated under reduced pressure. The resulting crude product was dissolved in 2.10 ml of methylene chloride. Then, 32.0 mg (0.260 mmol) of nicotinic acid and 53.7 mg (0.260 mmol) of dicyclohexylcarbodiimide were added thereto at −20° C. The mixture was stirred for 5 minutes. To the reaction mixture was added 31.8 mg (0.260 mmol) of 4-dimethylaminopyridine, and the mixture was stirred at −20° C. to 0° C. for 3 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=25:1) to give 47.4 mg of Compound 54 (yield: 84%).

The physicochemical properties of Compound 54 are as follows.

$^1$H-NMR(270 MHz, CDCl$_3$)δ(ppm); 11.79(1H,brs), 9.27 (1H,s), 8.67(1H,brs), 8.29(1H,s), 8.17(1H,d,J=7.9 Hz), 7.73 (1H,d,J=15.2 Hz), 7.26(1H,br), 7.23(1H,d,J=8.6 Hz), 7.13 (1H,s), 6.86(1H,d,J=8.3 Hz), 6.73(1H,d,J=15.2 Hz), 4.57–4.68(1H,m), 4.46(1H,d,J=9.9 Hz), 4.31(1H,dd,J=10.2, 9.2 Hz), 3.97(3H,s), 3.92(3H,s), 3.85(1H,dd,J=9.9, 2.4 Hz), 3.26(1H,dd,J=9.9, 9.9 Hz), 2.83(6H,s), 2.71(3H,s)

FABMS (m/z); 649, 647(M+H) $^+$

IR(KBr)ν(cm$^{-1}$); 1697, 1647, 1591, 1508, 1437, 1410, 1267, 1246, 1217, 1192, 1093

EXAMPLE 55

Synthesis of Compound 55

To 47.4 mg (0.0732 mmol) of Compound 54 obtained in Example 54 was added 2.6 ml of anhydrous ethyl acetate, and 355 mg of 5% hydrobromic acid in methanol was added thereto. The mixture was stirred at room temperature for 30 minutes. The reaction mixture was concentrated under reduced pressure to give 51.8 mg of Compound 55.

The physicochemical properties of Compound 55 are as follows.

$^1$H-NMR(270 MHz, DMSO-$d_6$)δ(ppm); 12.16(1H,s), 9.37(1H,s), 8.96(1H,d,J=4.3 Hz), 8.57(1H,dt, J=7.9, 2.0 Hz), 8.23(1H,brs), 8.12(1H,brs), 7.93(1H,d,J=8.3 Hz), 7.73(1H, dd,J=7.9, 5.0 Hz), 7.65(1H,d,J=15.2 Hz), 7.35(1H,d,J=8.9 Hz), 7.22(1H,d,J=15.2 Hz), 4.47–4.60(3H,br), 4.02(3H,s), 3.86(3H,s), 3.84(1H,dd,J=10.6, 2.6 Hz), 3.51(1H,dd,J=9.6, 8.6 Hz), 3.18(6H,s), 2.64(3H,s)

IR(KBr)ν(cm$^{-1}$); 1686, 1647, 1516, 1466, 1458, 1437, 1414, 1279, 1219, 1097

EXAMPLE 56

Synthesis of Compound 56

To 30.0 mg (0.065 mmol) of Compound 41 were added 1.58 ml of acetonitrile and 316 mg of 5% hydrobromic acid in methanol, and the mixture was stirred at room temperature for 40 minutes. The reaction mixture was concentrated under reduced pressure. The resulting crude product was dissolved in 1.58 ml of methylene chloride. Then, 32.2 mg (0.195 mmol) of 4-dimethylaminobenzoic acid and 40.2 mg (0.195 mmol) of dicyclohexylcarbodiimide were added thereto at −20° C. The mixture was stirred for 5 minutes. To the mixture was added 23.8 mg (0.195 mmol) of 4-dimethylaminopyridine, and the mixture was stirred at −20° C. to room temperature for 5 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=40:1) to give 57.8 mg of the crude product. Subsequently, the crude product was purified by preparative high-performance liquid chromatography (acetonitrile:water=90:10) to give 27.2 mg of Compound 56(yield: 61%).

The physicochemical properties of Compound 56 are as follows.

$^1$H-NMR(270 MHz, CDCl$_3$)δ(ppm); 9.50(1H,brs), 8.27 (1H,brs), 7.90(2H,d,J=9.2 Hz), 7.73(1H,d,J=15.2 Hz), 7.23 (1H,d,J=8.6 Hz), 7.15(1H,s), 6.86(1H,d,J=8.6 Hz), 6.74(1H, d,J=15.2 Hz), 6.50(2H,d,J=8.9 Hz), 4.48–4.58(1H,m), 4.44 (1H,d,J=10.2 Hz), 4.27(1H,dd,J=10.6, 8.4 Hz), 3.94(3H,s), 3.92(3H,s), 3.81(1H,dd,J=9.6, 2.3 Hz), 3.20(1H,dd,J=10.2, 9.9 Hz), 3.00(6H,s), 2.83(6H,s), 2.48(3H,s)

FABMS(m/z); 691, 689(M+H) $^+$

IR(KBr)ν(cm$^{-1}$); 1697, 1686, 1647, 1606, 1508, 1437, 1412, 1269, 1182, 1090

EXAMPLE 57

Synthesis of Compound 57

To 30.0 mg (0.065 mmol) of Compound 41 were added 1.58 ml of acetonitrile and 316 mg of 5% hydrobromic acid in methanol, and the mixture was stirred at room temperature for 40 minutes. The reaction mixture was concentrated under reduced pressure. The resulting crude product was dissolved in 1.58 ml of methylene chloride. Then, 27.1 mg (0.195 mmol) of 3-aminopyrazine-2-carboxylic acid and 40.2 mg (0.195 mmol) of dicyclohexylcarbodiimide were added thereto at −20° C. The mixture was stirred for 5 minutes. To the reaction mixture was added 23.8 mg (0.195 mmol) of 4-dimethylaminopyridine, and the mixture was stirred at −20° C. to room temperature for 4.5 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=25:1) to give 36.2 mg of Compound 57(yield: 84%).

The physicochemical properties of Compound 57 are as follows.

$^1$H-NMR(270 MHz, CDCl$_3$)δ(ppm); 11.47(1H,s) , 8.32 (1H,brs), 8.18(1H,d,J=2.3 Hz), 7.79(1H,d,J=2.3 Hz), 7.75 (1H,d,J=16.8 Hz), 7.21(1H,dd,J=7.3, 1.7 Hz), 7.14(1H,d,J= 2.0 Hz), 6.86(1H,d,J=8.3 Hz), 6.73(1H,d,J=15.2 Hz), 6.10–6.70(2H,br), 4.48–4.59(1H,m), 4.45(1H,d,J=10.9 Hz), 4.29(1H,dd,J=9.6, 9.2 Hz), 3.92(3H,s), 3.89(3H,s), 3.79(1H, dd,J=9.6, 2.0 Hz), 3.22(1H,dd,J=10.2, 10.2 Hz), 2.83(6H,s), 2.59(3H,s)

FABMS (m/z); 665, 663(M+H) $^+$

IR(KBr)ν(cm$^{-1}$); 1647, 1637, 1595, 1508, 1437, 1410, 1298, 1246, 1221, 1192, 1092

EXAMPLE 38

Synthesis of Compound 58

To 23.8 mg (0.0359 mmol) of Compound 57 obtained in Example 57 was added 1.65 ml of anhydrous ethyl acetate, and the 177 mg of 5% hydrobromic acid in methanol was added thereto. The mixture was stirred at room temperature for 30 minutes. The reaction mixture was concentrated under reduced pressure to give 26.4 mg of Compound 58.

The physicochemical properties of Compound 58 are as follows.

$^1$H-NMR (270 MHz, DMSO-d$_6$)δ(ppm); 12.13(1H,s), 8.41(1H,d,J=2.3 Hz), 8.14(2H,brs), 8.07(1H,d,J=2.0 Hz), 7.94(1H,d,J=8.6 Hz), 7.66(1H,d,J=15.2 Hz), 7.43(3H,br), 7.35(1H,d,J=15.2 Hz), 7.21(1H,d,J=15.2 Hz), 4.13–4.41 (3H,m), 4.02(3H,s), 3.86(3H,s), 3.84(1H,brd, J=11.2 Hz), 3.18(6H,s), 2.62(3H,s)

IR(KBr)ν(cm$^{-1}$); 1689, 1645, 1601, 1516, 1437, 1414, 1279, 1219, 1190, 1095

EXAMPLE 59

Synthesis of Compound 59

To 40.0 mg (0.0867 mmol) of Compound 41 were added 2.11 ml of acetonitrile and 421 mg of 5% hydrobromic acid in methanol, and the mixture was stirred at room temperature for 40 minutes. The reaction mixture was concentrated under reduced pressure. The resulting crude product was dissolved in 2.11 ml of methylene chloride. Then, 52.0 mg (0.258 mmol) of p-nitrophenyl chloroformate and 36.0 μl (0.258 mmol) of triethylamine were added thereto at −78° C. The mixture was stirred for 30 minutes. To the reaction mixture was added 51.8 μl (0.430 mmol) of 1-amino-4-methylpiperazine, and the mixture was stirred at 0° C. to room temperature for 7.5 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=5:1) to give 27.7 mg of Compound 59(yield: 47%).

The physicochemical properties of Compound 59 are as follows.

$^1$H-NMR (270 MHz, CDCl$_3$)δ(ppm); 10.08(1H,brs), 8.24 (1H,s), 7.77(1H,d,J=15.2 Hz) , 7.25(1H,dd,J=8.7, 1.7 Hz), 7.15(1H,d,J=1.7 Hz), 6.86(1H,d,J=8.6 Hz), 6.75(1H,d,J= 15.2 Hz), 4.45–4.55(1H,m), 4.42(1H,d,J=11.2 Hz), 4.26(1H, dd,J=10.2, 8.9 Hz), 3.92(3H,s), 3.89(3H,s), 3.74(1H,dd,J= 8.9, 1.9 Hz), 3.17(1H,dd,J=9.9, 9.9 Hz), 2.96(4H,br), 2.83 (6H,s), 2.56(3H,s), 2.49(4H,br), 2.23(3H,s)

FABMS(m/z); 685, 683(M+H) $^+$

IR(KBr)ν(cm$^{-1}$); 1697, 1645, 1591, 1508, 1446, 1414, 1246, 1215, 1190, 1088

EXAMPLE 60

Synthesis of Compound 60

To 27.7 mg (0.0405 mmol) of Compound 59 obtained in Example 59 was added 1.82 ml of anhydrous ethyl acetate, and then 262 mg of 5% hydrobromic acid in methanol was added thereto. The mixture was stirred at room temperature for 60 minutes. The reaction mixture was concentrated under reduced pressure to give 31.3 mg of Compound 60.

The physicochemical properties of Compound 60 are as follows.

$^1$H-NMR(270 MHz, DMSO-d$_6$)δ(ppm); 12.09(1H,s), 9.53(1H,br), 9.48(1H,s), 8.03(2H,brs), 7.85(1H,d,J=7.9 Hz), 7.63(1H,d,J=15.2 Hz), 7.31(1H, d, J=8.3 Hz), 7.18(1H,d, J=15.2 Hz), 4.39–4.58(3H,m), 4.00(3H,s), 3.85(3H,s), 3.80 (1H,dd,J=9.4, 2.8 Hz), 3.45(4H,br), 3.14(6H,s), 3.08–3.25 (5H,br), 2.82(3H,d,J=4.3 Hz), 2.66(3H,s)

IR(KBr)ν(cm$^{-1}$); 1743, 1689, 1649, 1516, 1464, 1435, 1416, 1279, 1219, 1190, 1094

EXAMPLE 61

Synthesis of Compound 61

To 30.0 mg (0.065 mmol) of Compound 41 were added 1.58 ml of acetonitrile and 316 mg of 5% hydrobromic acid in methanol, and the mixture was stirred at room temperature for 40 minutes. The reaction mixture was concentrated under reduced pressure. The resulting crude product was dissolved in 1.58 ml of methylene chloride. Then, 39.3 mg (0.195 mmol) of p-nitrophenyl chloroformate and 27.2 µl (0.195 mmol) of triethylamine were added thereto at –78° C. The mixture was stirred for 40 minutes. To the reaction mixture was then added 24.7 µl (0.325 mmol) of 1,1-dimethylhydrazine, and the mixture was stirred at –20° C. to room temperature for 3 hours and 40 minutes. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=20:1) to give 21.9 mg of Compound 61 (yield: 54%).

The physicochemical properties of Compound 61 are as follows.

$^1$H-NMR(270 MHz, CDCl$_3$)δ(ppm); 9.78(1H,brs), 8.23 (1H,brs), 7.80(1H,d,J=15.2 Hz), 7.25(1H,dd, J=6.3, 2.0 Hz), 7.16(1H,d,J=2.0 Hz), 7.13(1H,br), 6.87.(1H,d,J=8.6 Hz), 6.77(1H,d,J=15.2 Hz), 4.42–4.52(1H,m), 4.41(1H,d,J=9.6 Hz), 4.26(1H,dd, J=9.9, 8.9 Hz), 3.93(3H,s), 3.87(3H,s), 3.72(1H,brd,J=6.6 Hz), 3.16(1H,dd,J=9.2, 8.1 Hz), 2.84(6H, s), 2.64(6H,s), 2.48(3H,s)

FABMS(m/z); 630, 628(M+H) $^+$

IR(KBr)ν(cm$^{-1}$); 1734, 1697, 1645, 1591, 1508, 1458, 1437, 1414, 1246, 1217, 1190, 1098

EXAMPLE 62

Synthesis of Compound 62

To 15.8 mg (0.0251 mmols) of Compound 61 obtained in Example 61 was added 1.13 ml of anhydrous ethyl acetate, and then 122 mg of 5% hydrobromic acid in methanol was added thereto. The mixture was stirred at room temperature for 30 minutes. The reaction mixture was concentrated under reduced pressure to give 18.2 mg of Compound 62.

The physicochemical properties of Compound 62 are as follows.

$^1$H-NMR (270 MHz, DMSO-d$_6$)δ(ppm); 12.08(1H,s), 9.17(1H,brs), 8.02(2H,brs), 7.87(1H,d,J=8.9 Hz), 7.64(1H, d,J=15.2 Hz), 7.32(1H,d,J=8.9 Hz), 7.18(1H,d,J=15.5 Hz), 4.39–4.58(3H,m), 4.01(3H,s), 3.84(3H,s), 3.80(1H,dd,J= 9.9, 2.6 Hz), 3.15(6H,s), 2.65(6H,s), 2.61(3H,s)

IR(KBr)ν(cm$^{-1}$); 1749, 1695, 1684, 1647, 1516, 1471, 1437, 1414, 1277, 1219, 1095

EXAMPLE 63

Synthesis of Compound 63

To 30.0 mg (0.065 mmol) of Compound 41 were added 1.58 ml of acetonitrile and 316 mg of 5% hydrobromic acid in methanol, and the mixture was stirred at room temperature for 40 minutes. The reaction mixture was concentrated under reduced pressure. The resulting crude product was dissolved in 1.40 ml of methylene chloride. Then, 39.3 mg (0.195 mmol) of p-nitrophenyl chloroformate and 27.2 µl (0.195 mmol) of triethylamine were added thereto at –78° C. The mixture was stirred for 40 minutes. To the mixture were added 43.2 mg (0.325 mmol) of 1,2-dimethylhydrazine dihydrochloride and 90.6 µl (0.65 mmol) of triethylamine dissolved in 0.2 ml of chloroform, and the mixture was stirred at –20° C. for 2 hours and 50 minutes. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=30:1) to give 35.0 mg of Compound 63 (yield: 86%).

The physicochemical properties of Compound 63 are as follows.

$^1$H-NMR(270 MHz, CDCl$_3$)δ(ppm); 9.87(1H,brs), 9.63 (1H,brs), 8.22(1H,s), 7.79(1H,d,J=15.5 Hz), 7.26(1H,dd,J= 8.3, 2.0 Hz), 7.17(1H,d,J=1.7 Hz), 6.88(1H, d,J=8.6 Hz), 6.78(1H,d,J=15.2 Hz), 4.42–4.55(1H,br), 4.47(1H,d,J=10.2 Hz), 4.34(1H,dd, J=9.2, 9.2 Hz), 3.94(3H,s), 3.93(3H,s), 3.77(1H,dd,J=9.6, 2.0 Hz), 3.26(3H,brs), 3.19(1H,dd,J= 10.2, 9.9 Hz), 2.85(6H,s), 2.69(3H,s), 2.36(3H,brs)

FABMS(m/z); 630, 628(M+H) $^+$

IR(KBr)ν(cm$^{-1}$); 1697, 1647, 1591, 1508, 1458, 1435, 1414, 1246, 1219, 1190, 1157, 1109

EXAMPLE 64

Synthesis of Compound 64

To 25.8 mg (0.0410 mmol) of Compound 63 obtained in Example 63 was added 1.85 ml of anhydrous ethyl acetate, and then 199 mg of 5% hydrobromic acid in methanol was added thereto. The mixture was stirred at room temperature for 30 minutes. The reaction mixture was concentrated under reduced pressure to give 28.2 mg of Compound 64.

The physicochemical properties of Compound 64 are as follows.

$^1$H-NMR (270 MHz, DMSO-d$_6$)δ(ppm); 12.04(1H,s), 8.12(2H,brs), 7.92(1H,d,J=8.6 Hz), 7.64(1H,d,J=15.2 Hz), 7.35(1H,d,J=8.6 Hz), 7.20(1H,d,J=15.5 Hz), 4.39–4.60(3H, m), 4.02(3H,s), 3.85(3H,s), 3.81(1H,brd, J=10.7 Hz), 3.19 (6H,s), 2.67(3H,s), 2.50(3H,s)

IR(KBr)ν(cm$^{-1}$); 1695, 1651, 1645, 1516, 1471, 1441, 1435, 1416, 1279, 1219, 1107

EXAMPLE 65

Synthesis of Compound 65

To 25.0 mg (0.0542 mmol) of Compound 41 were added 1.32 ml of acetonitrile and 351 mg of 5% hydrobromic acid in methanol, and the mixture was stirred at room temperature for 30 minutes. The reaction mixture was concentrated under reduced pressure. The resulting crude product was dissolved in 1.32 ml of methylene chloride. Then, 38.1 mg (0.163 mmol) of 4-(4-methylpiperazinylmethyl)benzoic acid and 31.2 mg (0.163 mmol) of N-ethyl-N'-3-dimethylaminopropyl carbodiimide hydrochloride were added thereto at −20° C. The mixture was stirred for 5 minutes. To the mixture was then added 19.9 mg (0.163 mmol) of 4-dimethylaminopyridine, and the mixture was stirred at −20° C. to room temperature for 6 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=10:1) to give 25.0 mg of Compound 65(yield: 61%).

The physicochemical properties of Compound 65 are as follows.

$^1$H-NMR(270 MHz, CDCl$_3$)δ(ppm); 9.27(1H,brs), 8.32 (1H,brs), 8.07(2H,d,J=8.3 Hz), 7.73(1H,d,J=15.2 Hz), 7.38 (2H,d,J=8.2 Hz), 7.22(1H,dd,J=8.2, 2.0 Hz), 7.13(1H,d,J= 2.0 Hz), 6.86(1H,d,J=8.6 Hz), 6.73(1H,d,J=15.2 Hz), 4.48–4.60(1H,m), 4.45(1H,d,J=10.6 Hz), 4.29(1H,dd,J=9.5, 8.9 Hz), 3.95(3H,s), 3.92(3H,s), 3.80(1H,dd,J=9.6, 2.3 Hz), 3.53(2H,s), 3.21(1H,dd,J=10.2, 9.9 Hz), 2.83(6H,s), 2.60 (3H,s), 2.48(8H,br), 2.30(3H,s)

FABMS (m/z); 760, 758(M+H) $^+$

IR(KBr)ν(cm$^{-1}$); 1740, 1697, 1647, 1508, 1446, 1412, 1248, 1217, 1192, 1140, 1090

EXAMPLE 66

Synthesis of Compound 66

To 18.0 mg (0.0237 mmol) of Compound 65 obtained in Example 65 was added 1 ml of anhydrous ethyl acetate, and then 153 mg of 5% hydrobromic acid in methanol was added thereto. The mixture was stirred at room temperature for 30 minutes. The reaction mixture was concentrated under reduced pressure to give 22.9 mg of Compound 66.

The physicochemical properties of Compound 66 are as follows.

$^1$H-NMR(270 MHz, DMSO-d$_6$)δ(ppm); 12.14(1H,s), 9.51(1H,br), 8.21(2H,d,J=8.3 Hz), 8.19(1H,d,J=15.2 Hz), 7.75–7.89(2H,br), 7.63(2H,d,J=8.9 Hz), 7.60(1H,d,J=5.9 Hz), 7.24(1H,d,J=8.6 Hz), 7.16(1H,d,J=15.5 Hz), 4.45–4.58 (3H,br), 3.97(3H,s), 3.86(3H,s), 3.83(1H,brd, J=9.7 Hz), 3.06(8H,br), 2.81(3H,s), 2.63(3H,s)

IR(KBr)ν(cm$^{-1}$); 1734, 1695, 1647, 1616, 1516, 1437, 1412, 1263, 1217, 1092, 1018

EXAMPLE 67

Synthesis of Compound 67

To 10.0 mg (0.0238 mmol) of Compound 6 were added 0.4 ml of acetonitrile and 5.6 μl of 48% hydrobromic acid, and the mixture was stirred at room temperature for 50 minutes. The reaction mixture was concentrated under reduced pressure. The resulting crude product was dissolved in 0.26 ml of methylene chloride. Then, 6.1 mg (0.0495 mmol) of nicotinic acid and 0.10 ml of methylene chloride containing 20.4 mg (0.099 mmol) of dicyclohexylcarbodiimide were added thereto at −20° C. The mixture was stirred for 5 minutes. To the reaction mixture was then added 6.1 mg (0.0495 mmol) of 4-dimethylaminopyridine, and the mixture was stirred at −20° C. to room temperature for 18 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=25:1) to give 10.9 mg of Compound 67(yield: 76%).

The physicochemical properties of Compound 67 are as follows.

$^1$H-NMR(270 MHz, CDCl$_3$)δ(ppm); 11.44(1H,brs), 9.32 (1H,s), 8.73(1H,d,J=4.9 Hz), 8.71(2H,s), 8.31(1H,s), 8.23 (1H,d,J=8.3 Hz), 7.64(1H,d,J=15.5 Hz), 7.35(1H,dd,J=7.9, 4.9 Hz), 6.90(1H,d,J=15.5 Hz), 4.59–4.69(1H,m), 4.46(1H, d,J=10.6 Hz), 4.34(1H,dd,J=10.6, 8.9 Hz), 4.06(3H,s), 3.97 (3H,s), 3.86(1H,dd,J=9.5, 2.6 Hz), 3.31(1H,dd,J=10.2, 9.9 Hz), 2.71(3H,s)

FABMS (m/z); 608, 606(M+H) $^+$

IR(KBr)ν(cm$^{-1}$); 1697, 1653, 1593, 1475, 1435, 1412, 1335, 1271, 1219, 1093

EXAMPLE 68

Synthesis of Compound 68

To 40.0 mg (0.0951 mmol) of Compound 6 were added 2.32 ml of acetonitrile and 41.6 μl of 6.86N hydrogen chloride in ethanol, and the mixture was stirred at room temperature for 40 minutes. The reaction mixture was concentrated under reduced pressure. The resulting crude product was dissolved in 2.32 ml of methylene chloride. Then, 57.5 mg (0.285 mmol) of p-nitrophenyl chloroformate and 53 μl (0.380 mmol) of triethylamine were added thereto at −78° C. The mixture was stirred for 50 minutes. To the reaction mixture was then added 57.2 μl (0.476 mmol) of 1-amino-4-methylpiperazine, and the mixture was stirred at −78° C. to 0° C. for 24 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=6:1) to give 19.5 mg of Compound 68(yield: 34%).

The physicochemical properties of Compound 68 are as follows.

$^1$H-NMR(270 MHz, CDCl$_3$)δ(ppm); 9.67(1H,brs), 8.73 (2H,s), 8.20(1H,brs), 7.66(1H,d,J=15.2 Hz), 7.12(1H,br), 6.90(1H,d,J=15.5 Hz), 4.40–4.47(1H,br), 4.39(1H,d,J=10.2 Hz), 4.21(1H,dd,J=9.4, 8.9 Hz), 4.06(3H,s), 3.88(3H,s), 3.85(1H,br), 3.35(1H,dd,J=10.9, 9.4 Hz), 2.95(4H,br), 2.51 (7H,br), 2.26(3H,s)

FABMS(m/z); 600, 598(M+H) $^+$

IR(KBr)ν(cm$^{-1}$); 1743, 1697, 1653, 1593, 1475, 1437, 1412, 1338, 1215, 1090

EXAMPLE 69

Synthesis of Compound 69

To 16.2 mg (0.0271 mmol) of Compound 68 obtained in Example 68 was added 1.22 ml of anhydrous ethyl acetate, and then 7.9 µl of 6.86N hydrogen chloride in ethanol was added thereto. The mixture was stirred at −20° C. for 20 minutes. The reaction mixture was concentrated under reduced pressure to give 15.5 mg of Compound 69.

The physicochemical properties of Compound 69 are as follows.

$^1$H-NMR(270 MHz, DMSO-$d_6$)δ(ppm); 12.15(1H,brs), 10.21–10.28(1H,br),9.51(1H,s), 9.09(2H,s), 8.04(1H,s), 7.60(1H,d,J=15.5 Hz), 7.38(1H,d,J=15.2Hz), 4.52(1H,d,J=10.9 Hz), 4.31–4.49(2H,m), 3.97(3H,s), 3.85(1H,brd, J=10.9 Hz), 3.83(3H,s), 3.53(1H,dd,J=10.4, 9.9 Hz), 3.05–3.29(8H,m), 2.78(3H,brd, J=3.3 Hz), 2.66(3H,s)

IR(KBr)ν(cm$^{-1}$); 1691, 1686, 1653, 1649, 1595, 1475, 1458, 1437, 1414, 1215, 1190

EXAMPLE 70

Synthesis of Compound 70

To 80 mg (0.190 mmol) of Compound 6 were added 4.0 ml of acetonitrile and 922 mg of 5% hydrobromic acid in methanol, and the mixture was stirred at room temperature for 40 minutes. The reaction mixture was concentrated under reduced pressure. The resulting crude product was dissolved in a mixed solvent of 3.0 ml of methylene chloride and 1.13 ml of toluene. Then, 115 ml (0.570 mmol) of p-nitrophenyl chloroformate and 106 µl (0.760 mmol) of triethylamine were added thereto at −78° C. The mixture was stirred for 100 minutes. To the reaction mixture was then added 114 µl (0.95 mmol) of 1-amino-4-methylpiperazine, and the mixture was stirred at −20° C. to room temperature for 17 hours and 40 minutes. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform: methanol:triethylamine= 9:1:0.2) to give 45 mg of a crude product. The crude product was then purified by column chromatography (chloroform:methanol:triethylamine=150:15:1) to give 33.9 mg of Compound 70(yield: 28%).

The physicochemical properties of Compound 70 are as follows.

$^1$H-NMR(270 MHz, CDCl$_3$)δ(ppm); 9.37(1H,brs), 8.74 (2H,s), 8.23(1H,brs), 7.69(1H,d,J=15.5 Hz), 6.91(1H, d,J= 15.5 Hz), 6.70(1H,br), 4.50–4.60(1H,m), 4.41(1H,d,J=10.6 Hz), 4.27(1H,dd,J=9.6, 9.2 Hz), 4.07(3H,s), 3.93(3H,s), 3.78(1H,dd,J=9.9, 2.3 Hz), 3.22(1H,dd,J=9.9, 9.2 Hz), 2.97 (4H,br), 2.61(3H,s), 2.58(4H,br), 2.30(3H,s)

FABMS (m/z); 644, 642(M+H) $^+$

IR(KBr)ν(cm$^{-1}$); 1703, 1695, 1651, 1593, 1473, 1456, 1435, 1412, 1338, 1271, 1215, 1190, 1090

EXAMPLE 71

Synthesis of Compound 71

To 14.0 mg (0.0218 mmol) of Compound 70 obtained in Example 70 was added 0.98 ml of anhydrous ethyl acetate, and then 6.4 µl of 6.86N hydrogen chloride in ethanol was added thereto. The mixture was stirred at −20° C. for 20 minutes. To the reaction mixture was added diethyl ether, and the mixture was concentrated under reduced pressure to give 14.4 mg of Compound 71.

The physicochemical properties of Compound 71 are as follows.

$^1$H-NMR (270 MHz, DMSO-$d_6$)δ(ppm); 12.13(1H,brs), 10.04(1H,br), 9.50(1H,s), 9.09(2H,s), 8.04(1H,s), 7.60(1H, d,J=15.2 Hz), 7.37(1H,d,J=15.5 Hz), 4.37–4.57(2H,m), 4.47 (1H,d,J=10.2 Hz), 3.97(3H,s), 3.85(3H,s), 3.80(1H,brd, J=10.8 Hz), 3.43(1H,dd,J=9.2, 8.6 Hz), 3.00–3.30(8H,m), 2.80(3H,s), 2.66(3H,s)

IR(KBr)ν(cm$^{-1}$); 1736, 1697, 1653, 1595, 1473, 1458, 1411, 1340, 1219, 1092

EXAMPLE 72

Synthesis of Compound 72

To 33.9 mg (0.0528 mmol) of Compound 70 obtained in Example 70 was added 2.0 ml of anhydrous ethyl acetate, and then 171 mg of 5% hydrobromic acid in methanol was added thereto. The mixture was stirred at −20° C. for 20 minutes. To the reaction mixture was added diethyl ether, and the mixture was concentrated under reduced pressure to give 36.8 mg of Compound 72.

The physicochemical properties of Compound 72 are as follows.

$^1$H-NMR (270 MHz, DMSO-$d_6$)δ(ppm); 12.09(1H,brs), 9.58(1H,brs), 9.48(1H,brs), 9.08(2H,s), 8.04(1H,s), 7.60 (1H,d,J=15.8 Hz), 7.37(1H,d,J=15.5 Hz), 4.37–4.57(2H,m), 4.47(1H,d,J=10.2 Hz), 3.97(3H,s), 3.85(3H,s), 3.79(1H,brd, J=9.6 Hz), 3.00–3.30(7H,br), 2.80(3H,s), 2.66(3H,s)

IR(KBr)ν(cm$^{-1}$); 1747, 1697, 1653, 1595, 1475, 1437, 1414, 1340, 1219, 1093

EXAMPLE 73

Synthesis of Compound 73

To 29.6 mg (0.0704 mmol) of Compound 6 were added 1.27 ml of acetonitrile and 342 mg of 5% hydrobromic acid in methanol, and the mixture was stirred at room temperature for 45 minutes. The reaction mixture was concentrated under reduced pressure. The resulting crude product was dissolved in 1.7 ml of methylene chloride. Then, 28.8 ml (0.218 mmol) of thiodiglycolic anhydride and 27.5 mg (0.225 mmol) of 4-dimethylaminopyridine were added thereto at 0° C. The mixture was stirred at 0° C. for 3 hours. To the reaction mixture was added a 0.01M phosphate buffer of pH7, and the resulting solution was extracted with chloroform. The chloroform layer was washed with a saturated aqueous solution of sodium chloride, dried over anhydrous sodium sulfate, and then concentrated under reduced pressure. The obtained crude product was purified by thin-layer chromatography (chloroform:methanol:acetic acid=8:1:0.1) to give 23.6 mg of Compound 73(yield: 53%).

The physicochemical properties of Compound 73 are as follows.

$^1$H-NMR(270 MHz, CDCl$_3$+CD$_3$OD)δ(ppm); 8.49(2H, s), 8.06(1H,s), 7.24(1H,d,J=13.2 Hz), 6.64(1H,d,J=15.5 Hz), 4.37–4.47(1H,m), 4.23(1H,d,J=10.4 Hz), 4.17(1H,dd,J= 10.9, 8.3 Hz), 3.98(3H,s), 3.85(3H,s), 3.69(1H,dd,J=9.6, 2.3 Hz), 3.64(2H,s), 3.34(2H,s), 3.24(1H,dd,J=10.2, 8.9 Hz), 2.47(3H,s)

FABMS(m/z); 635, 633(M+H) $^+$

IR(KBr)ν(cm$^{-1}$); 1697, 1657, 1597, 1477, 1435, 1414, 1338, 1273, 1219, 1109

EXAMPLE 74

Synthesis of Compound 74

To 25.2 mg (0.0599 mmol) of Compound 6 were added 1.45 ml of acetonitrile and 291 mg of 5% hydrobromic acid in methanol, and the mixture was stirred at room temperature for 50 minutes. The reaction mixture was concentrated under reduced pressure. The resulting crude product was dissolved in a mixed solvent of 1.0 ml of methylene chloride and 0.45 ml of toluene. Then, 36.2 ml (0.180 mmol) of p-nitrophenyl chloroformate and 25 µl (0.180 mmol) of triethylamine were added thereto at −78° C. The mixture was stirred for 35 minutes. To the mixture was then added 15.9 µl (0.3 mmol) of 1-methylhydrazone, and the mixture was stirred at −78° C. to 0° C. for 2 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=9:1) to give 22.5 mg of Compound 74(yield: 66%).

The physicochemical properties of Compound 74 are as follows.

$^1$H-NMR(270 MHz, CDCl$_3$+CD$_3$OD)δ(ppm); 8.62(2H, s), 8.11(1H,s), 7.45(1H,d,J=15.5 Hz), 6.82(1H,d,J=15.5 Hz), 4.39–4.51(1H,m), 4.34(1H,d,J=10.2 Hz), 4.21(1H, dd,J=9.9, 9.2 Hz), 4.01(3H,s), 3.89(3H,s), 3.74(1H,dd,J=9.7, 2.5 Hz), 3.24(1H,dd,J=10.2, 9.9 Hz), 3.11(3H,s), 2.54(3H,s)

FABMS (m/z); 575, 573(M+H)$^+$

IR(KBr)ν(cm$^{-1}$); 1697, 1653, 1593, 1475, 1433, 1412, 1338, 1271, 1219, 1161, 1111, 1090

EXAMPLE 75

Synthesis of Compound 75

To 30.0 mg (0.0714 mmol) of Compound 6 were added 1.73 ml of acetonitrile and 347 mg of 5% hydrobromic acid in methanol, and the mixture was stirred at room temperature for 40 minutes. The reaction mixture was concentrated under reduced pressure. The resulting crude product was dissolved in a mixed solvent of 1.3 ml of methylene chloride and 0.43 ml of toluene. Then, 50.2 ml (0.214 mmol) of 4-(4-methylpiperazinylmethyl) benzoate and 44.2 mg (0.214 mmol) of dicyclohexylcarbodiimide were added thereto at −20° C. The mixture was stirred for 5 minutes. To the mixture was then added 26.2 ml (0.214 mmol) of 4-dimethylaminopyridine, and the mixture was stirred at from −20° C. to room temperature for 21 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=6:1) to give 25.7 mg of Compound 75(yield: 50%).

The physicochemical properties of Compound 75 are as follows.

$^1$H-NMR(270 MHz, CDCl$_3$)δ(ppm); 9.33(1H,brs), 8.68 (2H,s), 8.30(1H,brs), 8.07(2H,d,J=8.3 Hz), 7.61(1H,d,J= 15.5 Hz), 7.40(2H,d,J=8.3 Hz), 6.88(1H,d,J=15.2 Hz), 4.48–4.61(1H,m), 4.42(1H,d,J=9.9 Hz), 4.27(1H,dd,J=9.6, 8.9 Hz), 4.04(3H,s), 3.95(3H,s), 3.81(1H,dd,J=9.6, 2.6 Hz), 3.54(2H,s), 3.25(1H,dd, J=10.2, 9.6 Hz), 2.60(3H,s), 2.48 (8H,br), 2.30(3H,s)

FABMS (m/z); 719, 717(M+H)$^+$

IR(KBr)ν(cm$^{-1}$); 1738, 1697, 1657, 1593, 1475, 1435, 1412, 1336, 1265, 1217, 1090

EXAMPLE 76

Synthesis of Compound 76

To 24.2 mg (0.0337 mmol) of Compound 75 obtained in Example 75 was added 2.46 ml of anhydrous ethyl acetate, and then 136 mg of 5% hydrobromic acid in methanol was added thereto. The mixture was stirred at room temperature for 15 minutes. To the reaction mixture was added diethyl ether, and the mixture was concentrated under reduced pressure to give 26.6 mg of Compound 76.

The physicochemical properties of Compound 76 are as follows.

$^1$H-NMR(270 MHz, DMSO-d$_6$)δ(ppm); 12.15(1H,brs), 9.49(1H,br), 9.08(2H,s), 8.22(2H,d,J=8.3 Hz), 8.16(1H,s), 7.63(2H,d,J=8.3 Hz), 7.60(1H,d,J=15.2 Hz), 7.37(1H,d,J= 15.8 Hz), 4.41–4.50(3H,m), 3.97(3H,s), 3.86(3H,s), 3.82 (1H,brd, J=9.4 Hz), 2.95–3.20(3H,br), 2.82(3H,s), 2.63(3H, s)

IR(KBr)ν(cm$^{-1}$); 1736, 1697, 1653, 1593, 1475, 1435, 1412, 1338, 1265, 1219, 1092

EXAMPLE 77

Synthesis of Compound 77

To 32.8 mg (0.0760 mmol) of Compound 27 were added 1.28 ml of acetonitrile and 25.8 µl of 48% hydrobromic acid, and the mixture was stirred at room temperature for 40 minutes. The reaction mixture was concentrated under reduced pressure. The resulting crude product was dissolved in 1.15 ml of methylene chloride. Then, 28.1 mg (0.228 mmol) of nicotinic acid and 94.1 mg (0.456 mmol) of dicyclohexylcarbodiimide were added thereto at −20° C. The mixture was stirred for 5 minutes. Subsequently, to the mixture was added 27.9 mg (0.228 mmol) of 4-dimethylaminopyridine, and the mixture was stirred at −20° C. to room temperature for 15 hours. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methano=20:1) to give 28.5 mg of a crude product. The crude product was purified by preparative high-performance liquid chromatography [acetonitrile:0.05-M phosphate buffer (pH 5.9)=70:30] to give 22.1 mg of Compound 77(yield: 47%).

The physicochemical properties of Compound 77 are as follows.

$^1$H-NMR (270 MHz, CDCl$_3$)δ(ppm); 11.54(1H,brs), 9.29 (1H,d,J=1.7 Hz), 8.68(1H,dd, J=5.0, 1.7 Hz), 8.31(1H,brs), 8.20(1H,dt,J=7.9, 2.0 Hz), 7.74(1H,d,J=15.2 Hz), 7.49(2H, d,J=8.9 Hz), 7.28(1H,dd,J=7.9, 5.0 Hz), 6.69(2H,d,J=8.6 Hz), 6.68(1H,d,J=15.5 Hz), 4.56–4.66(1H,m), 4.46(1H,d,J= 10.6 Hz), 4.29(1H,dd,J=9.6, 8.9 Hz), 3.98(3H,s), 3.85(1H, dd,J=9.6, 2.3 Hz), 3.26(1H,dd,J=10.2, 9.9 Hz), 3.03(6H,s), 2.72(3H,s)

FABMS (m/z); 619, 617(M+H)$^+$

IR(KBr)ν(cm$^{-1}$); 1699, 1645, 1589, 1524, 1435, 1408, 1352, 1267, 1217, 1184, 1093

EXAMPLE 78

Synthesis of Compound 78

To 42.4 mg (0.0983 mmol) of Compound 27 were added 2.39 ml of acetonitrile and 33.4 μl of 48% hydrobromic acid, and the mixture was stirred at room temperature for 50 minutes. The reaction mixture was concentrated under reduced pressure. The resulting crude product was dissolved in a mixed solvent of 2.09 ml of methylene chloride and 0.82 ml of toluene. Then, 59.4 mg (0.295 mmol) of p-nitrophenyl chloroformate and 41.1 μl (0.295 mmol) of triethylamine were added thereto at −78° C. The mixture was stirred for 80 minutes. Subsequently, to the mixture was added 38.2 μl (0.344 mmol) of N-methylpiperazine, and the mixture was stirred at −78° C. to 0° C. for 40 minutes. To the reaction mixture was added a saturated aqueous solution of sodium hydrogen carbonate, and the resulting solution was extracted with chloroform. The chloroform layer was washed with a saturated aqueous solution of sodium hydrogen carbonate and with a saturated aqueous solution of sodium chloride, dried over anhydrous sodium sulfate, and then concentrated under reduced pressure. The obtained crude product was purified by thin-layer chromatography (chloroform:methanol=20:1) to give 14.8 mg of a crude product of Compound 78. The crude product was purified by preparative high-performance liquid chromatography [acetonitrile:0.05-M phosphate buffer (pH 5.9)=70:30] to give 14.0 mg of Compound 78(yield: 22%).

The physicochemical properties of Compound 78 are as follows.

$^1$H-NMR(270 MHz, CDCl$_3$)δ(ppm); 9.25(1H,s), 8.23 (1H,brs), 7.79(1H,d,J=15.2 Hz), 7.51(2H,d,J=8.6 Hz), 6.71 (1H,d,J=14.2 Hz), 6.70(2H,d,J=9.2 Hz), 4.53(1H,m), 4.46 (1H,d,J=10.9 Hz), 4.30(1H,dd,J=9.6, 9.2 Hz), 3.95(3H,s), 3.80(1H,dd,J=9.9, 2.3 Hz), 3.75(2H,br), 3.62(2H,br), 3.21 (1H,dd,J=10.2, 10.2 Hz), 3.03(6H,s), 2.52(3H,s), 2.49(4H, br), 2.35(3H,s)

FABMS(m/z); 640, 638(M+H)$^+$

IR(KBr)ν(cm$^{-1}$); 1716, 1699, 1591, 1524, 1431, 1406, 1354, 1215, 1093

EXAMPLE 79

Synthesis of Compound 79

To 16.0 mg (0.025 mmol) of Compound 78 obtained in Example 78 were added 0.76 ml of ethanol and 0.38 ml of methanol, and then 10.9 μl of 6.86N hydrogen chloride in ethanol was added thereto. The mixture was stirred at room temperature for 2 hours. The reaction mixture was concentrated under reduced pressure to give 16.9 mg of Compound 79.

The physicochemical properties of Compound 79 are as follows.

$^1$H-NMR (270 MHz, DMSO-d$_6$)δ(ppm); 12.19(1H,s), 11.05(1H,br), 8.09(1H,s), 7.63(2H,d,J=8.6 Hz), 7.54(1H,d, J=15.2 Hz), 6.91(1H,d,J=15.2 Hz), 6.80(2H,d,J=7.9 Hz), 4.33–4.55(4H,br), 4.13–4.17(1H,br), 3.78(3H,s), 3.25–3.62 (5H,m), 3.00(6H,s), 2.83(3H,brd, J=3.6 Hz), 2.68(3H,s)

IR(KBr)ν(cm$^{-1}$); 1716, 1699, 1647, 1589, 1508, 1437, 1217, 1093

EXAMPLE 80

Synthesis of Compound 80

To 24.7 mg (0.0535 mmol) of Compound 41 were added 1.35 ml of ethyl acetate and 39.0 μl of 6.86N hydrogen chloride in ethanol. The mixture was stirred at room temperature for 50 minutes. The reaction mixture was concentrated under reduced pressure to give 26.1 mg of Compound 80.

The physicochemical properties of Compound 80 are as follows.

$^1$H-NMR (270 MHz, DMSO-d$_6$)δ(ppm); 11.92(1H,s), 10.13(1H,brs), 8.07(1H,brs), 7.91(1H,s), 7.86(1H,d,J=8.3 Hz), 7.62(1H,d,J=15.5 Hz), 7.30(1H,d,J=8.6 Hz), 7.18(1H, d,J=15.5 Hz), 4.28–4.47(3H,br), 3.99(3H,s), 3.86(1H,brd, J=10.6 Hz), 3.80(3H,s), 3.13(6H,s), 2.60(3H,s)

IR(KBr)ν(cm$^{-1}$); 1693, 1651, 1591, 1516, 1462, 1435, 1416, 1352, 1277, 1213, 1093

EXAMPLE 81

Synthesis of Compound 81

To 25.5 mg (0.0553 mmol) of Compound 41 was added 1.39 ml of ethyl acetate, and then 447 mg of 5% hydrobromic acid in methanol were added thereto. The mixture was stirred at room temperature for 40 minutes. The reaction mixture was concentrated under reduced pressure to give 32.6 mg of Compound 81.

The physicochemical properties of Compound 81 are as follows.

$^1$H-NMR(270 MHz, DMSO-d$_6$)δ(ppm); 11.88(1H,s), 10.12(1H,brs), 8.10(1H,s), 7.88–7.90(2H,m), 7.64(1H, d, J=15.2 Hz), 7.34(1H,d,J=8.9 Hz), 7.18(1H,d,J=15.5 Hz), 4.32–4.46(3H,br), 4.02(3H,s), 3.81(3H,s), 3.76(1H,brd, J=7.6 Hz), 3.33(1H,dd,J=9.2, 8.3 Hz), 3.18(6H,s), 2.60(3H, s)

IR(KBr)ν(cm$^{-1}$); 1684, 1635, 1516, 1458, 1437, 1417, 1358, 1277, 1217, 1092

EXAMPLE 82

Synthesis of Compound 82

To 30.0 mg (0.0650 mmol) of Compound 41 were added 1.58 ml of acetonitrile and 316 mg of 5% hydrobromic acid in methanol, and the mixture was stirred at room temperature for 40 minutes. The reaction mixture was concentrated under reduced pressure. The resulting crude product was dissolved in 1.58 ml of methylene chloride. Then, 45.1 ml (0.195 mmol) of 2-(4-methylpiperazinyl)acetic acid dihydrochloride and 37.3 mg (0.195 mmol) of N-ethyl-N'-3-dimethylaminopropylcarbodiimide hydrochloride were added thereto at −20° C. The mixture was stirred for 5 minutes. To the mixture was then added 47.6 mg (0.390 mmol) of 4-dimethylaminopyridine, and the mixture was stirred at −20° C. for 4 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, and dried over anhydrous sodium sulfate. Trifluoroacetic acid was then added thereto, and the mixture was concentrated under reduced pressure. To the resulting crude product were added 2.00 ml of anhydrous ethyl acetate and 526 mg of 5% hydrobromic acid in methanol, and the mixture was stirred at room temperature for 1 hour. To the reaction mixture were added 1.5 ml of diethyl ether and 0.5 ml of diisopropyl ether, and the precipitated crystals were collected by filtration. These crystals were washed with ethyl acetate, and dried under reduced pressure to give 31.0 mg of Compound 82(yield: 52%).

The physicochemical properties of Compound 82 are as follows.

$^1$H-NMR (270 MHz, DMSO-$d_6$)δ(ppm); 12.11(1H,s), 9.55(1H,brs), 8.17(1H,s), 8.10(1H,s), 7.94(1H,d,J=8.9 Hz), 7.63(1H,d,J=15.2 Hz), 7.36(1H,d,J=8.9 Hz), 7.22(1H,d,J= 15.5 Hz), 3.85–4.60(3H,m), 4.03(3H,s), 3.94(2H,s), 3.85 (3H,s), 3.79–3.81(1H,m), 3.40–3.53(3H,m), 3.20(6H,s), 3.05–3.25(4H,br), 2.76–2.89(5H,br), 2.67(3H,s)

IR(KBr)ν(cm$^{-1}$); 1695, 1684, 1653, 1516, 1446, 1412, 1358, 1279, 1221, 1188, 1107

EXAMPLE 83

Synthesis of Compound 83

To 30.0 mg (0.0650 mmol) of Compound 41 were added 1.58 ml of acetonitrile and 316 mg of 5% hydrobromic acid in methanol, and the mixture was stirred at room temperature for 40 minutes. The reaction mixture was concentrated under reduced pressure. The resulting crude product was dissolved in 1.58 ml of methylene chloride. Then, 58.4 mg (0.195 mmol) of 2-(4-piperidinopiperidino)acetic acid dihydrochloride and 37.3 mg (0.195 mmol) of N-ethyl-N'-3-dimethylaminopropylcarbodiimide hydrochloride were added thereto at –20° C. The mixture was stirred for 5 minutes. To the mixture was then added 47.6 mg (0.390 mmol) of 4-dimethylaminopyridine, and the mixture was stirred at from –20° C. to room temperature for 4.5 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, and dried over anhydrous sodium sulfate. Trifluoroacetic acid was then added thereto, and the mixture was concentrated under reduced pressure. To the resulting crude product were added 2.00 ml of anhydrous ethyl acetate and 526 mg of 5% hydrobromic acid in methanol, and the mixture was stirred at –20° C. for 2 hours and 10 minutes. The precipitated crystals were collected by filtration, washed with ethyl acetate, and dried under reduced pressure to give 56.7 mg of Compound 83 (yield: 88%).

The physicochemical properties of Compound 83 are as follows.

$^1$H-NMR(270 MHz, DMSO-$d_6$)δ(ppm); 12.23(1H,s), 9.46(1H,brs), 8.20(1H,s), 7.91(1H,br), 7.77(1H,br), 7.62 (1H,d,J=15.2 Hz), 7.26(1H,d,J=9.2 Hz), 7.16(1H, d,J=15.8 Hz), 4.38–4.62(3H,m), 3.98(3H,s), 3.85(3H,s), 3.80(1H,m), 3.43–3.70(5H,m), 3.08(6H,s), 2.90–3.20(4H,br), 2.69(3H, s), 2.19–2.37(2H,m), 1.67–2.12(7H,m), 1.41–1.49(1H,m)

IR(KBr)ν(cm$^{-1}$); 1767, 1684, 1645, 1516, 1439, 1412, 1354, 1279, 1182, 1138, 1107

Industrial Availability

According to the present invention, provided are Compounds (I) and pharmaceutically acceptable salts thereof which have excellent anti-tumor activity, and are useful as anti-tumor agents.

We claim:
1. A DC-89 derivative represented by the formula:

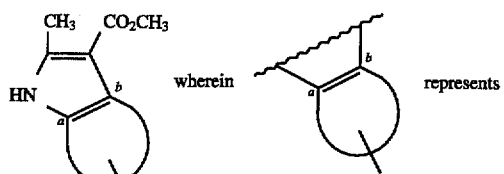

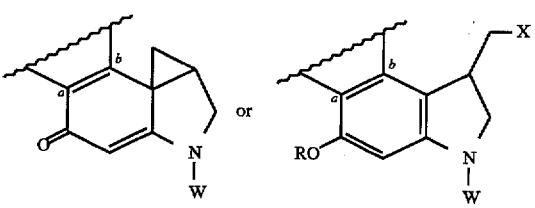

in which X represents Cl or Br, R reprsents hydrogen or COR$^1$ in which R$^1$ represents hydrogen, substituted or unsubstituted lower alkyl (wherein the substituted lower alkyl is substituted with 1 to 3 moieties selected from the group consisting of lower alkoxy, lower alkylthio optionally substituted with carboxy, carboxy, lower alkoxycarbonyl, amino, mono- or di(lower alkyl)amino, cyclic amino optionally substituted with lower alkyl or cyclic amino, halogen and phenyl), substituted or unsubstituted C$_{6-10}$ nonheterocyclic aryl, substituted or unsubstituted heterocyclic group selected from the group consisting of pyridyl, pyrazinyl and pyrimidinyl (wherein the substituted aryl and substituted heterocyclic group are substituted with 1 to 3 moieties independently selected from the group consisting of substituted or unsubstituted lower alkyl, lower alkoxy, lower alkoxycarbonyl, amino, mono- or di(lower alkyl)amino and halogen), NR$^2$R$^3$(in which R$^2$ and R$^3$ independently represent hydrogen or substituted or unsubstituted lower alkyl, amino, or mono- or di(lower alkyl) amino),

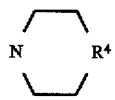

(in which R$^4$ represents oxygen, N—R$^5$(in which R$^5$ represents hydrogen or lower alkyl), CH$_2$ or

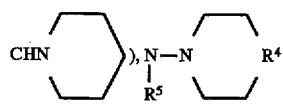

or OR$^6$(in which R$^6$ represents substituted or unsubstituted lower alkyl, or substituted or unsubstituted C$_{6-10}$ nonheterocyclic aryl); and W represents

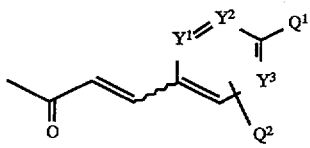

O(CH$_2$)$_n$CO$_2$R$^7$ in which Y$^1$, Y$^2$ and Y$^3$ independently represent CH or N, Q$^1$ and Q$^2$ independently represent hydrogen, OR$^7$(in which R$^7$ represents hydrogen or substituted or unsubstituted lower alkyl), $NR^2R^3$, $NECO_2R^6$, or $O(CH_2)_nR^8$ in which n represents an integer of 1 to 4, and $R^8$ represents $CO_2R^7$, $N_3$, or $NR^2R^3$, provided that when $Y^1$, $Y^2$ and $Y^3$ are CH, at least one of $Q^1$ and $Q^2$ is a group other than hydrogen or alkoxy, or

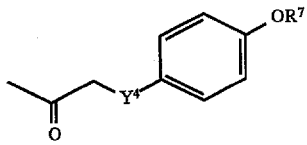

(in which $Y^4$ represents oxygen, sulfur or NH, or a pharmaceutically acceptable salt thereof.

2. A DC-89 derivative represented by the formula:

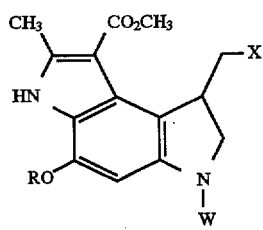

wherein X represents Cl or Br, R represents $COR^1$ in which $R^1$ represents substituted or unsubstituted lower alkyl (wherein the substituted lower alkyl is substituted with 1 to 3 moieties selected from the group consisting of lower alkoxy, lower alkylthio optionally substituted with carboxy, carboxy, lower alkoxycarbonyl, amino, mono- or di(lower alkyl)amino, cyclic amino optionally substituted with lower alkyl or cyclic amino, halogen and phenyl), $NR^2R^3$ (in which $R^2$ and $R^3$ independently represent substituted or unsubstituted lower alkyl or amino) or

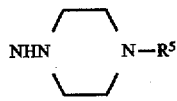

(in which $R^5$ represents lower alkyl); and W represents

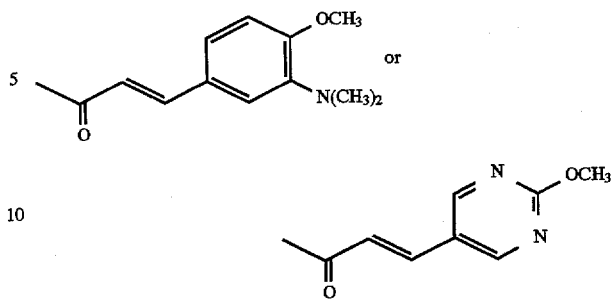

or a pharmaceutically acceptable salt thereof.

3. A DC-89 derivative represented by the formula:

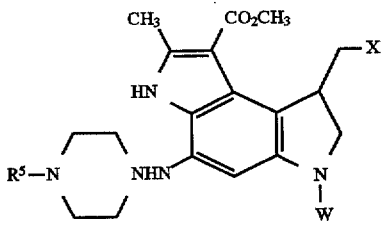

wherein X represents Br, $R^5$ represents lower alkyl; and W represents

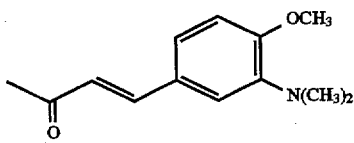

or a pharmaceutically acceptable salt thereof.

* * * * *

UNITED STATES PATENT AND TRADEMARK OFFICE
CERTIFICATE OF CORRECTION

PATENT NO. : 5,670,492

DATED : September 23, 1997

INVENTOR(S): NOBUYOSHI AMISHIRO ET AL.                    Page 1 of 4

It is certified that error appears in the above-identified patent and that said Letters Patent is hereby corrected as shown below:

COLUMN 4

Line 2, " 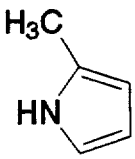 " should read -- 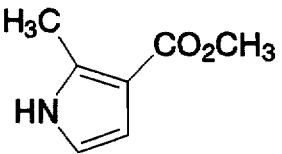 --.

COLUMN 5

Line 40, " 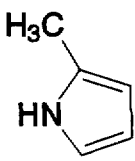 " should read -- 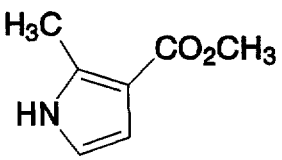 --.

COLUMN 6

Line 20, " 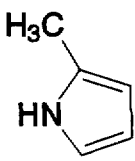 " should read -- 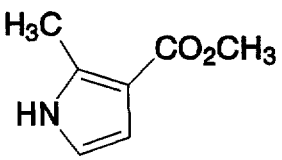 --.

COLUMN 12
  Table 1, "CONHCH$_3$CO$_2$H" should read --CONHCH$_2$CO$_2$H--.

UNITED STATES PATENT AND TRADEMARK OFFICE
CERTIFICATE OF CORRECTION

PATENT NO. : 5,670,492

DATED : September 23, 1997

INVENTOR(S): NOBUYOSHI AMISHIRO ET AL.

It is certified that error appears in the above-identified patent and that said Letters Patent is hereby corrected as shown below:

COLUMN 25
  Line 55, "cells/mi." should read --cells/ml.--.

COLUMN 26
  Line 63, "6.2" should read --0.2--.

COLUMN 29
  Line 18, "JNM-EX270(270MNz)" should read
    --JNM-EX270(270MHz)--;
  Line 66, "IR(KBr)v(cm$^1$;" should read --IR(KBr)v(cm$^{-1}$);--.

COLUMN 33
  Line 13, "mi" should read --ml--.

COLUMN 35
  Line 23, "18 9" should read --18.9--.

COLUMN 37
  Line 26, "p-nitrophenyl." should read --p-nitrophenyl--.

COLUMN 40
  Line 40, "from" should be deleted.

COLUMN 41
  Line 50, "IR(KBr)v(cm);" should read --IR(KBr)v(cm$^{-1}$);--.

COLUMN 42
  Line 57, "from" should be deleted.

UNITED STATES PATENT AND TRADEMARK OFFICE
CERTIFICATE OF CORRECTION

PATENT NO. : 5,670,492

DATED : September 23, 1997

INVENTOR(S): NOBUYOSHI AMISHIRO ET AL.

Page 3 of 4

It is certified that error appears in the above-identified patent and that said Letters Patent is hereby corrected as shown below:

COLUMN 43
Line 10, "IR(KBr)ν(cm⁻);" should read --IR(KBr)ν(cm⁻¹);--.

COLUMN 45
Line 8, "26.(8" should read --26(8--.

COLUMN 46
Line 16, "With" should read --with--.

COLUMN 48
Line 1, "IR(KBr)ν(cm¹); should read --IR(KBr)ν(cm⁻¹).

COLUMN 50
Line 8, "IR(KBr)ν(cm⁻);" should read --IR(KBr)ν(cm⁻¹);--.

COLUMN 51
Line 14, "IR(KBr)ν(cm⁻);" should read --IR(KBr)ν(cm⁻¹);--.

COLUMN 54
Line 59, "IR(KBr)ν(cm⁻);" should read --IR(KBr)ν(cm⁻¹);--.

COLUMN 56
Line 62, "1.52 mI" should read --1.52 ml--.

COLUMN 57
Line 53, "ahnydrous" should read --anhydrous--.

UNITED STATES PATENT AND TRADEMARK OFFICE
CERTIFICATE OF CORRECTION

PATENT NO. : 5,670,492

DATED : September 23, 1997

INVENTOR(S): NOBUYOSHI AMISHIRO ET AL.

Page 4 of 4

It is certified that error appears in the above-identified patent and that said Letters Patent is hereby corrected as shown below:

COLUMN 62
Line 19, "trlethylamlne" should read --triethylamine--.

COLUMN 65
Line 41, "9:1:0.2)" should read --9:1:0:2)--.

COLUMN 70
Line 12, "IR(KBr)v(cm$^{31\ 1}$);" should read --IR(KBr)v(cm$^{-1}$);--.

COLUMN 73
Line "NECO$_2$R$^6$," should read --NHCO$_2$R$^6$,--.

Signed and Sealed this

Seventh Day of April, 1998

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,670,492

DATED : September 23, 1997

INVENTOR(S): NOBUYOSHI AMISHIRO ET AL.

It is certified that error appears in the above-identified patent and that said Letters Patent is hereby corrected as shown below:

<u>COLUMN 74</u>:

Lines 20-26,

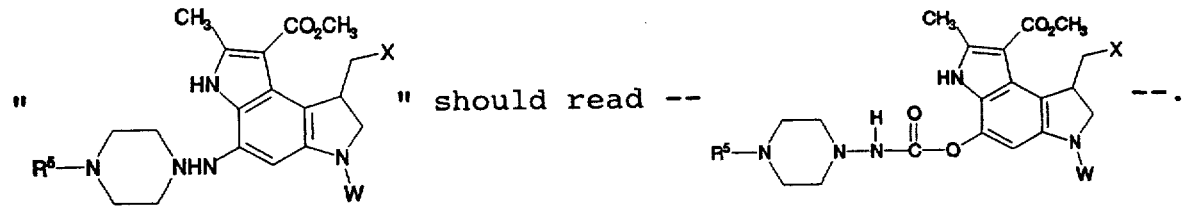

Signed and Sealed this

Twelfth Day of May, 1998

*Attest:*

BRUCE LEHMAN

*Attesting Officer*  *Commissioner of Patents and Trademarks*